US008486629B2

(12) United States Patent
Banerjee et al.

(10) Patent No.: US 8,486,629 B2
(45) Date of Patent: Jul. 16, 2013

(54) CREATION OF FUNCTIONALIZED MICROPARTICLE LIBRARIES BY OLIGONUCLEOTIDE LIGATION OR ELONGATION

(75) Inventors: Sukanta Banerjee, Pennington, NJ (US); Jiacheng Yang, Hillsboro, NJ (US); Michael Seul, Fanwood, NJ (US)

(73) Assignee: BioArray Solutions, Ltd., Warren, NJ (US)

( * ) Notice: Subject to any disclaimer, the term of this patent is extended or adjusted under 35 U.S.C. 154(b) by 594 days.

(21) Appl. No.: 11/411,510

(22) Filed: Apr. 26, 2006

(65) Prior Publication Data
US 2006/0275799 A1 Dec. 7, 2006

Related U.S. Application Data

(60) Provisional application No. 60/686,333, filed on Jun. 1, 2005.

(51) Int. Cl.
*C12Q 1/68* (2006.01)
*C40B 50/00* (2006.01)

(52) U.S. Cl.
USPC .......................................... 435/6.11; 506/23

(58) Field of Classification Search
USPC .......................................... 435/6.11; 506/23
See application file for complete search history.

(56) References Cited

U.S. PATENT DOCUMENTS

| 3,329,638 | A | 7/1967 | Blyth |
| 3,574,614 | A | 4/1971 | Carreira |
| 3,790,492 | A | 2/1974 | Fulwyler |
| 3,957,741 | A | 5/1976 | Rembaum et al. |
| 3,982,182 | A | 9/1976 | Hogg |
| 3,989,775 | A | 11/1976 | Jack et al. |
| 3,998,525 | A | 12/1976 | Giglia |
| 4,003,713 | A | 1/1977 | Bowser |
| 4,046,667 | A | 9/1977 | Goetz |
| 4,055,799 | A | 10/1977 | Coster et al. |
| 4,075,013 | A | 2/1978 | Ward et al. |
| 4,102,990 | A | 7/1978 | Uzgiris |
| 4,140,937 | A | 2/1979 | Vecht et al. |
| 4,143,203 | A | 3/1979 | Rigopulos et al. |
| 4,199,363 | A | 4/1980 | Chen |
| 4,258,001 | A | 3/1981 | Pierce et al. |
| 4,267,235 | A | 5/1981 | Rembaum et al. |
| 4,275,053 | A | 6/1981 | Rosenfield et al. |
| 4,326,008 | A | 4/1982 | Rembaum |
| 4,336,173 | A | 6/1982 | Ugelstad |
| 4,339,337 | A | 7/1982 | Tricot et al. |
| 4,358,388 | A | 11/1982 | Daniel et al. |
| 4,383,529 | A | 5/1983 | Webster |
| 4,421,896 | A | 12/1983 | Dorman |
| 4,456,513 | A | 6/1984 | Kawai et al. |
| 4,459,378 | A | 7/1984 | Ugelstad |
| 4,487,855 | A | 12/1984 | Shih et al. |
| 4,497,208 | A | 2/1985 | Oja et al. |
| 4,499,052 | A | 2/1985 | Fulwyler |
| 4,575,407 | A | 3/1986 | Diller |
| 4,591,550 | A | 5/1986 | Hafeman et al. |
| 4,602,989 | A | 7/1986 | Culkin |
| 4,613,559 | A | 9/1986 | Ober et al. |
| 4,647,544 | A | 3/1987 | Nicoli et al. |
| 4,654,267 | A | 3/1987 | Ugelstad et al. |
| 4,663,408 | A | 5/1987 | Schulz et al. |
| 4,665,020 | A | 5/1987 | Saunders |
| 4,672,040 | A | 6/1987 | Josephson |
| 4,679,439 | A | 7/1987 | Culkin |
| 4,680,332 | A | 7/1987 | Hair et al. |
| 4,702,598 | A | 10/1987 | Böhmer |
| 4,717,655 | A | 1/1988 | Fulwyler |
| 4,753,775 | A | 6/1988 | Ebersole et al. |
| 4,774,189 | A | 9/1988 | Schwartz |
| 4,774,265 | A | 9/1988 | Ugelstad et al. |
| 4,791,310 | A | 12/1988 | Honig et al. |
| 4,795,698 | A | 1/1989 | Owen et al. |
| 4,806,313 | A | 2/1989 | Ebersole et al. |
| 4,806,776 | A | 2/1989 | Kley |
| 4,822,746 | A | 4/1989 | Walt |
| 4,824,941 | A | 4/1989 | Gordon et al. |

(Continued)

FOREIGN PATENT DOCUMENTS

| CA | 1248873 | 1/1989 |
| DE | 4035714 | 5/1992 |

(Continued)

OTHER PUBLICATIONS

Wiedmann et al., Ligase Chain Reaction (LCR)—Overview and Applications, PCR Methods and Applications, Genome Research, 1994, S51-S64.*
Lee, Hye Jin, et al., "Fabricating RNA Microarrays with RNA-DNA Surface Ligation Chemistry," *Analytical Chemistry*, vol. 77, No. 23, 7832-7837 (Dec. 1, 2005).
Barany, Francis, "Genetic Disease Detection and DNA Amplification using Cloned Thermostable Ligase," *Proceedings of the National Acadamy of Sciences of the United States of America*, vol. 88, 189-193 (Jan. 1991).
Schouten, Jan P., et al., "Relative Quantification of 40 Nucleic Acid Sequences by Multiplex Ligation-Dependent Probe Amplification," *Nucleic Acids Research*, vol. 30, No. 12, e57 (Jun. 15, 2002).
Iannone, Marie A., et al., "Multiplexed Single Nucleotide Polymorphism Genotyping by Oligonucleotide Ligation and Flow Cytometry," *Cytometry*, vol. 39, Issue 2, 131-140 (Feb. 17, 2000).
Sgaramella et al, "CXII. Synthesis of Structural Gene for Alanine Transfer RNA from Yeast. Joining of the Polydeoxynucleotides to form DNA duplex" J. Mol. Biol 1972;72:427-444.

(Continued)

*Primary Examiner* — Amber D Steele
(74) *Attorney, Agent, or Firm* — Womble Carlyle Sandridge & Rice LLP

(57) ABSTRACT

Disclosed are methods of for constructing a bead-displayed library of oligonucleotide probes (or sequence-modified capture moieties such as protein-nucleic acid conjugates) by ligation of a capture probe, having an analyte-specific sequence, to an anchor probe that is attached, at its 5'-end, (or possibly at the 3' end) to an encoded carrier such as a color-coded microparticle ("bead"). Such a library can also be constructed by elongation of an anchor probe, using a second probe as the elongation template, wherein the second probe has an anchor-specific subsequence and an analyte-specific subsequence.

4 Claims, 9 Drawing Sheets

U.S. PATENT DOCUMENTS

| | | | |
|---|---|---|---|
| 4,829,101 A | 5/1989 | Kraemer et al. | |
| 4,832,814 A | 5/1989 | Root | |
| 4,851,331 A | 7/1989 | Vary et al. | |
| 4,873,102 A | 10/1989 | Chang et al. | |
| 4,891,324 A | 1/1990 | Pease et al. | |
| 4,911,806 A | 3/1990 | Hofmann | |
| 4,920,056 A | 4/1990 | Dasgupta | |
| 4,994,373 A | 2/1991 | Stavrianopoulos et al. | |
| 4,996,265 A | 2/1991 | Okubo et al. | |
| 5,002,867 A | 3/1991 | Macevicz | |
| 5,015,452 A | 5/1991 | Matijevic | |
| 5,028,545 A | 7/1991 | Soini | |
| 5,073,498 A | 12/1991 | Schwartz et al. | |
| 5,075,217 A | 12/1991 | Weber | |
| 5,091,206 A | 2/1992 | Wang et al. | |
| 5,105,305 A | 4/1992 | Betzig et al. | |
| 5,114,864 A | 5/1992 | Walt | |
| 5,126,239 A | 6/1992 | Livak et al. | |
| 5,128,006 A | 7/1992 | Mitchell et al. | |
| 5,132,097 A | 7/1992 | Van Deusen et al. | |
| 5,132,242 A | 7/1992 | Cheung | |
| 5,143,853 A | 9/1992 | Walt | |
| 5,143,854 A | 9/1992 | Pirrung et al. | |
| 5,147,777 A | 9/1992 | Sutton et al. | |
| 5,155,044 A | 10/1992 | Ledis et al. | |
| 5,173,159 A | 12/1992 | Dutertre | |
| 5,185,066 A | 2/1993 | Golias | |
| 5,187,096 A | 2/1993 | Giaever et al. | |
| 5,194,300 A | 3/1993 | Cheung | |
| 5,194,393 A | 3/1993 | Hugl et al. | |
| 5,208,111 A | 5/1993 | Decher et al. | |
| 5,221,417 A | 6/1993 | Basavanhally | |
| 5,234,809 A | 8/1993 | Boom et al. | |
| 5,241,012 A | 8/1993 | Clark | |
| 5,244,630 A | 9/1993 | Khalil et al. | |
| 5,244,636 A | 9/1993 | Walt et al. | |
| 5,244,813 A | 9/1993 | Walt et al. | |
| 5,250,264 A | 10/1993 | Walt et al. | |
| 5,252,494 A | 10/1993 | Walt | |
| 5,254,477 A | 10/1993 | Walt | |
| 5,266,238 A | 11/1993 | Haacke et al. | |
| 5,266,427 A | 11/1993 | Iwase et al. | |
| 5,266,497 A | 11/1993 | Imai et al. | |
| 5,281,370 A | 1/1994 | Asher et al. | |
| 5,283,079 A | 2/1994 | Wang et al. | |
| 5,288,577 A | 2/1994 | Yamaguchi et al. | |
| 5,298,741 A | 3/1994 | Walt et al. | |
| 5,301,044 A | 4/1994 | Wright | |
| 5,306,618 A | 4/1994 | Prober et al. | |
| 5,308,586 A | 5/1994 | Fritsche et al. | |
| 5,308,749 A | 5/1994 | Sutton et al. | |
| 5,320,814 A | 6/1994 | Walt et al. | |
| 5,326,691 A | 7/1994 | Hozier | |
| 5,326,692 A | 7/1994 | Brinkley et al. | |
| 5,329,461 A | 7/1994 | Allen et al. | |
| 5,348,853 A | 9/1994 | Wang et al. | |
| 5,356,713 A | 10/1994 | Charmot et al. | |
| 5,362,653 A | 11/1994 | Carr et al. | |
| 5,364,759 A | 11/1994 | Caskey et al. | |
| 5,382,512 A | 1/1995 | Smethers et al. | |
| 5,382,801 A | 1/1995 | Kanayama | |
| 5,389,549 A | 2/1995 | Hamaguchi et al. | |
| 5,395,688 A | 3/1995 | Wang et al. | |
| 5,405,784 A | 4/1995 | Van Hoegaerden | |
| 5,412,087 A | 5/1995 | McGall et al. | |
| 5,415,835 A | 5/1995 | Brueck et al. | |
| 5,422,246 A | 6/1995 | Koopal et al. | |
| 5,436,327 A | 7/1995 | Southern et al. | |
| 5,442,246 A | 8/1995 | Azegami et al. | |
| 5,444,330 A | 8/1995 | Leventis et al. | |
| 5,447,440 A | 9/1995 | Davis et al. | |
| 5,470,534 A | 11/1995 | Imai et al. | |
| 5,474,796 A | 12/1995 | Brennan | |
| 5,474,895 A | 12/1995 | Ishii et al. | |
| 5,480,723 A | 1/1996 | Klainer et al. | |
| 5,488,567 A | 1/1996 | Allen et al. | |
| 5,496,997 A | 3/1996 | Pope | |
| 5,498,392 A | 3/1996 | Wilding et al. | |
| 5,510,270 A | 4/1996 | Fodor et al. | |
| 5,512,157 A | 4/1996 | Guadagno et al. | |
| 5,512,439 A | 4/1996 | Hornes et al. | |
| 5,512,490 A | 4/1996 | Walt et al. | |
| 5,514,785 A | 5/1996 | VanNess et al. | |
| 5,516,635 A | 5/1996 | Ekins et al. | |
| 5,518,883 A | 5/1996 | Soini | |
| 5,523,231 A | 6/1996 | Reeve | |
| 5,527,710 A | 6/1996 | Nacamulli et al. | |
| 5,528,392 A | 6/1996 | Nakagawa et al. | |
| 5,532,128 A | 7/1996 | Eggers et al. | |
| 5,536,648 A | 7/1996 | Kemp et al. | |
| 5,545,522 A | 8/1996 | Van Gelder et al. | |
| 5,545,531 A | 8/1996 | Rava et al. | |
| 5,552,086 A | 9/1996 | Siiman et al. | |
| 5,552,270 A | 9/1996 | Khrapko et al. | |
| 5,556,752 A | 9/1996 | Lockhart et al. | |
| 5,565,324 A | 10/1996 | Still et al. | |
| 5,567,304 A | 10/1996 | Datta et al. | |
| 5,567,627 A | 10/1996 | Lehnen | |
| 5,573,909 A | 11/1996 | Singer et al. | |
| 5,582,988 A | 12/1996 | Backus et al. | |
| 5,585,069 A | 12/1996 | Zanzucchi et al. | |
| 5,587,128 A | 12/1996 | Wilding et al. | |
| 5,593,838 A | 1/1997 | Zanzucchi et al. | |
| 5,593,839 A | 1/1997 | Hubbell et al. | |
| 5,602,042 A | 2/1997 | Farber | |
| 5,604,097 A | 2/1997 | Brenner | |
| 5,604,099 A | 2/1997 | Erlich et al. | |
| 5,605,798 A * | 2/1997 | Koster | 435/6 |
| 5,610,287 A | 3/1997 | Nikiforov et al. | |
| 5,627,040 A | 5/1997 | Bierre et al. | |
| 5,632,957 A | 5/1997 | Heller et al. | |
| 5,633,724 A | 5/1997 | King et al. | |
| 5,633,972 A | 5/1997 | Walt et al. | |
| 5,637,508 A | 6/1997 | Kidwell et al. | |
| 5,639,603 A | 6/1997 | Dower et al. | |
| 5,639,606 A | 6/1997 | Willey | |
| 5,643,765 A | 7/1997 | Willey | |
| 5,648,124 A | 7/1997 | Sutor | |
| 5,650,488 A | 7/1997 | O'Hare | |
| 5,650,489 A | 7/1997 | Lam et al. | |
| 5,652,059 A | 7/1997 | Margel | |
| 5,652,107 A | 7/1997 | Lizardi et al. | |
| 5,653,939 A | 8/1997 | Hollis et al. | |
| 5,660,990 A | 8/1997 | Rao et al. | |
| 5,667,667 A | 9/1997 | Southern | |
| 5,674,686 A | 10/1997 | Schumm et al. | |
| 5,674,698 A | 10/1997 | Zarling et al. | |
| 5,679,524 A | 10/1997 | Nikiforov et al. | |
| 5,690,894 A | 11/1997 | Pinkel et al. | |
| 5,698,271 A | 12/1997 | Liberti et al. | |
| 5,700,637 A | 12/1997 | Southern | |
| 5,700,897 A | 12/1997 | Klainer et al. | |
| 5,714,340 A | 2/1998 | Sutton et al. | |
| 5,714,521 A | 2/1998 | Kedem et al. | |
| 5,716,852 A | 2/1998 | Yager et al. | |
| 5,722,470 A | 3/1998 | Kedar et al. | |
| 5,723,218 A | 3/1998 | Haugland et al. | |
| 5,723,233 A | 3/1998 | Garza et al. | |
| 5,728,529 A | 3/1998 | Metzker et al. | |
| 5,736,349 A | 4/1998 | Sasaki et al. | |
| 5,744,299 A | 4/1998 | Henrickson et al. | |
| 5,744,305 A | 4/1998 | Fodor et al. | |
| 5,747,349 A | 5/1998 | Van den Engh et al. | |
| 5,751,629 A | 5/1998 | Nova et al. | |
| 5,763,175 A | 6/1998 | Brenner | |
| 5,763,198 A | 6/1998 | Hirth et al. | |
| 5,763,263 A | 6/1998 | Dehlinger | |
| 5,766,711 A | 6/1998 | Barmakian | |
| 5,766,963 A | 6/1998 | Baldwin et al. | |
| 5,770,358 A | 6/1998 | Dower et al. | |
| 5,770,367 A | 6/1998 | Southern et al. | |
| 5,770,455 A | 6/1998 | Cargill et al. | |
| 5,770,721 A | 6/1998 | Ershov et al. | |
| 5,773,222 A | 6/1998 | Scott | |
| 5,776,711 A | 7/1998 | Vyas et al. | |
| 5,779,976 A | 7/1998 | Leland et al. | |
| 5,786,219 A | 7/1998 | Zhang et al. | |

| Patent | Date | Inventor |
|---|---|---|
| 5,789,147 A | 8/1998 | Rubinstein et al. |
| 5,792,430 A | 8/1998 | Hamper |
| 5,800,992 A | 9/1998 | Fodor et al. |
| 5,807,755 A | 9/1998 | Ekins |
| 5,812,272 A | 9/1998 | King et al. |
| 5,814,524 A | 9/1998 | Walt et al. |
| 5,831,045 A | 11/1998 | Stolowitz et al. |
| 5,834,590 A | 11/1998 | Vinik et al. |
| 5,837,501 A | 11/1998 | Beumer et al. |
| 5,837,551 A | 11/1998 | Ekins |
| 5,837,832 A | 11/1998 | Chee et al. |
| 5,840,485 A | 11/1998 | Lebl et al. |
| 5,843,660 A | 12/1998 | Schumm et al. |
| 5,844,304 A | 12/1998 | Kata et al. |
| 5,846,708 A | 12/1998 | Hollis et al. |
| 5,855,753 A | 1/1999 | Trau et al. |
| 5,856,092 A | 1/1999 | Dale et al. |
| 5,858,804 A | 1/1999 | Zanzucchi et al. |
| 5,866,099 A | 2/1999 | Owen et al. |
| 5,866,331 A | 2/1999 | Singer et al. |
| 5,874,219 A | 2/1999 | Rava et al. |
| 5,876,946 A | 3/1999 | Burbaum et al. |
| 5,898,071 A | 4/1999 | Hawkins |
| 5,900,481 A | 5/1999 | Lough et al. |
| 5,922,617 A | 7/1999 | Wang et al. |
| 5,939,021 A | 8/1999 | Hansen et al. |
| 5,942,388 A | 8/1999 | Willner et al. |
| 5,945,525 A | 8/1999 | Uematsu et al. |
| 5,948,621 A | 9/1999 | Turner et al. |
| 5,948,627 A | 9/1999 | Lee et al. |
| 5,952,131 A | 9/1999 | Kumacheva et al. |
| 5,952,174 A * | 9/1999 | Nikiforov et al. .................. 435/6 |
| 5,959,098 A | 9/1999 | Goldberg et al. |
| 5,961,923 A | 10/1999 | Nova et al. |
| 5,965,235 A | 10/1999 | McGuire et al. |
| 5,965,452 A | 10/1999 | Kovacs |
| 5,968,736 A | 10/1999 | Still et al. |
| 5,981,176 A | 11/1999 | Wallace |
| 5,981,180 A | 11/1999 | Chandler et al. |
| 5,988,432 A | 11/1999 | Sun |
| 5,989,835 A | 11/1999 | Dunlay et al. |
| 5,993,935 A | 11/1999 | Rasmussen et al. |
| 5,994,066 A | 11/1999 | Bergeron et al. |
| 6,001,614 A | 12/1999 | Akhavan-Tafti |
| 6,004,744 A | 12/1999 | Goelet et al. |
| 6,007,996 A | 12/1999 | McNamara et al. |
| 6,013,531 A | 1/2000 | Wang et al. |
| 6,014,451 A | 1/2000 | Berry et al. |
| 6,015,664 A | 1/2000 | Henrickson et al. |
| 6,015,666 A | 1/2000 | Springer et al. |
| 6,017,696 A | 1/2000 | Heller |
| 6,023,540 A | 2/2000 | Walt et al. |
| 6,023,590 A | 2/2000 | Abe et al. |
| 6,025,905 A | 2/2000 | Sussman |
| 6,027,889 A | 2/2000 | Barany et al. |
| 6,027,945 A | 2/2000 | Smith et al. |
| 6,033,547 A | 3/2000 | Trau et al. |
| 6,043,354 A | 3/2000 | Hillebrand et al. |
| 6,048,690 A | 4/2000 | Heller et al. |
| 6,054,270 A | 4/2000 | Southern |
| 6,060,243 A | 5/2000 | Tang et al. |
| 6,063,569 A | 5/2000 | Gildea et al. |
| 6,068,818 A | 5/2000 | Ackley et al. |
| 6,075,905 A | 6/2000 | Herman et al. |
| 6,077,669 A | 6/2000 | Little et al. |
| 6,077,674 A | 6/2000 | Schleifer et al. |
| 6,080,585 A | 6/2000 | Southern et al. |
| 6,083,699 A | 7/2000 | Leushner et al. |
| 6,083,763 A | 7/2000 | Balch |
| 6,084,991 A | 7/2000 | Sampas |
| 6,086,736 A | 7/2000 | Dasgupta et al. |
| 6,090,458 A | 7/2000 | Murakami |
| 6,090,545 A | 7/2000 | Wohlstadter et al. |
| 6,090,555 A | 7/2000 | Fiekowsky et al. |
| 6,090,912 A | 7/2000 | Lebl et al. |
| 6,096,368 A | 8/2000 | Sun |
| 6,100,030 A | 8/2000 | Feazel et al. |
| 6,103,379 A | 8/2000 | Margel et al. |
| 6,106,685 A | 8/2000 | McBride et al. |
| 6,120,666 A | 9/2000 | Jacobson et al. |
| 6,122,599 A | 9/2000 | Mehta |
| 6,123,263 A | 9/2000 | Feng |
| 6,124,092 A | 9/2000 | O'Neill et al. |
| 6,126,731 A | 10/2000 | Kemeny et al. |
| 6,130,101 A | 10/2000 | Mao et al. |
| 6,132,685 A | 10/2000 | Kercso et al. |
| 6,132,997 A | 10/2000 | Shannon |
| 6,136,171 A | 10/2000 | Frazier et al. |
| 6,136,468 A | 10/2000 | Mitchell, Jr. et al. |
| 6,139,831 A | 10/2000 | Shivashankar et al. |
| 6,141,046 A | 10/2000 | Roth et al. |
| 6,143,499 A | 11/2000 | Mirzabekov et al. |
| 6,149,789 A | 11/2000 | Benecke et al. |
| 6,150,095 A | 11/2000 | Southern et al. |
| 6,151,062 A | 11/2000 | Inoguchi et al. |
| 6,153,375 A | 11/2000 | Kobylecki et al. |
| 6,153,389 A | 11/2000 | Haarer et al. |
| 6,156,502 A | 12/2000 | Beattie |
| 6,167,910 B1 | 1/2001 | Chow |
| 6,172,218 B1 | 1/2001 | Brenner |
| 6,180,226 B1 | 1/2001 | McArdle et al. |
| 6,183,970 B1 | 2/2001 | Okano et al. |
| 6,187,540 B1 | 2/2001 | Staub et al. |
| 6,193,866 B1 | 2/2001 | Bader et al. |
| 6,193,951 B1 | 2/2001 | Ottoboni et al. |
| 6,200,737 B1 | 3/2001 | Walt et al. |
| 6,200,814 B1 | 3/2001 | Malmqvist et al. |
| 6,203,993 B1 | 3/2001 | Shuber et al. |
| 6,207,369 B1 | 3/2001 | Wohlstadter et al. |
| 6,209,589 B1 | 4/2001 | Hare et al. |
| 6,218,111 B1 | 4/2001 | Southern et al. |
| 6,221,598 B1 | 4/2001 | Schumm et al. |
| 6,232,066 B1 | 5/2001 | Felder et al. |
| 6,235,471 B1 | 5/2001 | Knapp et al. |
| 6,238,863 B1 | 5/2001 | Schumm et al. |
| 6,245,508 B1 | 6/2001 | Heller et al. |
| 6,251,592 B1 | 6/2001 | Tang et al. |
| 6,251,595 B1 | 6/2001 | Gordon et al. |
| 6,251,687 B1 | 6/2001 | Buechler et al. |
| 6,251,691 B1 | 6/2001 | Seul |
| 6,254,754 B1 | 7/2001 | Ross et al. |
| 6,254,827 B1 | 7/2001 | Ackley et al. |
| 6,261,430 B1 | 7/2001 | Yager et al. |
| 6,264,815 B1 | 7/2001 | Pethig et al. |
| 6,264,825 B1 | 7/2001 | Blackburn et al. |
| 6,266,459 B1 | 7/2001 | Walt et al. |
| 6,267,858 B1 | 7/2001 | Parce et al. |
| 6,268,219 B1 | 7/2001 | Mcbride et al. |
| 6,268,222 B1 | 7/2001 | Chandler et al. |
| 6,271,856 B1 | 8/2001 | Krishnamurthy |
| 6,277,579 B1 | 8/2001 | Lazar et al. |
| 6,280,618 B2 | 8/2001 | Watkins et al. |
| 6,287,778 B1 | 9/2001 | Huang et al. |
| 6,294,063 B1 | 9/2001 | Becker et al. |
| 6,297,062 B1 | 10/2001 | Gombinski |
| 6,303,316 B1 | 10/2001 | Kiel et al. |
| 6,306,643 B1 | 10/2001 | Gentalen et al. |
| 6,307,039 B1 | 10/2001 | Southern et al. |
| 6,309,602 B1 | 10/2001 | Ackley et al. |
| 6,312,134 B1 | 11/2001 | Jain et al. |
| 6,316,186 B1 | 11/2001 | Ekins |
| 6,318,970 B1 | 11/2001 | Backhouse |
| 6,319,472 B1 | 11/2001 | Ackley et al. |
| 6,319,674 B1 | 11/2001 | Fulcrand et al. |
| 6,321,791 B1 | 11/2001 | Chow |
| 6,327,410 B1 | 12/2001 | Walt et al. |
| 6,342,355 B1 | 1/2002 | Hacia et al. |
| 6,349,144 B1 | 2/2002 | Shams |
| 6,355,419 B1 | 3/2002 | Alfenito |
| 6,355,431 B1 | 3/2002 | Chee et al. |
| 6,355,491 B1 | 3/2002 | Zhou et al. |
| 6,358,387 B1 | 3/2002 | Kopf-Sill et al. |
| 6,361,916 B1 | 3/2002 | Chen et al. |
| 6,361,945 B1 | 3/2002 | Becker et al. |
| 6,365,418 B1 | 4/2002 | Wagner et al. |
| 6,368,799 B1 | 4/2002 | Chee |
| 6,387,707 B1 | 5/2002 | Seul et al. |
| 6,399,328 B1 | 6/2002 | Vournakis et al. |

| | | | | | | |
|---|---|---|---|---|---|---|
| 6,403,309 | B1 | 6/2002 | Iris et al. | 7,291,504 | B2 | 11/2007 | Seul |
| 6,426,615 | B1 | 7/2002 | Mehta | 7,306,918 | B2 | 12/2007 | Hashmi et al. |
| 6,429,027 | B1 | 8/2002 | Chee et al. | 7,320,864 | B2 | 1/2008 | Yang |
| 6,448,012 | B1 | 9/2002 | Schwartz | 7,335,153 | B2 | 2/2008 | Seul et al. |
| 6,451,191 | B1 | 9/2002 | Bentsen et al. | 7,344,841 | B2 | 3/2008 | Hashmi et al. |
| 6,458,547 | B1 | 10/2002 | Bryan et al. | 7,358,097 | B2 | 4/2008 | Seul et al. |
| 6,468,811 | B1 | 10/2002 | Seul | 7,390,676 | B2 | 6/2008 | Seul et al. |
| 6,480,791 | B1 | 11/2002 | Strathmann | 7,425,416 | B2 | 9/2008 | Hashmi et al. |
| 6,488,872 | B1 | 12/2002 | Beebe et al. | 7,427,512 | B2 | 9/2008 | Seul |
| 6,494,924 | B1 | 12/2002 | Auweter et al. | 7,501,253 | B2 | 3/2009 | Pourmand et al. |
| 6,498,863 | B1 | 12/2002 | Gaidoukevitch et al. | 7,526,114 | B2 | 4/2009 | Xia et al. |
| 6,500,620 | B2 | 12/2002 | Yu et al. | 7,582,488 | B2 | 9/2009 | Banerjee et al. |
| 6,503,680 | B1 | 1/2003 | Chen et al. | 7,595,279 | B2 | 9/2009 | Wang et al. |
| 6,506,564 | B1 | 1/2003 | Mirkin et al. | 7,615,345 | B2 | 11/2009 | Seul |
| 6,509,158 | B1 | 1/2003 | Schwartz | 7,737,088 | B1 | 6/2010 | Stahler et al. |
| 6,514,688 | B2 | 2/2003 | Muller-Schulte | 7,749,774 | B2 | 7/2010 | Seul |
| 6,514,714 | B1 | 2/2003 | Lee et al. | 7,790,380 | B2 | 9/2010 | Yang |
| 6,514,771 | B1 | 2/2003 | Seul | 7,848,889 | B2 | 12/2010 | Xia et al. |
| 6,515,649 | B1 | 2/2003 | Albert et al. | 7,940,968 | B2 | 5/2011 | Seul et al. |
| 6,521,747 | B2 | 2/2003 | Anastasio et al. | 2001/0034614 | A1 | 10/2001 | Fletcher-Haynes et al. |
| 6,528,264 | B1 | 3/2003 | Pal et al. | 2001/0044531 | A1 | 11/2001 | McGall et al. |
| 6,531,292 | B1 | 3/2003 | Rine et al. | 2001/0046602 | A1 | 11/2001 | Chandler et al. |
| 6,531,323 | B1 | 3/2003 | Shinoki et al. | 2001/0049095 | A1 | 12/2001 | Webster |
| 6,534,274 | B2 | 3/2003 | Becker et al. | 2002/0006634 | A1 | 1/2002 | Han et al. |
| 6,534,293 | B1 | 3/2003 | Barany et al. | 2002/0015952 | A1 | 2/2002 | Anderson et al. |
| 6,540,895 | B1 | 4/2003 | Spence et al. | 2002/0022276 | A1 | 2/2002 | Zhou et al. |
| 6,605,453 | B2 | 8/2003 | Ozkan et al. | 2002/0029235 | A1 | 3/2002 | Lock et al. |
| 6,605,474 | B1 | 8/2003 | Cole | 2002/0031841 | A1 | 3/2002 | Asher et al. |
| 6,610,256 | B2 | 8/2003 | Schwartz | 2002/0032252 | A1 | 3/2002 | Ishizuka |
| 6,620,584 | B1 | 9/2003 | Chee et al. | 2002/0039728 | A1 | 4/2002 | Kain et al. |
| 6,642,062 | B2 * | 11/2003 | Kauvar et al. .................. 436/518 | 2002/0045169 | A1 | 4/2002 | Shoemaker et al. |
| 6,645,432 | B1 | 11/2003 | Anderson et al. | 2002/0081714 | A1 | 6/2002 | Jain et al. |
| 6,650,703 | B1 | 11/2003 | Schwarzmann et al. | 2002/0102567 | A1 | 8/2002 | Fodor et al. |
| 6,670,128 | B2 | 12/2003 | Smith et al. | 2002/0125138 | A1 | 9/2002 | Medoro |
| 6,692,914 | B1 | 2/2004 | Klaerner et al. | 2002/0137074 | A1 | 9/2002 | Piunno et al. |
| 6,703,288 | B2 | 3/2004 | Nagasawa et al. | 2002/0142318 | A1 | 10/2002 | Cattell et al. |
| 6,706,163 | B2 | 3/2004 | Seul et al. | 2002/0150909 | A1 | 10/2002 | Stuelpnagel et al. |
| 6,713,309 | B1 | 3/2004 | Anderson et al. | 2002/0155481 | A1 | 10/2002 | Hirota et al. |
| 6,730,515 | B2 | 5/2004 | Kocher | 2002/0166766 | A1 | 11/2002 | Seul et al. |
| 6,743,581 | B1 | 6/2004 | Vo-Dinh | 2002/0182609 | A1 | 12/2002 | Arcot |
| 6,760,157 | B1 | 7/2004 | Stover et al. | 2002/0187501 | A1 | 12/2002 | Huang et al. |
| 6,779,559 | B2 | 8/2004 | Parce et al. | 2002/0197728 | A1 | 12/2002 | Kaufman et al. |
| 6,797,524 | B1 | 9/2004 | Seul | 2002/0198665 | A1 | 12/2002 | Seul et al. |
| 6,806,050 | B2 | 10/2004 | Zhou et al. | 2003/0003272 | A1 | 1/2003 | Laguitton |
| 6,812,005 | B2 | 11/2004 | Fan et al. | 2003/0004594 | A1 | 1/2003 | Liu et al. |
| 6,838,289 | B2 | 1/2005 | Bell et al. | 2003/0006143 | A1 | 1/2003 | Banerjee et al. |
| 6,844,156 | B2 | 1/2005 | Rosen | 2003/0012693 | A1 | 1/2003 | Otillar et al. |
| 6,869,798 | B2 | 3/2005 | Crews et al. | 2003/0012699 | A1 | 1/2003 | Moore et al. |
| 6,887,701 | B2 | 5/2005 | Anderson et al. | 2003/0022370 | A1 | 1/2003 | Casagrande et al. |
| 6,890,741 | B2 | 5/2005 | Fan et al. | 2003/0022393 | A1 | 1/2003 | Seul et al. |
| 6,897,271 | B1 | 5/2005 | Domschke et al. | 2003/0031351 | A1 | 2/2003 | Yim |
| 6,905,881 | B2 | 6/2005 | Sammak et al. | 2003/0038812 | A1 | 2/2003 | Bartell |
| 6,908,737 | B2 | 6/2005 | Ravkin et al. | 2003/0040129 | A1 | 2/2003 | Shah |
| 6,942,968 | B1 | 9/2005 | Dickinson et al. | 2003/0062422 | A1 | 4/2003 | Fateley et al. |
| 6,955,751 | B1 | 10/2005 | Seul | 2003/0077607 | A1 | 4/2003 | Hopfinger et al. |
| 6,955,889 | B1 | 10/2005 | Mercolino et al. | 2003/0082487 | A1 | 5/2003 | Burgess |
| 6,955,901 | B2 * | 10/2005 | Schouten .................. 435/91.1 | 2003/0082530 | A1 | 5/2003 | Soderlund et al. |
| 6,955,902 | B2 | 10/2005 | Chumakov et al. | 2003/0082531 | A1 | 5/2003 | Soderlund et al. |
| 6,958,245 | B2 | 10/2005 | Seul et al. | 2003/0082587 | A1 | 5/2003 | Seul et al. |
| 6,991,941 | B1 | 1/2006 | Seul | 2003/0087228 | A1 | 5/2003 | Bamdad et al. |
| 6,993,156 | B1 | 1/2006 | Szeliski et al. | 2003/0108913 | A1 | 6/2003 | Schouten |
| 7,015,047 | B2 | 3/2006 | Huang et al. | 2003/0129296 | A1 | 7/2003 | Kelso |
| 7,041,453 | B2 * | 5/2006 | Yang .................. 435/6 | 2003/0134326 | A1 | 7/2003 | Hansen et al. |
| 7,049,077 | B2 | 5/2006 | Yang | 2003/0138842 | A1 | 7/2003 | Seul et al. |
| 7,056,746 | B2 | 6/2006 | Seul et al. | 2003/0148335 | A1 | 8/2003 | Shen et al. |
| 7,060,431 | B2 | 6/2006 | Chee et al. | 2003/0152931 | A1 | 8/2003 | Chiou et al. |
| 7,090,759 | B1 | 8/2006 | Seul | 2003/0154108 | A1 | 8/2003 | Fletcher-Haynes et al. |
| 7,097,974 | B1 | 8/2006 | Stahler et al. | 2003/0177036 | A1 | 9/2003 | Oka et al. |
| 7,099,777 | B1 | 8/2006 | Ghandour | 2003/0182068 | A1 | 9/2003 | Battersby et al. |
| 7,115,370 | B2 * | 10/2006 | Ray et al. .................. 435/6 | 2003/0186220 | A1 | 10/2003 | Zhou et al. |
| 7,115,884 | B1 | 10/2006 | Walt et al. | 2004/0002073 | A1 | 1/2004 | Li et al. |
| 7,132,239 | B2 | 11/2006 | Livak et al. | 2004/0009614 | A1 | 1/2004 | Ahn et al. |
| 7,141,217 | B2 | 11/2006 | Karlsson et al. | 2004/0014073 | A1 | 1/2004 | Trau et al. |
| 7,144,119 | B2 | 12/2006 | Seul et al. | 2004/0048259 | A1 | 3/2004 | Hashmi et al. |
| 7,153,697 | B2 * | 12/2006 | Nakao .................. 436/172 | 2004/0093238 | A1 | 5/2004 | Deakter |
| 7,157,228 | B2 | 1/2007 | Hashmi et al. | 2004/0106121 | A1 | 6/2004 | Ugolin et al. |
| 7,195,913 | B2 | 3/2007 | Guire et al. | 2004/0132122 | A1 | 7/2004 | Banerjee et al. |
| 7,229,840 | B1 | 6/2007 | Wischerhoff | 2004/0137641 | A1 | 7/2004 | Holtlund et al. |
| 7,262,016 | B2 | 8/2007 | Huang et al. | 2004/0175734 | A1 | 9/2004 | Stahler et al. |

| | | | |
|---|---|---|---|
| 2004/0219520 A1 | 11/2004 | Mirkin et al. | |
| 2004/0229269 A1 | 11/2004 | Hashmi et al. | |
| 2005/0048570 A1 | 3/2005 | Weber et al. | |
| 2005/0112585 A1 | 5/2005 | Zichi et al. | |
| 2005/0143928 A1 | 6/2005 | Moser et al. | |
| 2005/0239098 A1 | 10/2005 | Hastings et al. | |
| 2006/0024732 A1 | 2/2006 | Huang et al. | |
| 2006/0035240 A1 | 2/2006 | Seul et al. | |
| 2006/0275799 A1 | 12/2006 | Banerjee et al. | |
| 2007/0031877 A1 | 2/2007 | Stahler et al. | |
| 2007/0231810 A1 | 10/2007 | Todd et al. | |
| 2007/0243534 A1 | 10/2007 | Seul et al. | |
| 2008/0020374 A1 | 1/2008 | Greene et al. | |
| 2008/0123089 A1 | 5/2008 | Seul et al. | |
| 2008/0200349 A1 | 8/2008 | Wu et al. | |
| 2008/0214412 A1 | 9/2008 | Stahler et al. | |
| 2008/0261205 A1 | 10/2008 | Denomme | |
| 2010/0062518 A1 | 3/2010 | Banerjee | |

FOREIGN PATENT DOCUMENTS

| | | |
|---|---|---|
| EP | 0126450 | 11/1984 |
| EP | 179039 | 4/1986 |
| EP | 246864 | 11/1987 |
| EP | 269764 | 6/1988 |
| EP | 472990 | 3/1992 |
| EP | 478319 | 4/1992 |
| EP | 0529775 | 3/1993 |
| EP | 723146 | 7/1996 |
| EP | 1394270 | 3/2004 |
| EP | 1564306 | 2/2005 |
| JP | 62265567 | 11/1987 |
| WO | WO8911101 | 5/1989 |
| WO | WO 9109141 | 6/1991 |
| WO | WO 9119023 | 12/1991 |
| WO | WO 9210092 | 6/1992 |
| WO | WO 9302360 | 2/1993 |
| WO | WO 9306121 | 4/1993 |
| WO | WO 9324517 | 12/1993 |
| WO | WO 9325563 | 12/1993 |
| WO | WO 9400810 | 1/1994 |
| WO | WO 9428028 | 9/1994 |
| WO | WO 9509248 | 4/1995 |
| WO | WO 9512608 | 5/1995 |
| WO | WO 9512808 | 5/1995 |
| WO | WO 9600148 | 1/1996 |
| WO | WO 9602558 | 2/1996 |
| WO | WO 9603212 | 2/1996 |
| WO | WO 9604547 | 2/1996 |
| WO | WO 9607917 | 3/1996 |
| WO | WO 9630392 | 10/1996 |
| WO | WO 9641011 | 12/1996 |
| WO | WO 9714028 | 4/1997 |
| WO | WO 9722720 | 6/1997 |
| WO | WO 9739151 | 10/1997 |
| WO | WO 9740383 | 10/1997 |
| WO | WO 9740385 | 10/1997 |
| WO | WO 9745559 | 12/1997 |
| WO | WO 9802752 | 1/1998 |
| WO | WO 9804950 | 2/1998 |
| WO | WO 9806007 | 2/1998 |
| WO | WO 9820153 | 5/1998 |
| WO | WO 9821593 | 5/1998 |
| WO | WO 9838334 | 9/1998 |
| WO | WO 9840726 | 9/1998 |
| WO | WO 9853093 | 11/1998 |
| WO | WO 9909217 | 2/1999 |
| WO | WO 9918434 | 4/1999 |
| WO | WO 9919515 | 4/1999 |
| WO | WO 9924822 | 5/1999 |
| WO | WO 9935499 | 7/1999 |
| WO | WO 9936564 | 7/1999 |
| WO | WO 9941273 | 8/1999 |
| WO | WO 9951773 | 10/1999 |
| WO | WO 9960170 | 11/1999 |
| WO | WO 9967641 | 12/1999 |
| WO | WO 0003004 | 1/2000 |
| WO | WO 0004372 | 1/2000 |
| WO | WO 0007019 | 2/2000 |
| WO | WO 0013004 | 3/2000 |
| WO | WO 0020593 | 4/2000 |
| WO | WO 0022172 | 4/2000 |
| WO | WO 0026920 | 5/2000 |
| WO | WO 0031356 | 6/2000 |
| WO | WO 0039587 | 7/2000 |
| WO | WO 0046602 | 8/2000 |
| WO | WO 0051058 | 8/2000 |
| WO | WO 0062048 | 10/2000 |
| WO | WO 0073777 | 12/2000 |
| WO | WO 0075373 | 12/2000 |
| WO | WO 0101184 | 1/2001 |
| WO | WO 0120179 | 3/2001 |
| WO | WO 0136679 | 5/2001 |
| WO | WO 0154813 | 8/2001 |
| WO | WO 0156216 | 8/2001 |
| WO | WO0159153 | 8/2001 |
| WO | WO 0184150 | 11/2001 |
| WO | WO 0188535 | 11/2001 |
| WO | WO 0194947 | 12/2001 |
| WO | WO 0198765 | 12/2001 |
| WO | WO 0212888 | 2/2002 |
| WO | WO 0214864 | 2/2002 |
| WO | WO 0231182 | 4/2002 |
| WO | WO 0233084 | 4/2002 |
| WO | WO 0235441 | 5/2002 |
| WO | WO 0237209 | 5/2002 |
| WO | WO02057496 | 7/2002 |
| WO | WO02058379 | 7/2002 |
| WO | WO 02058379 | 7/2002 |
| WO | WO 02061121 | 8/2002 |
| WO | WO02061121 | 8/2002 |
| WO | WO 02079490 | 10/2002 |
| WO | WO 02084285 | 10/2002 |
| WO | WO 02096979 | 12/2002 |
| WO | WO 03020968 | 3/2003 |
| WO | WO 03025011 | 3/2003 |
| WO | WO 03034029 | 4/2003 |
| WO | WO 03058196 | 7/2003 |
| WO | WO 03079401 | 9/2003 |
| WO | WO 03092546 | 11/2003 |
| WO | WO 2004035426 | 4/2004 |
| WO | WO 2005000236 | 1/2005 |
| WO | WO 2005042763 | 5/2005 |
| WO | WO 2005045059 | 5/2005 |
| WO | WO 2005095650 | 10/2005 |
| WO | WO 2008040257 | 4/2008 |
| WO | WO 2009088893 | 7/2009 |
| WO | WO 2010025002 | 3/2010 |
| WO | WO2010026038 | 3/2010 |
| WO | WO2010098765 | 9/2010 |
| WO | WO 2010143678 | 12/2010 |

OTHER PUBLICATIONS

Houghton. "General method for the rapid solid-phase synthesis of large numbers of peptides: specificity of anitgen-antibody interaction at the level of individual amino acids". Proc. Natl. Avad. Sci. USA. vol. 82:5131-5135 (1985).

Huff et al., "Technical Milestone: Development of the Logical Observation Identifier Names and Codes (LOINC) Vocabulary". JAIMA, vol. 5, pp. 276-292 (1998).

Iannone, Marie A., et al., "Multiplexed Single Nucleotide Polymorphism Genotyping by Oligonucleotide Ligation and Flow Cytometry". Cytometry, vol. 39, Issue 2, pp. 131-140 (Feb. 17, 2000).

Ide et al., "Synthesis and damage specificity of a novel probe for the detection of abasic sites in DNA". Biochemistry. vol. 32: 8276-8283 (1993).

Ito, Y., et al., "Patterned Immobilization of Thermoresponsive Polymer", Langmuir, vol. 13, pp. 2756-2759 (1997).

Jackman, R. J., et al., "Using Elastomeric Membranes as Dry Resists and for Dry Lift-Off", Langmuir, vol. 15, pp. 2973-2984 (1999).

Jeon, N. L., et al., "Patterned polymer growth on silicon surfaces using microcontact printing and surface-initiated polymerization", Applied Physics Letters, vol. 75, No. 26, pp. 4201-4203 (1999).

John C. Guatelli et al., "Isothermal, in vitro amplification of nucleic acids by a multienzyme reaction modeled after retroviral replication, "Proc. Nat'l Academy of Science USA, vol. 87: pp. 1874-1878 (1990).

Johnson, K. L., et al., "Surface Energy and the Contact of Elastic Solids". Proceedings of the Royal Society of London, Series A, Mathematical and Physical Sciences, vol. 324, No. 1558, pp. 301-313 (Sep. 8, 1971).

Jones et al., "Constraint, Optimization, and Hierarchy: Reviewing Stereoscopic Correspondence of Complex Features". Computer Vision and Image Understanding, vol. 65, No. 1, pp. 57-78 (1997).

Jones et al., "Dielectrophoretic liquid actuation and nanodroplet formation", Journal of Applied Physics, vol. 89, No. 2, pp. 1441-1448 (Jan. 15, 2001).

Kakabakos et al. "Immobilization of Immunoglobulins onto Surface-treated and Untreated Polystyrene Beads for Radioimmunoassays" Clin. Chem. 36 (1990), 492-496.

Kalinina, O., et al., "A core-shell Approach to Producing 3D Polymer Nanocomposites", Macromolecules, vol. 32, pp. 4122-4129 (1999).

Kamholz, et al., "Optical measurement of transverse molecular diffusion in a microchannel". Biophysical Journal, vol. 80, pp. 1967-1972 (2001).

Kamm, R. C., et al. "Nucleic Acid Concentrations in Normal Human Plasma". Clinical Chemistry, vol. 18, pp. 519-522 (1972).

Kandimalla et al., "Cyclicons" as Hybridization-Based Fluorescent Primer-Probes: Bioorganic & Medicinal Chemistry 8 (2000) 1911 to 1916 .

Kelly, J.J., et al., "Radical-generating coordination complexes as tools for rapid and effective fragmentation and fluorescent labeling of nucleic acids for microchip hybridization". Analytical Biochemisty, vol. 311, No. 2, pp. 103-118 (Dec. 15, 2002).

Klintschar, et al., "Genetic variation at the STR loci D125391 and CSF1PO in four populations from Austria, Italy, Egypt and Yemen". Forensic Sci. Int. vol. 97:37-45 (1998).

Kim, E., et al., "Polymer microstructures formed by moulding in capillaries", Nature, vol. 376, pp. 581-584 (1995).

Koch et al., "PNA-Peptide Chimerae". Tetrahedron Letters, vol. 36, pp. 6933-6936 (1995).

Koh, et al., "Molding of Hydrogel Microstructures to Create Multiphenotype Cell Microarrays". Analytical Chemistry (2003).

Koh, et al., "Poly(ethylene glycol) Hydrogel Microstructures Encapsulating Living Cells". Langmuir, vol. 18, pp. 2459-2462 (2002).

Kolch. "Meaningful Relationships: The Regulation of the Ras/Raf/MEK/ERK pathway by protein interactions". Biochem J, vol. 351, pp. 289-305 (2000).

Kotov, N., et al., "Layer-by-Layer Self-Assembly of Polyelectrolyte-Semicondictor Nanoparticle Composite Films". J. Phy Chem, vol. 99, pp. 13065-13069 (1995).

Krausa et al. "A Comprehensive PCR-ssP typing system for identification of HLA-A locus alleles", Tissue Antigens, 47 (3):237-244 (1996).

Krsko, P., et al., "Electron-Beam Surface Patterned Poly(ethylene glycol) Microhydrogels". Langmuir, vol. 19, pp. 5618-5625 (2003).

Krutzik P.O. et al., "Fluorescent cell barcoding in flow cytometry allows high-throughput drug screening and signal profiling". Nature Methods, vol. 3, No. 5, pp. 361-368 (2006).

Kubo et al., "A Novel Sensitive and specific assay for abasic sites, the most commonly produced DNA lesion". Biochemistry, vol. 13:3703-3708 (1992).

Kumacheva, E., et al., "Three-dimensional Arrays in Polymer Nanocompositites", Advanced Materials, vol. 11, No. 3, pp. 231-234 (1999).

Kurita-Ochiai, T., et al., "Butyric Acid-Induced T-Cell Apoptosis is Mediated by Caspase-8 and -9 Activation in a Fas-Independent Manner", Clinical and Diagnostic Laboratory Immunology, vol. 8, No. 2, pp. 325-332 (2001).

Vorlop, K. D., et al., "Entrapment of Microbial Cells within Polyurethane Hydrogel Beads with the Advantage of Low Toxicity", Biotechnology Techniques, vol. 6, No. 6, pp. 483-488 (1992).

Kwoh et al., "Transcription based amplification system and detection of amplified human immunodeficiency virus type 1 with a bead-based sandwich hybridization format". Proc. Natl. Acad. Sci, vol. 86, pp. 1173-1177 (Feb. 1989).

LaForge, K. S., et al., "Detection of Single Nucleotide Polymorphisms of the Human Mu Opioid Receptor Gene by Hybridization of Single Nucleotide Extension on Custom Oligonucleotide Gelpad Microchips: Potential in Studies of Addiction". American Journal of Medical Genetics (Neuropsychiatric Genetics), vol. 96, pp. 604-615 (2000).

Lagerholm et al., "Theory for Ligand Rebinding at Cell Membrane Surfaces," Biophysical Journal (1998), vol. 74, pp. 1215-1228.

Lamb, D. J., et al., "Modification of Natural and Artificial Polymer Colloids by Topology-Controlled Emulsion Polymerization". Biomacromolecules, vol. 2, No. 2, pp. 518-525 (2001).

Lander, E. S. "The New Genomics: Global Views of Biology". Sciences, vol. 274, No. 5287, pp. 536-539 (Oct. 25, 1996).

Lander, E. S., et al., "Array of Hope". Nature Genetics Supplement, Perspective, vol. 21, pp. 3-4, (Jan. 1999).

Latour, P., et al., "Polymorphic Short Tandem Repeats for Diagnosis of the Charot-Marie-Tooth IA Duplication". Clinical Chemistry, vol. 47, pp. 829-837 (2001).

Lau, F. Y., et al., "Provision of phenotype-matched blood units: no need for pre-transfusion antibody screening", Haematologica, vol. 86, No. 7, Jul. 2001, pp. 742-748.

Lee et al. "Quantitation of residual WBCs in filtered blood components by high-throughput, real time kinetic PCR", Blood Components, transfusion, vol. 42, pp. 87-93 (Jan. 2002).

Lee, et al., "Combination of Insulin-like Growth FActor (IGF)-1 and IGF-Binding Protein-1 Promotes Fibroblast-Embedded Collagen Gel Contraction". Endocrinology, vol. 137, pp. 5278-5283 (1996).

Lee, H. J., et al., "Fabricating RNA Microarrays with RNA-DNA Surface Ligation Chemistry". Analytical Chemistry, vol. 77, No. 23, pp. 7832-7837 (Dec. 1, 2005).

Lee, S., et al., "Control of Core-Shell Latex Morphology". Polymer Latexes, ACS Symposium, American Chemical Society, pp. 234-253 (1992).

Lemieux: "high throughput single nucleotide polymorphism genotyping technology" Current Genomics. vol. 1:301-311 (2000).

Lhomme et al. "Abasic DNA structure, reactivity and recognition". Biopolymers. vol. 52: 65-83 (1999).

Li, A., et al., "Multiplexed analysis of polymorphisms in the HLA gene complex using bead array chips". Tissue Anitigens, vol. 63, pp. 518-528 (2004).

Liang L., et al., "Preparation of Composite-Crosslinked Poly(N-isopropylacrylamide) Gel Layer and Characteristics of Reverse Hydrophilic-Hydrophobic Surface", Journal of Applied Polymer Science, vol. 72, pp. 1-11 (1999).

Liang, L., et al., "Temperature-sensitive membranes prepared by UV photopolymerization of N-isoproprylacrylamide on a surface of porous hydrophilic polypropylene membranes", Journal of Membrane Science, vol. 162, pp. 235-246 (1999).

Liebert, M. R., et al., "Dynamics of the holes in human erythrocyte membrane ghosts". J. Biological Chemistry, vol. 257, No. 19, pp. 11660-11666 (1982).

Lin et al. "Raman Studies of Bovine Serum Albumin". Biopolymers 15:203-218 (1976).

Lindahl et al., "Rate of depuriniation of native deoxyribonucleic acid". Biochemistry. vol. 11, No. 19: 3610-1617 (1972).

Lindahl et al., "Rate of chain breakage at apurinic sites in double-stranded deoxyribonclueic acid" Biochemistry, vol. 11, No. 19:3618-3623 (1972).

Lipshutz, R. J., et al., "High Density Synthetic Oligonucleotide Arrays". vol. 21, pp. 20-24 (Jan. 1999).

Liu, V, et al, "Three-Dimensional Photopatterning of Hydrogels Containing Living Cell". Biomedical Microdevices, vol. 4, No. 4, pp. 257-266 (2002).

Lofas, et al., "Methods for site controlled coupling to carboxymethyldextran surfaces in surface plasmon resonance sensors". Biosensors & Bioelectronics, vol. 10, pp. 813-822 (1995).

Loomans, E., et al., "Assessment of the functional affinity constant of monoclonal antibodies using an improved enzyme-linked immunosorbent assay". Journal of Immunological Methods, vol. 184, pp. 207-217 (1995).

Ye et al., "Fluorescent Microsphere-Based Readout Technology for Multiplexed Human Single Nucleotide Polymorphism Analysis and Bacterial Identification" Human Mutation, Apr. 17, 2001 (4); 305-16).

Lund et al. Assessment of Methods for Covalent Bonding of Nucleic Acids to Magnetib Beads, Bynabeads, and the Characteristics of the Bound Nucleic Acids in Hybridization Reactions, Nucleic Acids REsearch vol. 16, No. 22, 10861-10880 (1988).

Luo et al., "Emulsion Copolymerization of Butyl Acrylate with Cationic Monomer Using Interfacial Redox Initiator System". Journal of Polymer Science, vol. 39, pp. 2696-2709 (2001).

Lvov, Y, et al., "Alernate Assembly of Ordered Multilayers of SiO2 and Other Nanoparticles and Polyions". Langmuir, vol. 13, pp. 6195-6203 (1997).

Maldonado-Rodriguez et al., "Hybridization of glass-tethered oligonucleotide probes to . . . ", Molecular Biotechnology, vol. 11, No. 1, pp. 1-12 (1999).

Marras et al., Multiplex detection of single-nucleotide variations using molecular beacons: Genetic Analysis: Biomolecular Engineering 14 (1999) 151-156.

Martin, M., et al. "A Method for Using Serum or Plasma as a Source of DNA for HLA Typing". Human Immunology, vol. 33, pp. 108-113 (1992).

Martinell, J. et al., "Three mouse models of human thalassemia", Proc. Natl. Acad. Sci, USA. Aug. 1981, vol. 78, No. 8, pp. 5056-5060 (see especially p. 5057, col. 1, last paragraph, Figure 4, and the legend to Figure 4.

Maskos, U. et al., "Parallel analysis of oligodeoxyribonucleotide (oligonucleotide) interactions. I. Analysis of factors influencing oligonucleotide duplex formation". Nucleic Acids Research, vol. 20, No. 7, pp. 1675-1678 (1992).

Maskos, U., et al., "Oligonucleotide hybridisations on glass supports: a novel linker for oligonucleoptide synthesis and hybridisation properties of oligonucleotides synthesized in situ". Nucleic Acids Research, vol. 20, No. 7, pp. 1679-1684 (1992).

Maxam et al., "A new method for sequencing DNA," Proc. Natl. Acad. Sci. USA. vol. 74, No. 2, pp. 560-564, Feb. 1977.

McCloskey, et al., "Magnetic Cell Separation: Characterization of Magnetophoretic Mobility". Anal. Chem., vol. 75, pp. 6868-6874 (2003).

McCloskey, et al., "Magnetophoretic Mobilities Correlate to Antibody Binidng Capacities". Cytometry, vol. 40, pp. 307-315 (2000).

Mei et al. "Genome-wide Detection of Allelic Imbalance Using Human SNPs and High-Density DNA Arrays". Genome Research. vol. 10, pp. 1126-1137 (2000).

Michael, et al., "Randomly ordered addressable high-density optical ssensor arrays". Anal. Chem, vol. 70, pp. 1242-1248 (1999).

Micheletto et al., "A simple method for the production of a two-dimensional ordered array of small latex particles". Langmuir, vol. 11, pp. 3333-3336 (1995).

Moller, E., et al., "The Use of Magnetic Beads Coated with Soluble HLA Class I or Class II Proteins in Antibody Screening and for Specificity Determination of Donor-Reactive Antibodies". Transplantation, vol. 61, No. 10, pp. 1539-1545 (May 27, 1996).

Moore, et al., "The use of magnetite-doped polymeric microspheres in calibrating cell tracking velocimetry". J. Biochem. Biophys. Methods, vol. 44, pp. 115-130 (2000).

Morag et al. "Immobilized nitro-avidin and nitro-streptavidin as reusable affinity matrices for application in avidin-biotin technology". Analytical Biochemistry. vol. 243: 257-263 (1996).

Mori, et al., Computer program to predict liklihood of finding an HLA-matched donor: Methodology, validation, and application. Biology of Blood and Marrow Transplantation, vol. 2, pp. 134-144 (1996).

Muller et al., "Gene and Haplotype Frequencies for the Loci HLA-A, HLB-B, and HLA-DR Based on Over 13,000 German Blood Donors". Human Immunology, 2003, 64: 137-151.

Mullis et al. Specific Synthesis of DNA in Vitro via a Polymerase-Catalyzed Chain Reaction Methods In Enzymology, 1987; vol. 155, pp. 335-350.

Nagarajan et al., "Identifying Spots in Microarray Images", IEEE Transactions on Nanobioscience, vol. 1, No. 2, pp. 78-84 (Jun. 2002).

Nagayama et al., "Fabrication of two-dimensional colloidal arrays". Phase Transitions, vol. 45, 185-203 (1993).

Nam, J., et a., "Colorimetric Bio-Barcode Amplification Assay for Cytokines". Anal. Chem., vol. 77, pp. 6985-6988 (2005).

Nau et al., "A Command Processor for the Determination of Specificities fro Matrices of Reactions Between Blood Cells and Antisera". Computers and Biomedical Research, vol. 10, pp. 259-269 (1977).

Niemeyer et al., "DNA-directed Immobilization: Efficient, Reversible, and Site-Selective Surface Binding of Proteins by means of Covalent Stretavidin Conjugates". Analytical Biochemistry, vol. 268, pp. 54-63 (1999).

Niemeyer et al., "Oligonucleotide-directed self-assembly of proteins: semisynthetic DNA—streptavidin hybrid molecules as connectors for the generation of macroscopic arrays and the construction of supramolecular bioconjugates". Nucleic Acids Research, vol. 22, pp. 5530-5539 (1994).

Nygren, "Molecular Diagnostics of Infectious Diseases" Royal Institute of Technology Department of Biotechnology, Stockholm 2000, pp. 1-68.

Ohlmeyer, M. H. J. et al. "Complex Synthetic Chemical Libraries Indexed with Molecular Tags". Proceedings of the National Academy of Sciences, USA, National Academy of Science, Washington DC. vol. 90, Dec. 1, 1993, pp. 10922-10926.

Okubo, and Yamashita. "Thermodynamics for the preparation of micorn-sized, monodispersed highly monomer-'absorbed' polymer particles utilizing the dynamic swelling method." Colloids and Surfaces, 1999:153-159.

Okubo et al., "Preparation of micron-size monodisperse polymer particles by seeded polymerization utilizing the dynamic monomer swelling method". Colloid and Polymer Science, vol. 269, No. 3, pp. 222-226 (1991).

Olejnik et al., "Photocleavable biotin phosphoramidite for 5'-end-labeling, purification & phosphorylation of oligonucleotides", Nucleic Acids Research 1996, vol. 24, 2:361-366.

Oliver, D., et al, "Use of Single Nucleotide Polymorphisms (SNP) and Real-Time Polymerase Chain Reaction for Bone Marrow Engraftment Analysis". Journal of Molecular Diagnostics, vol. 2, No. 4, pp. 202-208 (Nov. 2000).

Olson et al. "A common langauage for physical mapping of the human genome". Science, vol. 245, pp. 1434-1435 (1989).

Otero, T. F., et al., "Electrochemically initiated acrylic acid/acrylamide copolymerization", J. Electroanal. Chem., vol. 256, pp. 433-439 (1998).

Otero, T. F., et al., "Electroinitiated polymerization of acrylamide in DMG: Attempts at an interfacial model", J. Electroanal. Chem., vol. 304, pp. 153-170 (1991).

Pastinen, et al., "A System for specific, high-throughput genotyping by allele-specific primer extension on microarrays". Genome Res., vol. 10, pp. 1031-1042 (2000).

Peter, C., et al., "Optical DNA-sensor chip for real-time detection of hybridization events". Fresenius J. Anal. Chem, vol. 371, pp. 120-127 (Jun. 2001); Published online Springer-Verlay 2001.

Wilson, M. R., et al., "A New Microsphere-based Immunofluorescence Assay for Antibodies to Membrane-associated Antigens". Journal of Immunological Methods, vol. 107, pp. 231-237 (1988).

Peterson, et al. "Fiber Optic pH probe for physiological use". Anal. Chem. vol. 52, 864-869 (1980).

Peterson, et al., "Fiber Optic Sensors for Biomedical Applications". Science, vol. 13; pp. 123-127 (1984).

Peytavi et al., "Correlation between microarray DNA hybridization efficiency and the position of short capture probe on the target nucleic acid". Biotechniques, vol. 39, No. 1, pp. 89-96 (2005).

Pooga, M., et al., "Cell-Penetrating constructs regulate galanin receptor levels and modify pain transmission in vivo" Nature Biotechnology, vol. 16, pp. 857-861 (1998).

Pope. "Fiber optic chemical microsensors employing optically active silica microspheres". SPIE, vol. 2388; pp. 245-256 (1995).

Prati D. et al., DNA Enzyme Immunoassay of the PCR-Amplified HLA-DQ Alpha Gene for Estimating Residual Leukocytes in Filtered Blood Clincial and Diagnostic Laboratory Immunology, Mar. 1995, p. 182-185.

Pregibon et al, "Magnetically and Biologically Active Bead-Patterned Hydrogels". Langmuir, vol. 22, pp. 5122-5128 (2006).

Proudinikov et al., "Chemical methods of DNA and RNA fluorescent labeling". Nucleic Acids Research. vol. 24, No. 22: 4535-4542 (1996).

Proudnikov, D., et al., "Immobilization of DNA in Polyacrimide Gel for the Manufacture of DNA and DNA-Oligonucleotide Microchips", Analytical Biochemistry, vol. 259, pp. 34-41 (1998).

Quon, R., et al., "Measurement of the Deformation and Adhesion of Rough Solids in Contact". J. Phys. Chem., vol. 103, pp. 5320-5327 (1999).

Rabbany et al., "Assessment of hetrogeneity in antibody displacement reactions". Anal Chem, vol. 69, pp. 175-182 (1997).

Radtchecnko et al., "Core-shell structures formed by the solvent-controlled precipitation of luminescent ScTe nanocrystals on latex spheres". Advanced Materials, vol. 13, No. 22, pp. 1684-1687 (2001).

Ramsay, G., "DNA Chips: State-of-the-Art". Nature Biotechnology, vol. 16, pp. 40-44 (Jan. 1998).

Reddy et al., "Determination of the Magnetic Susceptibility of Labeled Particles by Video Imaging". Chemical Engineering Science, vol. 51, No. 6, pp. 947-956 (1996).

Reid M.E., et al., "Novel Dombrock blood group genetic variants . . . ", Blood (ASH Annual Meeting Abstract) 2004, 104: Abstract 383.

Relogio, A. et al., "Optimization of oligonucleotide-based DNA microarrays", Nucl. Acids Res., vol. 30, e51, pp. 1-10 (2002).

Richardson et al., "The use of coated paramagnetic particles as a physical label in a magneto-immunassay". Biosensors & Bioelectronics, vol. 16, pp. 989-993 (2001).

Richardson, et al., "A novel measuring system for the determination of paramagnetic particle lables for use in magneto-immunoassays". Biosensors & Bioelectronics, vol. 16, pp. 1127-1132 (2001).

Richetti et al., "Two-dimensional aggregations and crystallization of a colloidal suspension of latex spjeres", J. Physique Letter. vol. 45, pp. L-1137 to L-1143 (1984).

Righetti, P. G., et al., "Electrophoresis gel media: the state of the art", J. Chromatogr B., Biomed Sci Appl, vol. 699, No. 1-2, pp. 63-75 (Oct. 10, 1997).

Roberts et al. "Patterned magnetic bar array for high-thoughput DNA detection" IEEE Transaction on Magnetics. vol. 40, No. 4: 3006-3008 (2004).

Rubina et al, "Hydrogel drop microchips with immobilized DNA: properties and methods for large-scale production". Analytical Biochemistry, vol. 325, pp. 92-106 (2004).

Rudzinski, et al., "pH-sensitive acrylic-based copolymeric hydrogels for the controlled release of a pesticide and a micronutrient". Journal of Applied Polymer Science, vol. 87, pp. 394-403 (2003).

Sacchetti, et al. "Efficiency of Two Different Nine-Loci Short Tandem Repeat Systems for DNA Typing Purposes". Clinical Chemistry, vol. 45, No. 2, pp. 178-183 (1999).

Saito, K., et al., "Detection of Human Serum Tumor Necrosis Factor-alpha in Healthy Donors, Using a Highly Sensitive Immuno-PCR Assay". Clinical Chemistry, vol. 45, No. 5, pp. 665-669 (1999).

Sambrook et al., "Precipitation with Ethanol or Isopropanol", Concentrating Nucleic Aicds, Molecular Cloning vol. 3, pp. E3-E4 and E.10-E.15 (1989).

Sano, T, et al., "Immuno-PCR: Very Senisitive Antigen Detection by Means of Specific Antibody-DNA Conjugates". Science, vol. 258, pp. 120-122 (Oct. 2, 1992).

Santa Lucia, J. Jr., "A unified view of polymer, dumbbell, and oligonucleotide DNA nearest-neighbor thermodynamics". PNAS USA, vol. 95, pp. 1460-1465 (1998).

Schaid et al., "Score Tests for Association between traits and Haplotypes when Linkage Phase is Ambiguous", American Journal of Genetics. vol. 70, pp. 425-434 (2002).

Schena et al., "Quantitative Monitoring of Gene Expression Patterns with a Complementary DA Microarray". Science, vol. 270, pp. 467-470 (1995).

Schreiber, G. B., et al., "Increasing Blood Availability by changing Donation Patterns". Transfusion, vol. 43, pp. 591-597 (2003).

Schreuder et al., "The HLA Dictionary 1999: A Summary of HLA-A, B, C, DRB1/3/4/5, DOB1 alleles and their association with serologically defined HLA-A, B, C, DR and DQ antigens", Tissue Antigens 54: 409-437 (1999).

Schumaker, et al., "Mutation Detection by solid phase primer extension", Human Mutation 7:346-354 (1996).

Wilson et al., "A generalized method for magnetite nanoparticle steric stabilization utilizing block copolymers containing carboxylic acids". European Cells and Materials, vol. 2, Suppl 2, pp. 202-209 (2002).

Schuster et al. "Allele-specific and asymetric polymerase chain reacton amplification in combination: a one step polymerase chain protocol for rapid diagnosis of familial defective apolipoprotein B-100", Anal Biochem. Jul. 1992; 204 (1):22-5).

Scillian, James J., et al., "Early Detection of Antibodies Against rDNA-Produced HIV Proteins with a Flow Cytometric Assay". Clinical Chemistry, vol. 40, No. 3, pp. 420-425 (1994).

S. Ebel et al. "Very Stable Mismatch Duplexes: Structural and Thermodynamic Studies on G-A Mismatches in DNA" Biochemistry 31:12083-86 (1992).

Seeman, P., et al., "Structure of Membrane Holes in Osmotic and Saponin Hemolysis"; The Journal of Cell Biology, vol. 56; pp. 519-527 (1973).

Sehgal et al. "A method for the high effieiency of water-soluble carbodiimide-mediated amidation". Analytical Biochemistry. vol. 218:87-91 (1994).

Seltsam, et al., Systematic analysis of the ABO gene diversity within exons 6 and 7 by PCR screening reveals new ABO alleles, Transfusion, vol. 43, pp. 428-439 (2003).

Sennerfors, T., et al., "Adsorption of Polyelectrolyte-Nanoparticle Systems on Silica: Influence of Ionic Strength". Journal of Colloid and Interface Science, vol. 254, pp. 222-226 (2002).

Serizawa, T., et al., "Electrostatic Adsorption of Polystyrene Nanospheres onto the Surface of an Ultrathin Polymer Film prepared by Using an Alternate Adsorption Technique". Langmuir, vol. 14, pp. 4088-4094 (1998).

Sethu, P; "Microfluidic diffusive filter for apheresis (leukopheresis)"; Lab Chip, vol. 6, No. 1, pp. 83-89 (Jan. 2006); Published electronically Nov. 11, 2005.

Seul et al., "Domain Shapes and Patterns: The Phenomenology of Modulated Phases". Science, vol. 267:476-483 (1995).

Seul et al., "Scale transformation of magnetic bubble arrays: coupling of topological disorder and polydispersity". Science, vol. 262: 558-560 (1993).

Sgaramella, V., et al., "Total Synthesis of the Structural Gene for an Alanine Transfer RNA from Yeast. Enzymic Joining of the Chemically Synthesized Polydeoxynucleotides to form the DNA Duplex Representing Nucleotide Sequence 1 to 20". J. Mol. Biology, vol. 72, pp. 427-444 (1972).

Sham, P. et al., "Haplotype Association of Discrete and Continuous Traits Using Mixture of Regression Models", Behavior Genetics, Mar. 2004, 34(2), pp. 207-214.

Shevkoplyas, S., et al., "Biomimetic autoseparation of leukocytes from whole blood in a microfluidic device"; American Chemical Society; vol. 77, No. 3, pp. 933-937 (Feb. 1, 2005).

Shon. "Application Note—New Best Practices for Biosample Management: Moving Beyond Freezers". American Biotechnology Laboratory, vol. 23, No. 2, pp. 10-13 (2005).

Shoyer, Terrie W., et al., "A Rapid Flow Cytometry Assay for HLA Antibody Detection Using a Pooled Cell Panel Convering 14 Serological Crossreacting Groups". Transplantation, vol. 59, No. 4, pp. 626-630 (1995).

Siegel, D., "Phage display-based molecular methods in immunohematology". Transfusion, vol. 47, pp. 89S-94S (Jul. 2007 Supplement).

Simon, R. "Application of optimization methods to the hematological support of patients with disseminated malignacies", Mathematical Biosciences, vol. 25, 1975, pp. 125-138.

Skolnick et al. "Simultaneous analysis of multiple polymorphic loci using amplified sequence polymorphisms (ASPs)". Genomics, vol. 2, pp. 273-279 (1988).

Smay, J., et al., "Colloidal Inks for Directed Assembly of 3-D Peridoic Structures". Langmuir, vol. 18, pp. 5429-5437 (2002).

Smith, J. W., et al., "RED: A Red-Cell Antibody Identification Expert Module". Journal of Medical Systems, vol. 9, No. 3, pp. 121-138 (1985).

Southern E. M., "DNA Fingerprinting by hybridisation to oligonucleotide arrays". Electrophoresis, vol. 16, No. 9, pp. 1539-1542 (1995).

Southern, E. M., et al., "Analyzing and comparing nucleic acid sequences by hybridization to arrays of oligonucleotides: evaluation using experimental models". vol. 13, No. 4, pp. 1008-1017 (Aug. 1992).

St. Louis, M, et al., "The Dombrock blood group system: A Review", Transfusion 43: 1126-1132 (2003).

Steemers, F.J. (2000) Screening unlabeled DNA targets with randomly ordered fiber-optic gene arrays. Nat. Biotechnol., 18, 91-94.

Stemmer, C., et al., "Use of Magnetic Beads for Plasma Cell-free DNA Extraction: Toward Automation of Plasma DNA Analysis for Molecular Diagnostics". Clinical Chemistry, vol. 49, No. 11, pp. 1953-1955 (2003).

Stevens, P. W., et al. "Imaging and Analysis of Immobilized Particle Arrays". Analytical Chemistry. vol. 75, pp. 1147-1154 (2003).

Storry et al, "Genetic Basis of blood group diversity". British Journal of Haematology, vol. 126, pp. 759-771 (2004).

Strobel E., et al., "The molecular basis of Rhesus antigen E", Transfusion 44:407-409 (2004).

Sukhishvilli, S.A. et al. "Adsorption of human serum albumin: Dependence on molecular architecture of the oppositely charged surface" J. Chem. Phys. 110, 10153-10161 (1999).

Sun et al., "Continuous, Flow-Through Immunomagnetic Cell Sorting in a Quadrupole Field". Cytometry, vol. 33, pp. 469-475 (1998).

Suzawa et al., "Adsorption of Plasma Proteins onto Polymer Latices". Advances in Colloid and Interface Science, vol. 35, pp. 139-172 (1991).

Svitel, et al., "Combined Affinity and Rate Constant Distributions of Ligand Populations from Experimental Surface Bindinh Kinetics and Equilibria". Biophysical Journal, vol. 84, pp. 4062-4077 (Jun. 2003).

Syvanen, "From Gels to Chips: Minisequencing Primer Extensions for Analysis of Pont Mutations and Single Nucleotide Polymorphisms", Human Mutation 13:1-10 (1999).

Syvanen, A., et al., "Identification of Individuals by Analysis of Biallelic DNA Markers, Using PCR and Solid-Phase Minisequencing". Am. J. Hum. Genet, vol. 52, pp. 46-59 (1993).

Syvannen, A. "Toward genone-wide SNP genotyping". Nature Genetics Supplement. vol. 37: s5-s10 (2005).

Sze. MIS Diode and Charge-Coupled Device. The Physics of Semiconductors, Chapter 7, pp. 362-430 (2nd Edition) (1981).

Takeda et al. "Conformational Change of Bovine Serum Albumin by Heat Treatment", J. Protein Chemistry 8:653-659, No. 5 (1989).

Tanaka, T., et al., "Mechanical instability of gels at the phase transition", Nature, vol. 325, pp. 796-798 (1987).

Taniguchi et al. "Adsorption/desorption behavior and covalent grafting of an antibody onto cationic amino-functionalized poly(styrene-N-isoprapylacrylamide) core-shell latex particles". Colloids and Surfaces B: Biointerfaces. vol. 29: 53-65 (2003).

Tarnok et al., "Cytometric Bead Array to Measure Six Cytokines in Twenty-Five Microliters of Serum," Clinical Chemistry, (2003), vol. 49, No. 6, pp. 1000-1002.

Taylor et al., "Linked oligodeoxynucleotides show binding cooperativity and can selectively impair replication of deleted mitochondrial DNA templates", Nucleic Acids Research. vol. 29, No. 16, pp. 3404-3412 (2001).

Tobitani et al. "Heat-induced gelation of globular proteins. 1. Model for the effects of time and temperature onthe gelation time of BSA gels." Macromolecules. vol. 30:4845-4854 (1997).

Tokumasu F. et al., Development and application of quantum dots for immunocytochemistry of human erythrocytes, J. Microscopy, 2003, pp. 256-261, vol. 211, pt. 3.

Tonnisson et al., "Arrayed primer extension on the DNA chip; Method and applications", Microarray Biochip Technology, Biotechniques Books, 247-262 (2000).

Tsuchihashi, Z. et al. "Progress in high throughput SNP genotyping methods", The Pharmacogenomics Journal 2:103-110 (Apr. 2002).

Trau et al., "Field-induced layering of colloidal crystal", Science, vol. 272; pp. 706-709 (1996).

Trang D.T.X. et al. "One step concentration of malarial parasite-infected red blood cells and removal of contaminating white blood cells", Malaria Journal (2004) pp. 1-7 from http://www.malariajournal.com/content/3/1/7.

Trau et al., "Nanoencapsulated microcrystalline particles for superamplified biochemical assays". Anal. Chem, vol. 74, No. 21, pp. 5480-5486. Web Release Date: Sep. 25, 2002.

Turcanu et al, "Cell Identification and isolation on the basis of cytokine. secretion: A novel tool for investigating immune responses". Nature Medicine, vol. 7, No. 3, pp. 373-376 (Mar. 2001).

Tyagi et al., Molecular Beacons: Probes that Flouresce upon Hybridization, Nature Biotechnology vol. 14, pp. 303-308 (1996).

Vainrub, A., et al., "Sensitive quantitative nucleic acid detection using oligonucleotide microarrays". vol. 125, No. 26, pp. 7798-7799, (Jul. 2, 2003).

Van Kempen, et al., "Mean and Variance of Ratio Estimators Used in Fluorescence Ratio Imaging". Cytometry, vol. 39, pp. 300-305 (2000).

Van Zoelen, "Receptor-ligan interaction: a new method for determing binding parameters without a priori assumptions on non-specific binding". Biochem J., vol. 262, pp. 549-556 (1989).

Vasiliskov, A. V., et al., "Fabrication of Microarray of Gel-Immobilized Compounds on a Chip by Copolymerization". BioTechniques, vol. 27, pp. 592-606 (Sep. 1999).

Vaynberg et al. "Structure and extent of absorbed gelatin on acrylic latex and polystyrene collodial particles". Journal of Colloid and Interface Science. vol. 205:131-140 (1998).

Vet, J.A.M. (1999) Multiplex detection of four pathogenic retroviruses using molecular beacon. Proc. Natl. Acad. Sci. USA, 96, 6394-6399.

Vilain. "CYPs, SNPs, and Molecular Diagnosis in the Postgenomic Era". Clinical Chemistry, vol. 44, pp. 2403-2404 (1998).

Wahl et al., "Efficient transfer of large DNA fragments from agarose gels to diazobenzyloxymethyl-paper and rapid hybridization by using dextran sulfate". Proc. Natl. Acad. Sci. USA. vol. 76, No. 8: 3683-3687 (1979).

Wang, D., et al, "Large-Scale Identification, Mapping, and Genotyping of Single-Nucleotide Polymorphisms in the Human Genome". Science, vol. 280, No. 5366, pp. 1077-1082 (May 15, 1998).

Warren, J. A., "Selected Spacings During Directional Solidification of a Binary Alloy", Spatio-Temporal Patterns, Ed. P. E., Cladis and P. Palffy-Muhoray, SFI Studies in the Science of Complexity, Addison-Wesley, pp. 91-105 (1995).

Weinfeld et al., "Selective hydrolysis by exo- and endonucleases of phosphodiester bonds adjacent to an apurinic site". Nucleic Acids Research, vol. 17, No. 10: 3735-3744 (1989).

Weissenbach et al. "A Second generation linkage map of the human genome". Nature, vol. 359, pp. 794-801 (1992).

Wen, et al., "Planar Magnetic Colloidal Crystals". Physical Review Letters, vol. 85, No. 25, pp. 5464-5467 (2000).

Wiedmann, M., et al., Ligase Chain Reaction (LCR)—Overview and Applications, PCR Methods and Applications, Genome Research, vol. 3, pp. s51-s64 1994).

Yeang et al. Molecular classification of multiple tumor types. Bioinformatics vol. 17 Suppl. 1, pp. s316-s322 (2001).

J.F. Chapman et al., "Working Party of the BCSH: Guidelines for compatibility procedures in blood transfusion laboratories", Transfusion Medicine, vol. 14, pp. 59-73 (2004).

Yamashita et al., "Thermodynamics for the preparation of micron-sized, monodispersed highly monomer absorbed polymer particles utilizing the dynamic selling method". Colloids and Surfaces, vol. 153, pp. 153-159 (1999).

Yao et al., "Molecular-beacon-based array for sensitive DNA analysis". Analytical Biochemistry, vol. 331, pp. 216-223 (2004).

Fukuda et al., "Noncontact manipulation of DNA molecule 1. Transportation of DNA molecule by dielectric force". Nippon Kikai Gakkai Ronbunshu, vol. 62: 2765-2772 (1996).

Armstrong et al., "Suspension arrays for high throughput, multiplexed single nucleotide polymorphism genotyping" Cytometry. vol. 40:102-108 (2000).

Bortolin, S, et al. "Analytical validation of the tag-it high-throughput microsphere-based universal arrray genotyping platform: application to the multiplex detection of a panel of thrombophilia-associated single-nucleotide polymorphisms" Clinical Chemistry, vol. 50 (11), pp. 2028-2036 (Sep. 13, 2004).

B.-Y. Ha et al., "Counterion-Mediated Attraction between Two Like-Charged Rods," Physical Review Letters, Aug. 18, 1997, vol. 79, No. 7, pp. 1289-1292.

A. Hatch, et al., "Diffusion Immunoassay in Polyacrylamide Hydrogels". Micro Total Analysis Systems, pp. 571-572 (2001).

Aho et al., "Efficient String Matching: An Aid to Bibliographic Search". Communications of the ACM, vol. 18, No. 6, pp. 333-340 (Jun. 1975).

Albergo et al., "Solvent effects on the thermodynamics of double-helix formation in (dG-sC) 3". Biochemistry, vol. 20, No. 6: 1413-1418 (1981).

Albrecht et al, "Probing the role of multicellular organization in three-dimensional microenvironments". Nature Methods, vol. 3, No. 5, pp. 369-375 (May 2006).

Albrecht et al., "Photo and electropatterning of hydrogel-encapsulated living cell arrays", Lab on a Chip, vol. 5, Issue 1, pp. 111-118 (2004).

Alford, R. L., "DNA Analysis in forensics, disease and animal/plant identification". Current Opinions in Biotechnology, vol. 5(1), pp. 29-33 (1994).

Al-Soud, W. A., "Purification and Characterization of PCR-Inhibitory Components in Blood Cells". Journal of Clinical Microbiology, vol. 39, No. 2, pp. 485-493 (Feb. 2001).

Al-Soud, W. A., et al., "Identification and characterization of immunoglobulin G in blood as a major inhibitor of diagnostic PCR". Journal of Clinical Microbiology, vol. 38, No. 1, pp. 345-350 (Jan. 2000).

Ambruso, D. R., et al., "Experience with donors matched for minor blood group antigens in patients with sickle cell anemia who are receiving chronic transfusion therapy", Transfusion, vol. 27, No. 1, 1987, pp. 94-98.

Zhang, Y., et al., "Reproducible and inexpensive probe preparation for oligonucleotide arrays". Nucleic Acids Research, vol. 29, No. 13, pp. E66-6 (Jul. 1, 2001).

Arenko, et al., "Protein microchips: Use for immunoassay and enzymatic reactions". Analytical Biochemistry, vol. 278, pp. 123-131 (2000).

Assie et al., Correlation between low/high affinity ratios for 5-HT Receptors and Intrinsic Activity, European Journal of Pharmacology, vol. 386, pp. 97-103 (1999).

Bakewell et al., "Characterization of the dielectrophoretic movement of DNA in micro-fabricated structures", Institute of Physics Conference Series (1999) Electrostatics (1999).

Balass et al. "Recovery of high-affinity phage from a Nitrostretavidin matrix in phage-display technology". Analytical Biochemistry, vol. 243: 264-269 (1996).

Baldwin, et al., "Phosphorylation of gastrin-17 by epidermal growth factor-stimulated tyrosine kinase". Nature, vol. 44, pp. 2403-2404 (1998).

Bandeira-Melo, C., et al., "EliCell: A gel-phase dual antibody capture and detection assay to measure cytokine release from eosinophils". Journal of Immunological Methods, vol. 244, pp. 105-115 (2000).

Bao, Y. P., et al., "Detection of Protein Analytes via Nanoparticle-Based Bio Bar Code Technology". Anal. Chem., vol. 78, pp. 2055-2059 (2006).

Barany, Francis, "Genetic Disease Detection and DNA Amplification using Cloned Thermostable Ligase". Proceedings of the National Academy of Sciences of the United States of America, vol. 88, pp. 189-193 (Jan. 1991).

Barnard et al. "A fibre-optic chemical sensor with descrete sensing sites". Nature, vol. 353:338-340 (1991).

Basu, S., et al., "Synthesis and Characterization of a Peptide Nucleic Acid Conjugated to a D-Peptide Analog of Insulin-like Growth Factor 1 for Increased Cellular Uptake". Bioconjugate Chem, vol. 8, No. 4, pp. 481-488 (1997).

Battersby et al., "Toward Larger Chemical Libraries: Encoding with Fluorescent Colloids in Combinatorial Chemistry". J. Amer Chem Soc, vol. 122, pp. 2138-2139 (2000).

Baumgarth N. et al., A practical approach to multicolor flow cytometry for immunophenotyping, J. Immunological Methods, 2000, pp. 77-97, vol. 243.

Bavykin, S.G., et al., "Portable system for microbial sample preparation and oligonucleotide microarray analysis". Appl. Environmental Microbiol. 67(2), 922-928 (2001).

Beatty et al. "Probability of Finding HLA-mismatched Related or Unrelated Marrow or Cord Blood Donors", Human Immunology, 2001, vol. 61, pp. 834-840.

Beebe et al., "Functional Hydrogel structures for autonomous flow control inside microfluidic channels". Nature, vol. 404, No. 6778, pp. 588-590 (Apr. 6, 2000).

Beiboer, S. W., et al., "Rapid genotyping of blood group antigens by multiplex polymerase chain reaction and DNA microarray hybridization" 45 Transfusion 667-679 (2005).

Bennett, P. R., et al., "Prenatal Determination of Fetal RhD Type by DNA Amplification". The New England Journal of Medicine, vol. 329, No. 9, pp. 607-610 (Aug. 26, 1993).

Bernard, Philip S., "Homogenous Multiplex Genotyping of Hemochromatasis Mutations with Fluorescent Hybridization Probes". American Journal of Pthology, vol. 153, No. 4, pp. 1055-1061 (1998).

Bessetti, J., "An introduction to PCT Inhibitors". Profiles in DNA-PCR Inhibition, pp. 9-10 (Mar. 2007).

Bickel, P. J., "Discussion of the Evaluation of Forensic DNA Evidence". Proc. Natl. Acad. Sci., vol. 94, p. 5497 (May 1997).

Zhang, X., et al., "Strand invasion by mixed base PNAs and a PNA-peptide chimera". Nucleic Acids Research, vol. 28, No. 17, pp. 3332-3338 (2000).

Blaaderen, et al., "Synthesis and Characterization of Colloidal Dispersions of Fluorescent, Monodisperse Silica Spheres". Langmuir, vol. 8, No. 2, pp. 2921-2931 (1992).

Bonnet, G., et al., "Thermodynamic basis of the enhanced specificity of structured DNA probes," Proc. Natl. Acad, Science, USA, vol. 96, pp. 6171-6176, May 1999.

Bos et al', "Controlled release of pharmaceutical protein from hydrogels". Business Briefing: Pharmatech, pp. 184-187 (2002).

Boyce, et al. "Peptidosteroidal Receptors for Opioid Peptides. Sequence-Selective Binding Using a Synthetic Receptor Library". J. Am. Chem. Soc., vol. 116, No. 17, pp. 7955-7956 (1994).

Boyd et al., "Tosyl Chloride activation of a rayon/polyester cloth for protein immobilization", Biotechnology Techniques, Apr. 1993, vol. 7, 4:277-282.

Braga et al., "Hydrophobic Polymer Modification with Ionic Reagents: Polysterene Staining with Water-Soluble Dyes". Langmuir, vol. 19, No. 18, pp. 7580-7586 (2003).

Breslauer, K.J. et al., "Predicting DNA duplex stability from the base sequence". PNAS USA, vol. 83, pp. 3746-3750 (1986).

Brick, et al., "Formation of Colloidal Dispersions of Organic Materials in Aqueous Media by Solvent Shifting". Langmuir, vol. 19, No. 16, pp. 6367-6380 (200.

Broude et al., "Multiplex allele-specific target amplification based on PCR suppression". PNAS. vol. 98, No. 1, pp. 206-211 (2001).

Brown, Patrick O., et al., "Exploring the new world of the genome with DNA microarrays". Nature Genetics Supplement, vol. 21, pp. 33-37 (Jan. 1999).

Buck et al., "Design Strategies and Performance of Custom DNA Sequence Primers". BioTechniques, vol. 27, pp. 528-536 (Sep. 1999).

Bunce et al., "Phototyping: Comprehensive DNA Typing for HLA-A, B, C, DRB1, DRB2, DRB3, DRB4, DRB5 & DQB1 by PCR with 144 primer mixes utilizing sequence-specific primers (PCR-SSP)". Tissue Antigens, vol. 46, No. 5, pp. 355-367 (Nov. 1995).

Bunce, M., et al., "Comprehensive serologically equivalent DNA typing for HLA-A by PCR using sequence specific primers (PCR_SSP)", Tissue Anitigens 45: 81-90 (1995).

Burbulis, I, et al., "Using protein-DNA chimeras to detect and count small numbers of molecules". Nature Methods, vol. 2, No. 1, pp. 31-37 (Jan. 2005).

Cai et al., "Flow cytometry-based minisequencing: A new platform for high-throughput single-nucleotide polymorphism scoring", Genomics 66:135-143 (2000).

Campbell, C. J., et al., "Cell Interaction Microarray for Blood Phenotyping". Analytical Chemistry, vol. 78, pp. 1930-1938 (2006).

Campian et al. Colored and fluorescent solid supports. Innovation and Perspectives in Solid Phase Synthesis. Ed: E. Birmingham (Mayflower, London), pp. 469-474 (1994).

Cao et al., "High and intermediate resolution DNA typing systems for class I HLA-A, B, C genes by hybridization with sequence-specific oligonnucleotide probes (SSOP)", Rev Immunogenetics 1:177-208 (1999).

Cao et al., "Nanoparticles with Raman Spectroscopic Fingerprints for DNA and RNA Detection", Science 197:1536-1539 (2002).

Caruso et al., "Magnetic Core-Shell Particles: Preparation of Magnetite Multilayers on Polymer Latex Microspheres". Advanced materials, vol. 11, No. 11, pp. 950-953 (1999).

Caruso, et al., "Magnetic Nanocomposite Particles and Hollow Spheres Constructed by a Sequential Layering Approach". Chem Mater, vol. 13, No. 1, pp. 109-116 (2001).

Caruso. "Nanoengineering of Particle Surfaces", Advanced Materials, vol. 12, No. 1, pp. 11-22 (2001).

Casnellie JE, et al., "Phosphorylation of synthetic peptides by a tyrosine protein kinase from the particulate fraction of a lymphoma cell line". Proc natl Sci USA, vol. 79, No. 2, pp. 282-286 (1982).

Chalmers, et al., "An instrument to determine the magnetophoretic mobility of labeled, biological cells and paramagnetic particles". Journal of Magnetism and Magnetic Materials, vol. 194, pp. 231-241 (1999).

Chan et al. (1995). The Bipophysics of DNA Hybridization with Immobilized Oligonucleotide Probes. Biophysical Journal 69:2243-2255.

Chang, et al., "New Approach to Produce monosized Polymer Microcapsules by the Solute Co-diffusion Method". Langmuir, vol. 17, No. 18, pp. 5435-5439 (2001).

Zhang et al., "Reconstruction of DNA sequencing by hybridization". Bioinformatics, vol. 19, No. 1, pp. 14-21 (2003).

Chaudhry et al., "Reactivity of human apurinic/apyrimidinic endonucleoase and Escheria coli exonucleonase III with bistranded abasic sites in DNA". The Journal of Biological Chemisty., vol. 272: 15650-15655 (1997).

Chee, M. et al., "Accessing genetic information with high-density DNA arrays". Science, vol. 274, pp. 610-613 (1996).

Chen et al., "A Microsphere-Based assay for multiplexed single nucleotide polymorphism analysis using single base chain extension", Genome Research, Cold Spring Harbor Laboratory Press 10:549-557 (2000).

Zhang et al., "Nuclear DNA analysis in genetic studies of populations; practice, problems and prospects" Molecular Ecology. vol. 12:563-584 (2003).

Chen, YX, et al., "Deletion of arginine codon 229 in the Rhce gene alters e and f but not c antigen expression". vol. 44, No. 3, pp. 391-398 (Mar. 2004).

Cheng, et al., "A Synthetic peptide derived from p34cdc2 is a Specific and Efficient Substrate of SRC-Family Tyrosine Kinases". J Biol Chem, pp. 9248-9256. vol. 267, No. 13 (1992).

Zborowski, et al., "Continuous cell separation using novel magnetic quadruple flow sorter". Journal of Magnetism and Magnetic Materials, vol. 194, pp. 224-230 (1999).

Cherepinsky, Vera, "On mathematical aspects of genomic analysis", Ph.D. Thesis, published Mar. 2004.

Cheung, V. G., et al., "Making and Reading Microarrays". vol. 21, pp. 15-19 (Jan. 1999).

Choi, et al., "An on-chip magnetic separator using spiral electromagnets with semi-encapsulated permalloy". Biosensors & Bioelectronics, vol. 16, pp. 409-416 (2001).

Yellen, B. B., et al., "Programmable Assembly of Colloidal Particles Using Magnetic Microwell Templates", Langmuir, p. est 6.5 (2004).

Clerc, P., et al., "Advanced deep reactive ion etching: a versatile tool for microelectromechanical systems". J. Micromech Microeng, vol. 8, No. 4, pp. 272-278 (Dec. 1998).

Coffer et al., "Characterization of Quantum-Confined CdS Nanocrystallites Stabilized by Deoxyribonucleic Acid (DNA)" Nanotechnology, 1992 3:69-75.

Yeh, S. R., et al., "Assembly of ordered colloidal aggregares by electric-field-induced fluid flow". Nature, Mar. 6, 1997; vol. 386, No. 6620, pp. 57-59.

Colombie, et al., "Role of Mixed Anionic-Nonionic Systems of Surfactants in the Emulsion Polymerization of Styrene: Effect on Particle Nucleation". Macromolocules, vol. 33, No. 20, pp. 7283-7291 (2001).

Cosgrove et al. "A Small-angle neutron scattering study of the structure of gelatin at the surface of polystyrene latex particles". Langmuir. vol. 14:5376-5382 (1998).

Coyne et al., "Assymetric PCR for ssDNA Production", Molecular Biology Techniques Manual. Third Edition. Jan. 1994, Feb. 2001; http://www.mcb.uct.ac.za/pcrcond.htm.

Crisp, M., et al., "Preparation of Nanoparticle Coatings on Surfaces of Complex Geometry". Nano Letters, vol. 3, No. 2, pp. 173-177 (2003).

Cronin M.T. et al., "Cystic Fibrosis Mutation Detection by Hybridization to Light-Generated DNA Probe Arrays," Human Mutation, John Wiley & Sons, Inc., US, vol. 7, No. 3, pp. 244-255 (Jan. 1996).

Cruse et al., "Illustrated Dictionary of Immunology". Boca Raton: CRC Press, p. 512 (2003).

Dai-Wu Seol, et al., "Signaling Events Triggered by Tumor Necrosis Factor-related Apoptosis-inducing Ligand (TRAIL): Caspase-8 is Required for Trail-Induced Apoptosis". Cancer Research, vol. 61, pp. 1138-1143 (2001).

Dasgupta, et al., "Flow of multiple fluids in a small' dimension". Analytical Chemistry, vol. 74, No. 7, pp. 208-213 (2002).

De Farias, P., et al., Investigation of red blood cell antigens with highly fluorescent and stable semiconductor quantum dots, J. Bimedical Optics, 2005, pp. 1-4, vol. 10(4).

Decher, G., "Fuzzy Nanoassemblies: Toward Layered Polymeric Multicomposites". Science, vol. 277, pp. 1232-1237 (Aug. 29, 1997).

Denomme, G. A., et al., "High throughput multiplex single-nucloetide polymorphism analysis for red cell and platelet antigen genotypes". Transfusion, vol. 45, pp. 660-666 (May 2005).

Denkov et al. "Mechanism of Formation of Two-Dimensional Crystals from Latex Particles on Substrates," langmuir, 1992, pp. 3183-3190, vol. 8.

Ding et al., "Direct molecular haplotyping of long-range genomic DNA with M1-PCR", Jun. 2003, vol. 100, 13: 7449-7453.

Du et al., "Sensitivity and Specificity of Metal Surface-Immobilized," Molecular Beacon, Biosensors; JACS 2005, vol. 127, No. 21, pp. 7932-7940.

Duggan, David J., et al., "Expression profiling using cDNA microarrays". Nature Genetics Supplement, vol. 21, pp. 10-14 (Jan. 1999).

Dunbar SA et al. "Application of the luminex LabMAP in rapid screening for mutations in the cystic fibrosis transmembrane conductance regulator gene: A pilot study" Clin Chem Sep. 2000; 46(9): 1498-500. with Abstract data, pp. 1 and 2.

Duquesnoy HLA Matchmaker: A Molecularly Based Algorithm for Histocompatibility Determination. I. Description of the Algorithm. Human Immunology, vol. 63, pp. 339-352 (2002).

Dziennik, S. R., et al., "Nondiffusive mechanisms enhance protein uptake rates in ion exchange particles". PNAS, vol. 100, No. 2, pp. 420-425 (2003).

Easteal, S. "DNA Fingerprinting by PCR Amplification of HLA Genes". DNA and Criminal Justice. 1991; Human Genetics Group, John Curtin School of Medical Research, pp. 121-127.

Egner et al. "Tagging in combinatorial chemistry: the use of coloured and fluorescent beads". Chem. Commun, pp. 735-736 (1997).

Elaissari et al., "Hydrophilic and cationic latex particles for the specific extraction of nucleic acids". J. Biomater, Sci Polymer Edn, vol. 10, pp. 403-420 (1999).

Erdogan et al., "Detection of mitochondrial single nucleotide polymorphisms using a primer elongation reaction on oligonucleotide microarrays", Nucleic Acid Research, 29: 1-7 (2001).

Ericsson, O., et al., "A dual-tag microarray platform for high-performance nucleic acid and protein analyses". Nucleic Acids Research, vol. 36, No. 8 e45, pp. 1-9 (2008).

Erlich, et al., "HLA DNA Typing and Transplantation", Immunity, 14: 347-356 (2001).

Fan et al., "Parallel Genotyping of Human SNPs Using Generic High-density Oligonucleotide Tag Arrays", Genome research, vol. 10, pp. 853-860 (2000).

Fatin-Rouge, N., et al., "Diffusion and Partitioning of Solutes in Agarose Hydrogels: The Relative Influence of Electrostatic and Specific Interactions", J. Phys. Chem. B., vol. 107, pp. 12126-12137 (2003).

Ferguson et al., "High-Density Fiber-Optic DNA Random Microsphere Array". Anal. Chem, vol. 72, pp. 5618-5624 (2000).

Filipovich et al., "Impact of donor type on outcome of bone marrow transplantation for Wiskott-Aldrich syndrome: collaborative study of the International Bone Marrow Transplant Registry and the National Marrow Donor Program", Blood, vol. 97, No. 6, pp. 1598-1603 (2001).

Finkel, et al. "Barcoding the Microworld". Analytical Chemistry, pp. 353-359 (Oct. 1, 2004).

Fitch, J.P. et al., "Rapid Development of Nucleic Acid Diagnostics", Proceedings of the IEEE 90 (11): 1708-1720 (Nov. 2002).

Fodor, S., et al., "Light-Directed, Spatially Addressable Parallel Chemical Synthesis" Research Article (Authors are at the Affymax Research Institute, 3180 Porter Drive, Palo Alto, CA 94304), pp. 767-773 (Feb. 15, 1991).

Fowke, Keith R., et al. "Genetic analysis of human DNA recovered from minute amounts of serum or plasma". Journal of Immunological Methods, vol. 80, pp. 45-51 (1995).

Frengen, Jomar, et al., "Demonstration and Minimization of Serum Interference in Flow Cytometric Two-Site Immunoassays". Clinical Chemistry, vol. 40, No. 3, pp. 420-425 (1994).

Fuh et al. Single Fibre Optic Fluorescence pH Probe. Analyst, 112:1159-1163 (1987).

Fuh et al., "A Method for Determination of Particle Magnetic Susceptibility with Analytical Magnetapheresis". Anal. Chem, vol. 72, pp. 3590-3595 (2000).

Fulton et al. "Advanced multiplexed analysis with the FlowMetrix system". Clinical Chemistry, vol. 43:9, pp. 1749-1756 (1997).

Gahan, P. B., "Circulating Nucleic Acid in Plasma and Serum: Diagnosis and Prognosis in Cancer". Oncology, vol. 32, No. 6, pp. 20-22 (Oct. 2008); Weekly news updates on www.cli-online.com.

Gates, et al., "Photonic Crystals that can be Addressed with an External Magnetic Field". Adv Mater, vol. 13, No. 21, pp. 1605-1608 (2001).

Gelfi, C., et al., "Investigation of the Properties of Novel Acrylamido Monomers by Capilary Zone Electrophoresis", Journal of Chromatography, vol. 608, pp. 333-341 (1992).

Gerlach. Human Lymphocyte Antigen Molecular Typing. Archives of Pathology & Laboratory Medicine. vol. 126, pp. 281-284 (2002).

Ghazaly, et al,, "Synthesis and Characterization of a Macromonomer Crosslinker". Journal of Applied Polymer Science, vol. 77, pp. 1362-1368 (2000).

Ghosh et al. "Covalent attachement of oligonucleotides to solid supports". Nucleic Acids Research. vol. 16, No. 13; pp. 5363-5371 (1987).

Ghosh, P., et al., "A Simple Lithographic Approach for Preparing Patterned, Micron-Scale Corrals for Controlling Cell Growth". Angew. Chem. Int. Ed., vol. 38, No. 11, pp. 1592-1595 (1999).

Giorgi, R., et al., "Nanotechnologies for Conservation of Cultural Heritage: Paper and Canvas Deacidification". Langmuir, vol. 18, pp. 8198-8203 (2002).

Good, L., et al., "Bactericidal antisense effects of peptide-DNA conjugates". Nature Biotechnology, vol. 19, pp. 360-364 (2001).

Goodey et al., "Development of multianalyte sensor arrays composed of chemically derivatized polymeric microspheres localized in micromachined cavitites". Journal of American Chemical Society, vol. 123, pp. 2559-2570 (2001).

Graf et al., "A general method to coat colloidal particles with silica". Langmuir, vol. 19, pp. 6693-6700 (2003).

Grazia et al. In-vivo biomedical monitoring by fiber-optic system. Journal of Lightwave Technology. 13, 1396-1406 (1995).

Yellen, et al., "Statistical Analysis of Weakest Link in Chains of Magnetic Particle Carriers for Applications in Printing Biochemical Arrays". European Cells and Materials, vol. 3, pp. 88-91 (2002).

Grondahl, et al., "Encoding Combinatorial Libraries: A Novel Application of Fluorescent Silica Colloids". Langmuir, vol. 16, No. 25, pp. 9709-9715 (2000).

Gruttner, et al., "New types of silica-fortified magnetic nanoparticles as tools for molecular biology applications". Journal of Magnetism and Magnetic Materials, vol. 94, pp. 8-15 (1999).

Gubin et al., "Identification of the Dombrock blood group glycoprotein as a polymorphic member of the ADP-ribosyltransferase gene family", Blood, Oct. 1, 2000, vol. 96, No. 7, pp. 2621-2627.

Gullberg, M., et al., "Cytokine detection by antibody-based proximity ligation". PNAS, vol. 101, No. 22, pp. 8420-8424 (Jun. 2004).

Guo, Zhen et al. "Oligonucleotide arrays for high-throughput SNPs detection in the MHC class I genes: HLA-B as a model system". Genome Research; vol. 12, No. 3, pp. 447-457 (Mar. 2002).

Guo, Zhen, "Direct fluorescence analysis of genetic polymorphisms . . . oligonucleotide arrays on glass supports", Nucleic Acids Research, Jul. 1994, Oxford Univ Press, pp. 5456-5465.

Gupta et al. ("Hydrogels: from controlled release to pH-responsive drug delivery" Drug Discov Today, May 15, 2002;7(10):569-79.

Gustafsdottir, S. M., "In vitro analysis of DNA—protein interactions by proximity ligation". PNAS, vol. 104, No. 9, pp. 3067-3072 (Feb. 2007).

Haab et al. Single Molecule Fluorescence Burst Detection of DNA Fragments Separated by Capillary Electrophoresis. Analytical Chemistry, vol. 67 (No. 18): 3253-3256 (1995).

Hacis et al., "Resequencing and mutational analysis using oligonucleotide microarrays", Nature America; 21: 42-47 (1999).

Hakala, H., et al. "Simultaneous detection of several oligonucleotides by time-resolved fluorometry: the use of a mixture of categorized microparticles in a sandwich type mixed-phase hybridization assay". Nucleic Acids Research, vol. 26. pp. 5591-5585 (1998).

Hashimi et al., "A Flexible Array format for large-scale, rapid blood group DNA typing". Transfusion, Published Online Apr. 6, 2004, vol. 45, Issue 5, pp. 680-688 (May 2005).

Hashmi, G., et al, "Determination of 24 minor red blood cell antigens for more than 2000 blood donors by high-throughput DNA analysis". Transfusion, vol. 47, No. 4, pp. 736-747 (Apr. 2007).

Zaer, Farid, et al., "Antibody Screening by Enzyme-Linked Immunosorbent Assay Using Pooled Soluble HLA in Renal Transplant Candidates". Transplantation, vol. 63, No. 1, pp. 48-61 (Jan. 15, 1997).

Heinrich, et al., "Interleukin-6-type Cytokine Signaling through the gp 130/Jak/STAT pathway". Biochem J, vol. 334, pp. 297-314 (1998).

Helgesen, et al., "Aggregation of magnetic microspheres: experiements and simulations". Physical Review Letters, vol. 61, No. 15, pp. 1736-1739 (1998).

Helmuth, R., et al., "HLA-DQ Allele and Genotype Frequencies in Various Human Populations, Determined by Using Enzymatic Amplification and Oligonucleotide Probes". Am. J. Hum. Genet, vol. 47, pp. 616-523 (1990).

Yershov et al., "DNA analysis and diagnostics on oligonulceotide microchips". Proceedings of the National Academy of Sciences of the United States of America, vol. 93, No. 10, pp. 4913-4918 (May 14, 1996).

Hiller, J., et al., "Reversibly erasable nanoporous anti-reflection coatings from polyelectrolyte multilayers". Nature Materials, vol. 1, pp. 59-63 (Sep. 2002).

Hirata, H., et al., "Caspases Are Activated in a Branched Protease Cascade and Control Distinct Downstream Processes in Fas-induced Apoptosis". J. Exp. Med., vol. 187, No. 4, pp. 587-600 (1998).

Hizume, et al., "Tandem repeat DNA localizing on the proximal DAPI bands of chromosomes in Larix, pinaceae". Genome, vol. 45, pp. 777-783 (2002).

Holtz, J., et al., "Intelligent Polymerized Crystalline Colloidal Array. Novel Sensor Materials", Analytical Chemistry, vol. 70, No. 4, pp. 780-791 (1998).

Balass et al. "Recovery of high-affinity phage from a Nitrostretavidin matrix in phage-display technology". Analytical Biochemistry. vol. 243: 264-269 (1996).

Barany, Francis, "Genetic Disease Detection and DNA Amplification using Cloned Thermostable Ligase", Proceedings of the National Academy of Sciences of the United States of America, vol. 88, pp. 189-193 (Jan. 1991).

Fodor, S., et al., "Light-Directed, Spatially Addressable Parallel Chemical Synthesis". Research Article (Authors are at the Affymax Research Institute, 3180 Porter Drive, Palo Alto, CA 94304), pp. 767-773 (Feb. 15, 1991).

Ghazaly, et al., "Synthesis and Characterization of a Macromonomer Crosslinker". Journal of Applied Polymer Science, vol. 77, pp. 1362-1368 (2000).

Giorgi, R., et al., "Nanotechnologies for Conservation of Cultural Heritage: Paper and Canvas Deacidification". Langmuir, vol. 18, pp. 8198-8203 (2002).

Guo, Zhen, "Direct fluorescence analysis of genetic polymorphisms . . . oligonucleotide arrays on glass supports". Nucleic Acids Research, Jul. 1994, Oxford Univ Press, pp. 5456-5465.

Gupta et al. ("Hydrogels: from controlled release to pH-responsive drug delivery" Drug Discov Today. May 15, 2002;7(10):569-79.

Hakala, H., et al. "Simultaneous detection of several oligonucleotides by time-resolved fluorometry: the use of a mixture of categorized microparticles in a sandwich type mixed-phase hybridization assay". Nucleic Acids Research, Vol. 26. pp. 5581-5585 (1998).

Zaer, Farid, et al., "Antibody Screening by Enzyme-Linked Immunosorbent Assay Using Pooled Soluble HLA in Renal Transplant Candidates". Transplantation, vol. 63, No. 1, pp. 48-51 (Jan. 15, 1997).

Helmuth, R., et al., "HLA-DQ Allele and Genotype Frequencies in Various Human Populations, Determined by Using Enzymatic Amplification and Oligonucleotide Probes". Am. J. Hum. Genet, vol. 47, pp. 515-523 (1990).

Holtz, J., et al., "Intelligent Polymerized Crystalline Colloidal Array: Novel Sensor Materials", Analytical Chemistry, vol. 70, No. 4, pp. 780-791 (1998).

* cited by examiner

SEQUENCE LISTING

<160> NUMBER OF SEQ ID NOS: 137

<210> SEQ ID NO 1
<211> LENGTH: 19
<212> TYPE: DNA
<213> ORGANISM: Artificial Sequence
<220> FEATURE:
<223> OTHER INFORMATION: Artificial Probe

<400> SEQUENCE: 1
cagaaggaca tcctggaag                                                   19

<210> SEQ ID NO 2
<211> LENGTH: 15
<212> TYPE: DNA
<213> ORGANISM: Artificial Sequence
<220> FEATURE:
<223> OTHER INFORMATION: Artificial Probe

<400> SEQUENCE: 2
tcggtcttcc aggat                                                       15

<210> SEQ ID NO 3
<211> LENGTH: 19
<212> TYPE: DNA
<213> ORGANISM: Artificial Sequence
<220> FEATURE:
<223> OTHER INFORMATION: Artificial Probe

<400> SEQUENCE: 3
accgagagag cctgcggat                                                   19

<210> SEQ ID NO 4
<211> LENGTH: 19
<212> TYPE: DNA
<213> ORGANISM: Artificial Sequence
<220> FEATURE:
<223> OTHER INFORMATION: Artificial Probe

<400> SEQUENCE: 4
atccgcaggc tctctcggt                                                   19

<210> SEQ ID NO 5
<211> LENGTH: 15
<212> TYPE: DNA
<213> ORGANISM: Artificial Sequence

```
<220> FEATURE:
<223> OTHER INFORMATION: Artificial Probe

<400> SEQUENCE: 5
tcctgcttcc aggat                                                      15

<210> SEQ ID NO 6
<211> LENGTH: 19
<212> TYPE: DNA
<213> ORGANISM: Artificial Sequence
<220> FEATURE:
<223> OTHER INFORMATION: Artificial Probe

<400> SEQUENCE: 6
caggagaggc ctgagtatt                                                  19

<210> SEQ ID NO 7
<211> LENGTH: 19
<212> TYPE: DNA
<213> ORGANISM: Artificial Sequence
<220> FEATURE:
<223> OTHER INFORMATION: Artificial Probe

<400> SEQUENCE: 7
aatactcagg cctctcctg                                                  19

<210> SEQ ID NO 8
<211> LENGTH: 15
<212> TYPE: DNA
<213> ORGANISM: Artificial Sequence
<220> FEATURE:
<223> OTHER INFORMATION: Artificial Probe

<400> SEQUENCE: 8
cgcctcttcc aggat                                                      15

<210> SEQ ID NO 9
<211> LENGTH: 16
<212> TYPE: DNA
<213> ORGANISM: Artificial Sequence
<220> FEATURE:
<223> OTHER INFORMATION: Artificial Probe

<400> SEQUENCE: 9
aggcggtcca tgcggc                                                     16

<210> SEQ ID NO 10
<211> LENGTH: 16
<212> TYPE: DNA
<213> ORGANISM: Artificial Sequence
<220> FEATURE:
<223> OTHER INFORMATION: Artificial Probe

<400> SEQUENCE: 10
gccgcatgga ccgcct                                                     16

<210> SEQ ID NO 11
<211> LENGTH: 19
<212> TYPE: DNA
<213> ORGANISM: Artificial Sequence
<220> FEATURE:
<223> OTHER INFORMATION: Artificial Probe

<400> SEQUENCE: 11
cagaaggaca tcctggaag                                                  19
```

```
<210> SEQ ID NO 12
<211> LENGTH: 19
<212> TYPE: DNA
<213> ORGANISM: Artificial Sequence
<220> FEATURE:
<223> OTHER INFORMATION: Artificial Probe

<400> SEQUENCE: 12
accgagagag cctgcggat                                                19

<210> SEQ ID NO 13
<211> LENGTH: 26
<212> TYPE: DNA
<213> ORGANISM: Artificial Sequence
<220> FEATURE:
<223> OTHER INFORMATION: Artificial Probe

<400> SEQUENCE: 13
cgcaggtatc gtattaattg atctgc                                        26

<210> SEQ ID NO 14
<211> LENGTH: 25
<212> TYPE: DNA
<213> ORGANISM: Artificial Sequence
<220> FEATURE:
<223> OTHER INFORMATION: Artificial Probe

<400> SEQUENCE: 14
cctcatgtca acgaagaaca gaacc                                         25

<210> SEQ ID NO 15
<211> LENGTH: 25
<212> TYPE: DNA
<213> ORGANISM: Artificial Sequence
<220> FEATURE:
<223> OTHER INFORMATION: Artificial Probe

<400> SEQUENCE: 15
attgaagcct gccgtcggag actaa                                         25

<210> SEQ ID NO 16
<211> LENGTH: 25
<212> TYPE: DNA
<213> ORGANISM: Artificial Sequence
<220> FEATURE:
<223> OTHER INFORMATION: Artificial Probe

<400> SEQUENCE: 16
agactgcgtg ttggctctgt cacag                                         25

<210> SEQ ID NO 17
<211> LENGTH: 25
<212> TYPE: DNA
<213> ORGANISM: Artificial Sequence
<220> FEATURE:
<223> OTHER INFORMATION: Artificial Probe

<400> SEQUENCE: 17
ttatggtgat cagtcaacca ccagg                                         25

<210> SEQ ID NO 18
<211> LENGTH: 25
<212> TYPE: DNA
<213> ORGANISM: Artificial Sequence
<220> FEATURE:
<223> OTHER INFORMATION: Artificial Probe

<400> SEQUENCE: 18
```
gagacacctt atgttctata catgc                                    25

<210> SEQ ID NO 19
<211> LENGTH: 25
<212> TYPE: DNA
<213> ORGANISM: Artificial Sequence
<220> FEATURE:
<223> OTHER INFORMATION: Artificial Probe

<400> SEQUENCE: 19
tccatgcgct tgctcttcat ctagc                                    25

<210> SEQ ID NO 20
<211> LENGTH: 25
<212> TYPE: DNA
<213> ORGANISM: Artificial Sequence
<220> FEATURE:
<223> OTHER INFORMATION: Artificial Probe

<400> SEQUENCE: 20
gccttacata catctgtcgg ttgta                                    25

<210> SEQ ID NO 21
<211> LENGTH: 25
<212> TYPE: DNA
<213> ORGANISM: Artificial Sequence
<220> FEATURE:
<223> OTHER INFORMATION: Artificial Probe

<400> SEQUENCE: 21
cacaaggagg tcagaccaga ttgaa                                    25

<210> SEQ ID NO 22
<211> LENGTH: 25
<212> TYPE: DNA
<213> ORGANISM: Artificial Sequence
<220> FEATURE:
<223> OTHER INFORMATION: Artificial Probe

<400> SEQUENCE: 22
gccacagata atattcacat cgtgt                                    25

<210> SEQ ID NO 23
<211> LENGTH: 25
<212> TYPE: DNA
<213> ORGANISM: Artificial Sequence
<220> FEATURE:
<223> OTHER INFORMATION: Artificial Probe

<400> SEQUENCE: 23
acacatacga ttctgcgaac ttcaa                                    25

<210> SEQ ID NO 24
<211> LENGTH: 25
<212> TYPE: DNA
<213> ORGANISM: Artificial Sequence
<220> FEATURE:
<223> OTHER INFORMATION: Artificial Probe

<400> SEQUENCE: 24
ttacaggatg tgctcaacag acgtt                                    25

<210> SEQ ID NO 25
<211> LENGTH: 25
<212> TYPE: DNA
<213> ORGANISM: Artificial Sequence

```
<220> FEATURE:
<223> OTHER INFORMATION: Artificial Probe

<400> SEQUENCE: 25
gctcacaata attgcatgag ttgcc                                       25

<210> SEQ ID NO 26
<211> LENGTH: 27
<212> TYPE: DNA
<213> ORGANISM: Artificial Sequence
<220> FEATURE:
<223> OTHER INFORMATION: Artificial Probe

<400> SEQUENCE: 26
ctgcactgct cattaatata cttctgg                                     27

<210> SEQ ID NO 27
<211> LENGTH: 26
<212> TYPE: DNA
<213> ORGANISM: Artificial Sequence
<220> FEATURE:
<223> OTHER INFORMATION: Artificial Probe

<400> SEQUENCE: 27
ttcacgcact gactgacaga ctgctt                                      26

<210> SEQ ID NO 28
<211> LENGTH: 25
<212> TYPE: DNA
<213> ORGANISM: Artificial Sequence
<220> FEATURE:
<223> OTHER INFORMATION: Artificial Probe

<400> SEQUENCE: 28
caacatcatc acgcagagca tcatt                                       25

<210> SEQ ID NO 29
<211> LENGTH: 25
<212> TYPE: DNA
<213> ORGANISM: Artificial Sequence
<220> FEATURE:
<223> OTHER INFORMATION: Artificial Probe

<400> SEQUENCE: 29
gcatcagcta actccttcgt gtatt                                       25

<210> SEQ ID NO 30
<211> LENGTH: 27
<212> TYPE: DNA
<213> ORGANISM: Artificial Sequence
<220> FEATURE:
<223> OTHER INFORMATION: Artificial Probe

<400> SEQUENCE: 30
ggcgttatca cggtaatgat taacagc                                     27

<210> SEQ ID NO 31
<211> LENGTH: 25
<212> TYPE: DNA
<213> ORGANISM: Artificial Sequence
<220> FEATURE:
<223> OTHER INFORMATION: Artificial Probe

<400> SEQUENCE: 31
acatcaatct ctctgaccgt tccgc                                       25
```

<210> SEQ ID NO 32
<211> LENGTH: 25
<212> TYPE: DNA
<213> ORGANISM: Artificial Sequence
<220> FEATURE:
<223> OTHER INFORMATION: Artificial Probe

<400> SEQUENCE: 32
gccttatgct cgaactgacc ataac                              25

<210> SEQ ID NO 33
<211> LENGTH: 29
<212> TYPE: DNA
<213> ORGANISM: Artificial Sequence
<220> FEATURE:
<223> OTHER INFORMATION: Artificial Probe

<400> SEQUENCE: 33
cggatatcac cacgatcaat cataggtaa                          29

<210> SEQ ID NO 34
<211> LENGTH: 25
<212> TYPE: DNA
<213> ORGANISM: Artificial Sequence
<220> FEATURE:
<223> OTHER INFORMATION: Artificial Probe

<400> SEQUENCE: 34
ccttaatctg ctgcaatgcc acagc                              25

<210> SEQ ID NO 35
<211> LENGTH: 25
<212> TYPE: DNA
<213> ORGANISM: Artificial Sequence
<220> FEATURE:
<223> OTHER INFORMATION: Artificial Probe

<400> SEQUENCE: 35
tagctctccg cctacaatga cgtca                              25

<210> SEQ ID NO 36
<211> LENGTH: 25
<212> TYPE: DNA
<213> ORGANISM: Artificial Sequence
<220> FEATURE:
<223> OTHER INFORMATION: Artificial Probe

<400> SEQUENCE: 36
aggaacgcct tacgttgatt attga                              25

<210> SEQ ID NO 37
<211> LENGTH: 25
<212> TYPE: DNA
<213> ORGANISM: Artificial Sequence
<220> FEATURE:
<223> OTHER INFORMATION: Artificial Probe

<400> SEQUENCE: 37
gagtcagtac cgatgtagcc gataa                              25

<210> SEQ ID NO 38
<211> LENGTH: 25
<212> TYPE: DNA
<213> ORGANISM: Artificial Sequence
<220> FEATURE:
<223> OTHER INFORMATION: Artificial Probe

<400> SEQUENCE: 38
actcgaatga accaggcgat aatgg        25

<210> SEQ ID NO 39
<211> LENGTH: 25
<212> TYPE: DNA
<213> ORGANISM: Artificial Sequence
<220> FEATURE:
<223> OTHER INFORMATION: Artificial Probe

<400> SEQUENCE: 39
attatatctg ccgcgaaggt acgcc        25

<210> SEQ ID NO 40
<211> LENGTH: 26
<212> TYPE: DNA
<213> ORGANISM: Artificial Sequence
<220> FEATURE:
<223> OTHER INFORMATION: Artificial Probe

<400> SEQUENCE: 40
ggacagacag tggctacggc tcagtt       26

<210> SEQ ID NO 41
<211> LENGTH: 25
<212> TYPE: DNA
<213> ORGANISM: Artificial Sequence
<220> FEATURE:
<223> OTHER INFORMATION: Artificial Probe

<400> SEQUENCE: 41
cggtattcgc ttaattcagc acaac        25

<210> SEQ ID NO 42
<211> LENGTH: 25
<212> TYPE: DNA
<213> ORGANISM: Artificial Sequence
<220> FEATURE:
<223> OTHER INFORMATION: Artificial Probe

<400> SEQUENCE: 42
gctcttacct gttgtgcaga tataa        25

<210> SEQ ID NO 43
<211> LENGTH: 20
<212> TYPE: DNA
<213> ORGANISM: Artificial Sequence
<220> FEATURE:
<223> OTHER INFORMATION: Artificial Probe

<400> SEQUENCE: 43
gttgatgtca tgtgtcgcac             20

<210> SEQ ID NO 44
<211> LENGTH: 20
<212> TYPE: DNA
<213> ORGANISM: Artificial Sequence
<220> FEATURE:
<223> OTHER INFORMATION: Artificial Probe

<400> SEQUENCE: 44
tcgtgccttg tcattcggga             20

<210> SEQ ID NO 45
<211> LENGTH: 20
<212> TYPE: DNA
<213> ORGANISM: Artificial Sequence

```
<220> FEATURE:
<223> OTHER INFORMATION: Artificial Probe

<400> SEQUENCE: 45
cgtgcaagtt accgagctga                                            20

<210> SEQ ID NO 46
<211> LENGTH: 20
<212> TYPE: DNA
<213> ORGANISM: Artificial Sequence
<220> FEATURE:
<223> OTHER INFORMATION: Artificial Probe

<400> SEQUENCE: 46
tagatcagtt ggactcgatg                                            20

<210> SEQ ID NO 47
<211> LENGTH: 20
<212> TYPE: DNA
<213> ORGANISM: Artificial Sequence
<220> FEATURE:
<223> OTHER INFORMATION: Artificial Probe

<400> SEQUENCE: 47
gcagggaatt gccgaccata                                            20

<210> SEQ ID NO 48
<211> LENGTH: 20
<212> TYPE: DNA
<213> ORGANISM: Artificial Sequence
<220> FEATURE:
<223> OTHER INFORMATION: Artificial Probe

<400> SEQUENCE: 48
acgttcgtca agagtcgcat                                            20

<210> SEQ ID NO 49
<211> LENGTH: 20
<212> TYPE: DNA
<213> ORGANISM: Artificial Sequence
<220> FEATURE:
<223> OTHER INFORMATION: Artificial Probe

<400> SEQUENCE: 49
cgttcctaaa gctgagtctg                                            20

<210> SEQ ID NO 50
<211> LENGTH: 20
<212> TYPE: DNA
<213> ORGANISM: Artificial Sequence
<220> FEATURE:
<223> OTHER INFORMATION: Artificial Probe

<400> SEQUENCE: 50
gagaggccgt cgctatacat                                            20

<210> SEQ ID NO 51
<211> LENGTH: 20
<212> TYPE: DNA
<213> ORGANISM: Artificial Sequence
<220> FEATURE:
<223> OTHER INFORMATION: Artificial Probe

<400> SEQUENCE: 51
aagccagatc gaccatcgta                                            20
```

```
<210> SEQ ID NO 52
<211> LENGTH: 20
<212> TYPE: DNA
<213> ORGANISM: Artificial Sequence
<220> FEATURE:
<223> OTHER INFORMATION: Artificial Probe

<400> SEQUENCE: 52
gacgccgtta tgagagtcca                                              20

<210> SEQ ID NO 53
<211> LENGTH: 20
<212> TYPE: DNA
<213> ORGANISM: Artificial Sequence
<220> FEATURE:
<223> OTHER INFORMATION: Artificial Probe

<400> SEQUENCE: 53
atatcgtgtc acaggtcgtt                                              20

<210> SEQ ID NO 54
<211> LENGTH: 20
<212> TYPE: DNA
<213> ORGANISM: Artificial Sequence
<220> FEATURE:
<223> OTHER INFORMATION: Artificial Probe

<400> SEQUENCE: 54
atgatgtgca aagtgccgtc                                              20

<210> SEQ ID NO 55
<211> LENGTH: 20
<212> TYPE: DNA
<213> ORGANISM: Artificial Sequence
<220> FEATURE:
<223> OTHER INFORMATION: Artificial Probe

<400> SEQUENCE: 55
tccgtctgtt gagttaggcc                                              20

<210> SEQ ID NO 56
<211> LENGTH: 20
<212> TYPE: DNA
<213> ORGANISM: Artificial Sequence
<220> FEATURE:
<223> OTHER INFORMATION: Artificial Probe

<400> SEQUENCE: 56
ctcgaccgtt agcagcatga                                              20

<210> SEQ ID NO 57
<211> LENGTH: 20
<212> TYPE: DNA
<213> ORGANISM: Artificial Sequence
<220> FEATURE:
<223> OTHER INFORMATION: Artificial Probe

<400> SEQUENCE: 57
ccgagatgta ccgctatcgt                                              20

<210> SEQ ID NO 58
<211> LENGTH: 20
<212> TYPE: DNA
<213> ORGANISM: Artificial Sequence
<220> FEATURE:
<223> OTHER INFORMATION: Artificial Probe

<400> SEQUENCE: 58
```

-continued

```
agagcgcatg aatccgtagt                                              20

<210> SEQ ID NO 59
<211> LENGTH: 19
<212> TYPE: DNA
<213> ORGANISM: Artificial Sequence
<220> FEATURE:
<223> OTHER INFORMATION: Artificial Probe

<400> SEQUENCE: 59
cggggtgtga ccagacaca                                               19

<210> SEQ ID NO 60
<211> LENGTH: 19
<212> TYPE: DNA
<213> ORGANISM: Artificial Sequence
<220> FEATURE:
<223> OTHER INFORMATION: Artificial Probe

<400> SEQUENCE: 60
gggtgtaccg ggcagtgac                                               19

<210> SEQ ID NO 61
<211> LENGTH: 19
<212> TYPE: DNA
<213> ORGANISM: Artificial Sequence
<220> FEATURE:
<223> OTHER INFORMATION: Artificial Probe

<400> SEQUENCE: 61
gcggcctagc gccgagtac                                               19

<210> SEQ ID NO 62
<211> LENGTH: 17
<212> TYPE: DNA
<213> ORGANISM: Artificial Sequence
<220> FEATURE:
<223> OTHER INFORMATION: Artificial Probe

<400> SEQUENCE: 62
gcggcctgtt gccgagt                                                 17

<210> SEQ ID NO 63
<211> LENGTH: 19
<212> TYPE: DNA
<213> ORGANISM: Artificial Sequence
<220> FEATURE:
<223> OTHER INFORMATION: Artificial Probe

<400> SEQUENCE: 63
cgttatgtga ccagataca                                               19

<210> SEQ ID NO 64
<211> LENGTH: 19
<212> TYPE: DNA
<213> ORGANISM: Artificial Sequence
<220> FEATURE:
<223> OTHER INFORMATION: Artificial Probe

<400> SEQUENCE: 64
cgtcttgtaa ccagacaca                                               19

<210> SEQ ID NO 65
<211> LENGTH: 19
<212> TYPE: DNA
<213> ORGANISM: Artificial Sequence
```

-continued

```
<220> FEATURE:
<223> OTHER INFORMATION: Artificial Probe

<400> SEQUENCE: 65
cgtcttgtga ccagataca                                                19

<210> SEQ ID NO 66
<211> LENGTH: 19
<212> TYPE: DNA
<213> ORGANISM: Artificial Sequence
<220> FEATURE:
<223> OTHER INFORMATION: Artificial Probe

<400> SEQUENCE: 66
gcggcctgat gccgagtac                                                19

<210> SEQ ID NO 67
<211> LENGTH: 19
<212> TYPE: DNA
<213> ORGANISM: Artificial Sequence
<220> FEATURE:
<223> OTHER INFORMATION: Artificial Probe

<400> SEQUENCE: 67
gacccgagcg gagttggac                                                19

<210> SEQ ID NO 68
<211> LENGTH: 19
<212> TYPE: DNA
<213> ORGANISM: Artificial Sequence
<220> FEATURE:
<223> OTHER INFORMATION: Artificial Probe

<400> SEQUENCE: 68
gaggggaccc gggcggagt                                                19

<210> SEQ ID NO 69
<211> LENGTH: 19
<212> TYPE: DNA
<213> ORGANISM: Artificial Sequence
<220> FEATURE:
<223> OTHER INFORMATION: Artificial Probe

<400> SEQUENCE: 69
cgtcttgtaa ccagataca                                                19

<210> SEQ ID NO 70
<211> LENGTH: 19
<212> TYPE: DNA
<213> ORGANISM: Artificial Sequence
<220> FEATURE:
<223> OTHER INFORMATION: Artificial Probe

<400> SEQUENCE: 70
cgtcttgtga gcagaagca                                                19

<210> SEQ ID NO 71
<211> LENGTH: 19
<212> TYPE: DNA
<213> ORGANISM: Artificial Sequence
<220> FEATURE:
<223> OTHER INFORMATION: Artificial Probe

<400> SEQUENCE: 71
cgacgtggag gtgtaccgg                                                19
```

```
<210> SEQ ID NO 72
<211> LENGTH: 17
<212> TYPE: DNA
<213> ORGANISM: Artificial Sequence
<220> FEATURE:
<223> OTHER INFORMATION: Artificial Probe

<400> SEQUENCE: 72
gccgcctgac gccgagt                                                   17

<210> SEQ ID NO 73
<211> LENGTH: 18
<212> TYPE: DNA
<213> ORGANISM: Artificial Sequence
<220> FEATURE:
<223> OTHER INFORMATION: Artificial Probe

<400> SEQUENCE: 73
ggccgcctgc cgccgagt                                                  18

<210> SEQ ID NO 74
<211> LENGTH: 19
<212> TYPE: DNA
<213> ORGANISM: Artificial Sequence
<220> FEATURE:
<223> OTHER INFORMATION: Artificial Probe

<400> SEQUENCE: 74
gaccgagcgc gtgcggggt                                                 19

<210> SEQ ID NO 75
<211> LENGTH: 19
<212> TYPE: DNA
<213> ORGANISM: Artificial Sequence
<220> FEATURE:
<223> OTHER INFORMATION: Artificial Probe

<400> SEQUENCE: 75
gctggggcgg cttgacgcc                                                 19

<210> SEQ ID NO 76
<211> LENGTH: 19
<212> TYPE: DNA
<213> ORGANISM: Artificial Sequence
<220> FEATURE:
<223> OTHER INFORMATION: Artificial Probe

<400> SEQUENCE: 76
gggtgtatcg ggcggtgac                                                 19

<210> SEQ ID NO 77
<211> LENGTH: 18
<212> TYPE: DNA
<213> ORGANISM: Artificial Sequence
<220> FEATURE:
<223> OTHER INFORMATION: Artificial Probe

<400> SEQUENCE: 77
ggcggcctga cgccgagt                                                  18

<210> SEQ ID NO 78
<211> LENGTH: 19
<212> TYPE: DNA
<213> ORGANISM: Artificial Sequence
<220> FEATURE:
<223> OTHER INFORMATION: Artificial Probe

<400> SEQUENCE: 78
```

```
cgcttcgaca gcgacgtgg                                                    19

<210> SEQ ID NO 79
<211> LENGTH: 19
<212> TYPE: DNA
<213> ORGANISM: Artificial Sequence
<220> FEATURE:
<223> OTHER INFORMATION: Artificial Probe

<400> SEQUENCE: 79
aaccgagaag agtacgtgc                                                    19

<210> SEQ ID NO 80
<211> LENGTH: 20
<212> TYPE: DNA
<213> ORGANISM: Artificial Sequence
<220> FEATURE:
<223> OTHER INFORMATION: Artificial Probe

<400> SEQUENCE: 80
gttgatgtca tgtgtcgcac                                                   20

<210> SEQ ID NO 81
<211> LENGTH: 20
<212> TYPE: DNA
<213> ORGANISM: Artificial Sequence
<220> FEATURE:
<223> OTHER INFORMATION: Artificial Probe

<400> SEQUENCE: 81
acgttcgtca agagtcgcat                                                   20

<210> SEQ ID NO 82
<211> LENGTH: 25
<212> TYPE: DNA
<213> ORGANISM: Artificial Sequence
<220> FEATURE:
<223> OTHER INFORMATION: Artificial Probe

<400> SEQUENCE: 82
gagtcagtac cgatgtagcc gataa                                             25

<210> SEQ ID NO 83
<211> LENGTH: 25
<212> TYPE: DNA
<213> ORGANISM: Artificial Sequence
<220> FEATURE:
<223> OTHER INFORMATION: Artificial Probe

<400> SEQUENCE: 83
gctcttacct gttgtgcaga tataa                                             25

<210> SEQ ID NO 84
<211> LENGTH: 27
<212> TYPE: DNA
<213> ORGANISM: Artificial Sequence
<220> FEATURE:
<223> OTHER INFORMATION: Artificial Probe

<400> SEQUENCE: 84
ggcgttatca cggtaatgat taacagc                                           27

<210> SEQ ID NO 85
<211> LENGTH: 25
<212> TYPE: DNA
<213> ORGANISM: Artificial Sequence
```

```
<220> FEATURE:
<223> OTHER INFORMATION: Artificial Probe

<400> SEQUENCE: 85
ccttaatctg ctgcaatgcc acagc                                            25

<210> SEQ ID NO 86
<211> LENGTH: 20
<212> TYPE: DNA
<213> ORGANISM: Artificial Sequence
<220> FEATURE:
<223> OTHER INFORMATION: Artificial Probe

<400> SEQUENCE: 86
ctcgaccgtt agcagcatga                                                  20

<210> SEQ ID NO 87
<211> LENGTH: 25
<212> TYPE: DNA
<213> ORGANISM: Artificial Sequence
<220> FEATURE:
<223> OTHER INFORMATION: Artificial Probe

<400> SEQUENCE: 87
gagacacctt atgttctata catgc                                            25

<210> SEQ ID NO 88
<211> LENGTH: 26
<212> TYPE: DNA
<213> ORGANISM: Artificial Sequence
<220> FEATURE:
<223> OTHER INFORMATION: Artificial Probe

<400> SEQUENCE: 88
cgcaggtatc gtattaattg atctgc                                           26

<210> SEQ ID NO 89
<211> LENGTH: 27
<212> TYPE: DNA
<213> ORGANISM: Artificial Sequence
<220> FEATURE:
<223> OTHER INFORMATION: Artificial Probe

<400> SEQUENCE: 89
ctgcactgct cattaatata cttctgg                                          27

<210> SEQ ID NO 90
<211> LENGTH: 20
<212> TYPE: DNA
<213> ORGANISM: Artificial Sequence
<220> FEATURE:
<223> OTHER INFORMATION: Artificial Probe

<400> SEQUENCE: 90
atatcgtgtc acaggtcgtt                                                  20

<210> SEQ ID NO 91
<211> LENGTH: 25
<212> TYPE: DNA
<213> ORGANISM: Artificial Sequence
<220> FEATURE:
<223> OTHER INFORMATION: Artificial Probe

<400> SEQUENCE: 91
ttacaggatg tgctcaacag acgtt                                            25
```

```
<210> SEQ ID NO 92
<211> LENGTH: 19
<212> TYPE: DNA
<213> ORGANISM: Artificial Sequence
<220> FEATURE:
<223> OTHER INFORMATION: Artificial Probe

<400> SEQUENCE: 92
cggggtgtga ccagacaca                                               19

<210> SEQ ID NO 93
<211> LENGTH: 21
<212> TYPE: DNA
<213> ORGANISM: Artificial Sequence
<220> FEATURE:
<223> OTHER INFORMATION: Artificial Probe

<400> SEQUENCE: 93
ttgggtgtac cgggcagtga c                                            21

<210> SEQ ID NO 94
<211> LENGTH: 21
<212> TYPE: DNA
<213> ORGANISM: Artificial Sequence
<220> FEATURE:
<223> OTHER INFORMATION: Artificial Probe

<400> SEQUENCE: 94
tagcggccta gcgccgagta c                                            21

<210> SEQ ID NO 95
<211> LENGTH: 19
<212> TYPE: DNA
<213> ORGANISM: Artificial Sequence
<220> FEATURE:
<223> OTHER INFORMATION: Artificial Probe

<400> SEQUENCE: 95
ttgcggcctg ttgccgagt                                               19

<210> SEQ ID NO 96
<211> LENGTH: 19
<212> TYPE: DNA
<213> ORGANISM: Artificial Sequence
<220> FEATURE:
<223> OTHER INFORMATION: Artificial Probe

<400> SEQUENCE: 96
cgttatgtga ccagataca                                               19

<210> SEQ ID NO 97
<211> LENGTH: 21
<212> TYPE: DNA
<213> ORGANISM: Artificial Sequence
<220> FEATURE:
<223> OTHER INFORMATION: Artificial Probe

<400> SEQUENCE: 97
tacgtcttgt aaccagacac a                                            21

<210> SEQ ID NO 98
<211> LENGTH: 21
<212> TYPE: DNA
<213> ORGANISM: Artificial Sequence
<220> FEATURE:
<223> OTHER INFORMATION: Artificial Probe

<400> SEQUENCE: 98
```

-continued ttcgtcttgt gaccagatac a    21

<210> SEQ ID NO 99
<211> LENGTH: 21
<212> TYPE: DNA
<213> ORGANISM: Artificial Sequence
<220> FEATURE:
<223> OTHER INFORMATION: Artificial Probe

<400> SEQUENCE: 99
tcgcggcctg atgccgagta c    21

<210> SEQ ID NO 100
<211> LENGTH: 19
<212> TYPE: DNA
<213> ORGANISM: Artificial Sequence
<220> FEATURE:
<223> OTHER INFORMATION: Artificial Probe

<400> SEQUENCE: 100
gacccgagcg gagttggac    19

<210> SEQ ID NO 101
<211> LENGTH: 20
<212> TYPE: DNA
<213> ORGANISM: Artificial Sequence
<220> FEATURE:
<223> OTHER INFORMATION: Artificial Probe

<400> SEQUENCE: 101
agaggggacc cgggcggagt    20

<210> SEQ ID NO 102
<211> LENGTH: 21
<212> TYPE: DNA
<213> ORGANISM: Artificial Sequence
<220> FEATURE:
<223> OTHER INFORMATION: Artificial Probe

<400> SEQUENCE: 102
tccgtcttgt aaccagatac a    21

<210> SEQ ID NO 103
<211> LENGTH: 21
<212> TYPE: DNA
<213> ORGANISM: Artificial Sequence
<220> FEATURE:
<223> OTHER INFORMATION: Artificial Probe

<400> SEQUENCE: 103
ggcgtcttgt gagcagaagc a    21

<210> SEQ ID NO 104
<211> LENGTH: 19
<212> TYPE: DNA
<213> ORGANISM: Artificial Sequence
<220> FEATURE:
<223> OTHER INFORMATION: Artificial Probe

<400> SEQUENCE: 104
cgacgtggag gtgtaccgg    19

<210> SEQ ID NO 105
<211> LENGTH: 19
<212> TYPE: DNA
<213> ORGANISM: Artificial Sequence

```
<220> FEATURE:
<223> OTHER INFORMATION: Artificial Probe

<400> SEQUENCE: 105
cagccgcctg acgccgagt                                                    19

<210> SEQ ID NO 106
<211> LENGTH: 18
<212> TYPE: DNA
<213> ORGANISM: Artificial Sequence
<220> FEATURE:
<223> OTHER INFORMATION: Artificial Probe

<400> SEQUENCE: 106
ggccgcctgc cgccgagt                                                     18

<210> SEQ ID NO 107
<211> LENGTH: 21
<212> TYPE: DNA
<213> ORGANISM: Artificial Sequence
<220> FEATURE:
<223> OTHER INFORMATION: Artificial Probe

<400> SEQUENCE: 107
tagaccgagc gcgtgcgggg t                                                 21

<210> SEQ ID NO 108
<211> LENGTH: 19
<212> TYPE: DNA
<213> ORGANISM: Artificial Sequence
<220> FEATURE:
<223> OTHER INFORMATION: Artificial Probe

<400> SEQUENCE: 108
gctggggcgg cttgacgcc                                                    19

<210> SEQ ID NO 109
<211> LENGTH: 21
<212> TYPE: DNA
<213> ORGANISM: Artificial Sequence
<220> FEATURE:
<223> OTHER INFORMATION: Artificial Probe

<400> SEQUENCE: 109
tagggtgtat cgggcggtga c                                                 21

<210> SEQ ID NO 110
<211> LENGTH: 20
<212> TYPE: DNA
<213> ORGANISM: Artificial Sequence
<220> FEATURE:
<223> OTHER INFORMATION: Artificial Probe

<400> SEQUENCE: 110
atggcggcct gacgccgagt                                                   20

<210> SEQ ID NO 111
<211> LENGTH: 19
<212> TYPE: DNA
<213> ORGANISM: Artificial Sequence
<220> FEATURE:
<223> OTHER INFORMATION: Artificial Probe

<400> SEQUENCE: 111
cgcttcgaca gcgacgtgg                                                    19
```

```
<210> SEQ ID NO 112
<211> LENGTH: 19
<212> TYPE: DNA
<213> ORGANISM: Artificial Sequence
<220> FEATURE:
<223> OTHER INFORMATION: Artificial Probe

<400> SEQUENCE: 112
aaccgagaag agtacgtgc                                              19

<210> SEQ ID NO 113
<211> LENGTH: 21
<212> TYPE: DNA
<213> ORGANISM: Artificial Sequence
<220> FEATURE:
<223> OTHER INFORMATION: Artificial Probe

<400> SEQUENCE: 113
ttcgtcttgt gaccagatac a                                           21

<210> SEQ ID NO 114
<211> LENGTH: 20
<212> TYPE: DNA
<213> ORGANISM: Artificial Sequence
<220> FEATURE:
<223> OTHER INFORMATION: Artificial Probe

<400> SEQUENCE: 114
gttgatgtca tgtgtcgcac                                             20

<210> SEQ ID NO 115
<211> LENGTH: 15
<212> TYPE: DNA
<213> ORGANISM: Artificial Sequence
<220> FEATURE:
<223> OTHER INFORMATION: Artificial Probe

<400> SEQUENCE: 115
acgaagtgcg acaca                                                  15

<210> SEQ ID NO 116
<211> LENGTH: 41
<212> TYPE: DNA
<213> ORGANISM: Artificial Sequence
<220> FEATURE:
<223> OTHER INFORMATION: Artificial Probe

<400> SEQUENCE: 116
gttgatgtca tgtgtcgcac ttcgtcttgt gaccagatac a                     41

<210> SEQ ID NO 117
<211> LENGTH: 15
<212> TYPE: DNA
<213> ORGANISM: Artificial Sequence
<220> FEATURE:
<223> OTHER INFORMATION: Artificial Probe

<400> SEQUENCE: 117
acacagcgtg aagca                                                  15

<210> SEQ ID NO 118
<211> LENGTH: 21
<212> TYPE: DNA
<213> ORGANISM: Artificial Sequence
<220> FEATURE:
<223> OTHER INFORMATION: Artificial Probe

<400> SEQUENCE: 118
```
tcgcggcctg atgccgagta c                                        21

<210> SEQ ID NO 119
<211> LENGTH: 20
<212> TYPE: DNA
<213> ORGANISM: Artificial Sequence
<220> FEATURE:
<223> OTHER INFORMATION: Artificial Probe

<400> SEQUENCE: 119
cgttcctaaa gctgagtctg                                          20

<210> SEQ ID NO 120
<211> LENGTH: 15
<212> TYPE: DNA
<213> ORGANISM: Artificial Sequence
<220> FEATURE:
<223> OTHER INFORMATION: Artificial Probe

<400> SEQUENCE: 120
cgcgacagac tcagc                                               15

<210> SEQ ID NO 121
<211> LENGTH: 41
<212> TYPE: DNA
<213> ORGANISM: Artificial Sequence
<220> FEATURE:
<223> OTHER INFORMATION: Artificial Probe

<400> SEQUENCE: 121
cgttcctaaa gctgagtctg tcgcggcctg atgccgagta c                  41

<210> SEQ ID NO 122
<211> LENGTH: 15
<212> TYPE: DNA
<213> ORGANISM: Artificial Sequence
<220> FEATURE:
<223> OTHER INFORMATION: Artificial Probe

<400> SEQUENCE: 122
cgactcagac agcgc                                               15

<210> SEQ ID NO 123
<211> LENGTH: 20
<212> TYPE: DNA
<213> ORGANISM: Artificial Sequence
<220> FEATURE:
<223> OTHER INFORMATION: Artificial Probe

<400> SEQUENCE: 123
agaggggacc cgggcggagt                                          20

<210> SEQ ID NO 124
<211> LENGTH: 20
<212> TYPE: DNA
<213> ORGANISM: Artificial Sequence
<220> FEATURE:
<223> OTHER INFORMATION: Artificial Probe

<400> SEQUENCE: 124
aagccagatc gaccatcgta                                          20

<210> SEQ ID NO 125
<211> LENGTH: 15
<212> TYPE: DNA
<213> ORGANISM: Artificial Sequence

```
<220> FEATURE:
<223> OTHER INFORMATION: Artificial Probe

<400> SEQUENCE: 125
cctcttacga tggtc                                                    15

<210> SEQ ID NO 126
<211> LENGTH: 40
<212> TYPE: DNA
<213> ORGANISM: Artificial Sequence
<220> FEATURE:
<223> OTHER INFORMATION: Artificial Probe

<400> SEQUENCE: 126
aagccagatc gaccatcgta agaggggacc cgggcggagt                         40

<210> SEQ ID NO 127
<211> LENGTH: 15
<212> TYPE: DNA
<213> ORGANISM: Artificial Sequence
<220> FEATURE:
<223> OTHER INFORMATION: Artificial Probe

<400> SEQUENCE: 127
ctggtagcat tctcc                                                    15

<210> SEQ ID NO 128
<211> LENGTH: 21
<212> TYPE: DNA
<213> ORGANISM: Artificial Sequence
<220> FEATURE:
<223> OTHER INFORMATION: Artificial Probe

<400> SEQUENCE: 128
ggcgtcttgt gagcagaagc a                                             21

<210> SEQ ID NO 129
<211> LENGTH: 20
<212> TYPE: DNA
<213> ORGANISM: Artificial Sequence
<220> FEATURE:
<223> OTHER INFORMATION: Artificial Probe

<400> SEQUENCE: 129
atgatgtgca aagtgccgtc                                               20

<210> SEQ ID NO 130
<211> LENGTH: 15
<212> TYPE: DNA
<213> ORGANISM: Artificial Sequence
<220> FEATURE:
<223> OTHER INFORMATION: Artificial Probe

<400> SEQUENCE: 130
acgccgacgg cactt                                                    15

<210> SEQ ID NO 131
<211> LENGTH: 41
<212> TYPE: DNA
<213> ORGANISM: Artificial Sequence
<220> FEATURE:
<223> OTHER INFORMATION: Artificial Probe

<400> SEQUENCE: 131
atgatgtgca aagtgccgtc ggcgtcttgt gagcagaagc a                       41
```

```
<210> SEQ ID NO 132
<211> LENGTH: 15
<212> TYPE: DNA
<213> ORGANISM: Artificial Sequence
<220> FEATURE:
<223> OTHER INFORMATION: Artificial Probe

<400> SEQUENCE: 132
ttcacggcag ccgca                                                  15

<210> SEQ ID NO 133
<211> LENGTH: 19
<212> TYPE: DNA
<213> ORGANISM: Artificial Sequence
<220> FEATURE:
<223> OTHER INFORMATION: Artificial Probe

<400> SEQUENCE: 133
cgcttcgaca gcgacgtgg                                              19

<210> SEQ ID NO 134
<211> LENGTH: 20
<212> TYPE: DNA
<213> ORGANISM: Artificial Sequence
<220> FEATURE:
<223> OTHER INFORMATION: Artificial Probe

<400> SEQUENCE: 134
agagcgcatg aatccgtagt                                             20

<210> SEQ ID NO 135
<211> LENGTH: 15
<212> TYPE: DNA
<213> ORGANISM: Artificial Sequence
<220> FEATURE:
<223> OTHER INFORMATION: Artificial Probe

<400> SEQUENCE: 135
aaggcgacta cggat                                                  15

<210> SEQ ID NO 136
<211> LENGTH: 39
<212> TYPE: DNA
<213> ORGANISM: Artificial Sequence
<220> FEATURE:
<223> OTHER INFORMATION: Artificial Probe

<400> SEQUENCE: 136
agagcgcatg aatccgtagt cgcttcgaca gcgacgtgg                        39

<210> SEQ ID NO 137
<211> LENGTH: 15
<212> TYPE: DNA
<213> ORGANISM: Artificial Sequence
<220> FEATURE:
<223> OTHER INFORMATION: Artificial Probe

<400> SEQUENCE: 137
ttaggcatca gcgaa                                                  15
```

CREATION OF FUNCTIONALIZED MICROPARTICLE LIBRARIES BY OLIGONUCLEOTIDE LIGATION OR ELONGATION

RELATED APPLICATIONS

This application claims priority to U.S. Provisional Application Ser. No. 60/686,333, filed Jun. 1, 2005.

BACKGROUND REFERENCES

All Incorporated by Reference

The following can be referred to as background in order to aid in understanding of certain of the terms and expressions below.

"Oligo-Ligation via nick sealing"—Cherepanov, A. V. and de Vries, S. Kinetics and thermodynamics of nick sealing by T4 DNA ligase. Eur. J. Biochem., 270, 4315-4325 (2003).

"Chemical Ligation"—Xu, Y. and Kool, E. T. High sequence fidelity in a non-enzymatic DNA autoligation reaction. Nucleic Acids Research, 1999, vol. 27, no. 3, 875-881.

"Ligation based SNP detection"—Dubiley, S. et al. Fractionation, phosphorylation and ligation on oligonucleotide microchips to enhance sequencing by hybridization. Nucleic Acids Research, 1997, vol. 25, No. 12, 2259-2265.

"Sequencing via cleavage and ligation"—Brenner, S. et al. In vitro cloning of complex mixtures of DNA on microbeads: Physical separation of differentially expressed cDNAs. Proc. Natl. Acad. Sci. USA, vol. 97, no. 4, 1665-1670 (2000).

Hermanson, G. T. 1996. Bioconjugate Techniques, Academic Press, San Diego, Calif. Liu, P., Burdzy, A., Sowers, L. C. "DNA ligases ensure fidelity by interrogating minor groove contacts" Nucleic Acids Res. 32, 15, 4503-4511 (2004).

Broude, N. E., Sano, T., Smith, C. L., Cantor, C. R. "Enhanced DNA sequencing by hybridization" Proc. Natl. Acad. Sci. USA, Vol. 91, 3072-3076 (1994).

Iannone, M. A et al. "Multiplexed Single Nucleotide Polymorphism Genotyping by Oligonucleotide Ligation and flow cytometry", Cytometry 39: 131-140 (2000).

Gerry, N. P. et al. "Universal DNA microarray method for multiplex detection of low abundance point mutations", J. Mol. Biol. 292, 251-262 (1999).

BACKGROUND DISCUSSION

The functionalization of solid phase carriers, notably microparticles ("beads"), for chemical and biological analysis, is generally is accomplished using a variety of covalent conjugation chemistries, including the EDAC-mediated reaction (see Hermanson, G. T. 1996. Bioconjugate Techniques, Academic Press, San Diego, Calif.). Libraries of encoded functionalized microparticles for use in multiplexed formats of interrogation of nucleic acid sequence configurations—for example, those discussed in U.S. Pat. No. 6,797,524 and U.S. patent application Ser. No. 10/032,657, filed Dec. 28, 2001 (both incorporated by reference) which use the Random Encoded Array Detection (READ™) format, where a bead array is formed on a substrate (a "BeadChip™")—generally comprise a multiplicity of bead types, distinguishable, for example, by color, each type displaying one analyte-specific capture sequence. Analogous considerations apply to libraries of bead-displayed capture moieties ("receptors") for use in the multiplexed capture of proteins ("ligands").

Functionalization by covalent attachment requires the chemical modification of each analyte-specific capture probe, for example by amination of the 5'-end using amine-modified dNTP's and appropriate linker moieties, for attachment to carrier-displayed carboxyl groups in the standard EDAC-mediated reaction (Hermanson G. T, supra). Oftentimes such immobilization protocols lead to improper orientation and steric hindrance problems, most of which can be removed by introduction of spacer molecules. While widely practiced, these chemical modifications nevertheless require special purification, usually by HPLC, and this purification step lowers the yield, raises the cost, and delays procurement. Further, each analyte-specific capture probe sequence is exposed to the not always gentle conditions of the attachment reaction which may introduce damage to the capture moiety, the degree of which may be difficult to assess. In addition, from a regulatory point of view, each modified carrier may be considered a separate reagent, requiring separate qualification.

From the point of view of manufacturing of encoded solid phase carriers, it will be beneficial to have a method of producing functionalized encoded microparticle libraries, where the microparticles bear a designated probe coverage (i.e., the number of probes/bead surface area) without the need for elaborate chemical modification of the analyte-specific capture probe sequences. Further, less chemical modification is more desirable from a regulatory point of view.

SUMMARY OF THE INVENTION

The present invention discloses a method for constructing a bead-displayed library of oligonucleotide probes (or sequence-modified capture moieties such as protein-nucleic acid conjugates, see U.S. application Ser. No. 10/227,012, incorporated by reference) by ligation of a capture probe, having an analyte-specific sequence, to an anchor probe that is attached, at its 5'-end, (or possibly at the 3' end) to an encoded carrier such as a color-coded microparticle ("bead"). In one embodiment, an array of color-encoded microparticles configured in accordance with the READ™ format of multiplexed analysis (see U.S. Pat. No. 6,797,524, incorporated by reference) may be functionalized in a single on-chip reaction.

In another embodiment, a library of oligonucleotide probes (or sequence-modified capture moieties such as protein-nucleic acid conjugates, see U.S. application Ser. No. 10/227, 012) is generated by elongation of an anchor probe, using a template probe having an analyte-specific subsequence and an anchor probe-specific subsequence. The anchor probe is attached, at its 5'-end, to an encoded carrier such as a color-coded microparticle ("bead"). The template probe is annealed through the anchor probe-specific subsequence, and the anchor probe is elongated with deoxynucleotide tri-phosphate (dNTPs) complementary to the analyte-specific subsequence to generate an elongation product, capable of capturing the analyte (see U.S. application Ser. No. 10/271,602, for a description of the elongation process, incorporated by reference.)

In yet another embodiment, a library of bead bound oligonucleotide probes (or sequence-modified capture moieties such as protein-nucleic acid conjugates) is generated by either ligation or elongation as described above. However, in this case, the anchor sequence in addition to serving as an address sequence for the capture probe of interest is also utilized as a decode sequence. In this embodiment thus each bead type is defined by a combination of its fluorescent encoding as well as the unique anchor sequence attached to it that is recognized by a complementary decoder. The complementary decoder can be for example, a fluorescently labeled complementary oligonucleotide.

BRIEF DESCRIPTION OF THE FIGURES

FIG. 9 shows making an encoded bead with a capture oligo with a unique subsequence capable of hybridizing with a particular target, using hybridization-mediated elongation rather than ligation.

DETAILED DESCRIPTION

Figure 1:
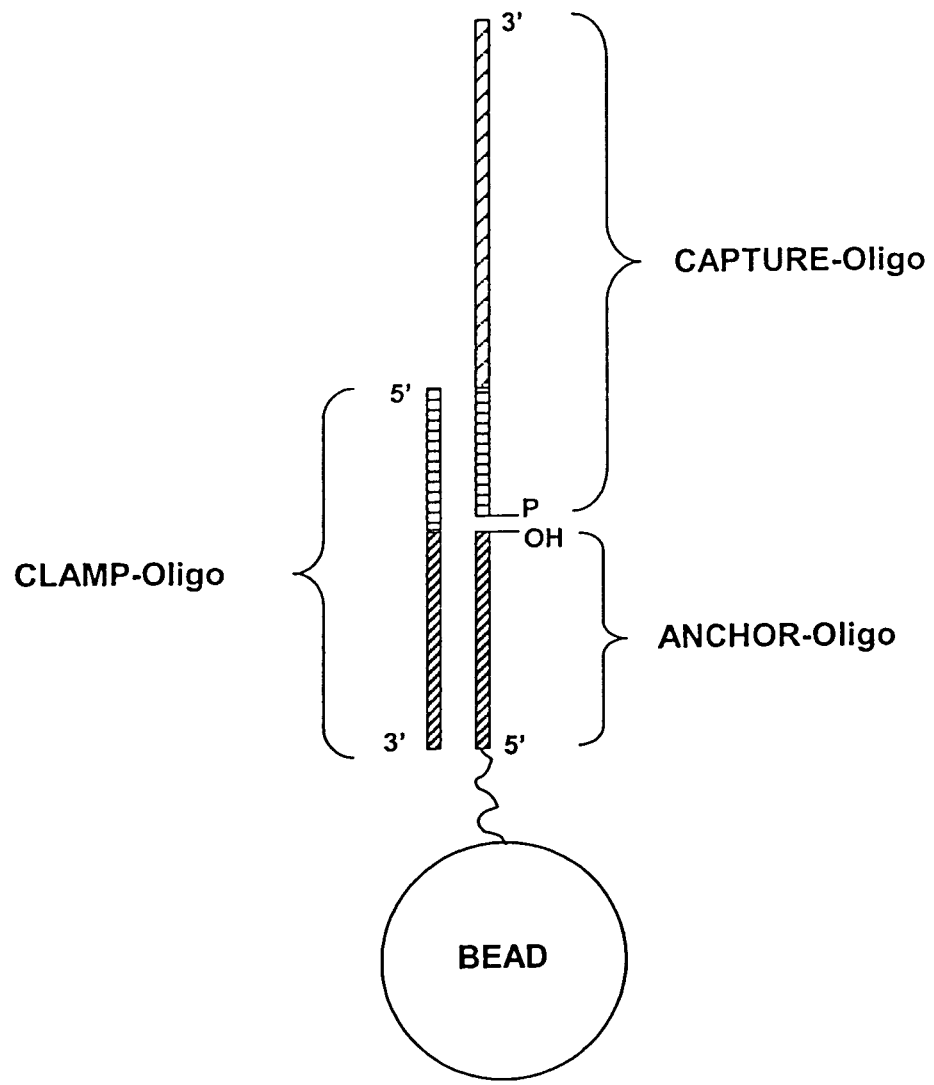
FIG. 1 depicts the bead, with an anchor oligo attached and "clamped" to a capture oligo with a unique subsequence capable of hybridizing with a particular target.

In one embodiment, encoded carriers are functionalized in two steps, namely: a first step of covalently attaching to a multiplicity of carriers an "anchor" probe having a sequence that generally is unrelated to any of the analyte-specific sequences; and a second step of ligating, to the anchor sequence on a given carrier type, a capture probe having an analyte-specific sequence that is recognizably associated with the carrier code. The step of ligating the two probes can be catalysed by a DNA ligase. The ligation is achieved by using a third clamp-probe which has a sequence so as to allow hybridization of the anchor and capture probe immediately adjacent to each other. The temporary hybridization complex in which anchor and capture sequences are annealed immediately adjacent to one another to the clamp, thereby form a duplex with a "nick" which can be sealed by a ligase-catalyzed formation of a phosphodiester bond between the 3' hydrodxyl group of the anchor sequence and the 5' phosphate group of the capture sequence (Cherepanov, A. V. and de Vries, S. Kinetics and thermodynamics of nick sealing by T4 DNA ligase. Eur. J. Biochem., 270, 4315-4325 (2003)) to produce a single oligonucleotide (FIG. 1). In another embodiment, chemical ligation also may be used (Chemical Ligation; Hermanson, G. T. 1996. Bioconjugate Techniques, Academic Press, San Diego, Calif.; Xu, Y. and Kool, E. T. High sequence fidelity in a non-enzymatic DNA autoligation reaction. Nucleic Acids Research, 1999, vol. 27, no. 3, 875-881). The use of this ligase-catalyzed reaction in several diagnostic applications, notably in a solid phase format, has been previously described. Examples include the reliable detection of a single-nucleotide polymorphism (SNP) or mutation at the site of the "nick" (Dubiley, S. et al., supra), microsequencing (Brenner, S. et al., supra).

In all such applications, DNA ligase is utilized to produce a covalent phosphodiester bond between the bead bound probe (carrying a 3' hydroxyl group) and the target oligonucleotide strand (carrying a 5' phosphate group). The methods rely on the fact that DNA ligases are sensitive to mispaired nucleotides (mismatches) present on the 3' side of the ligated junction but somewhat tolerant of mismatches on the 5' side [Liu, P., Burdzy, A., Sowers, L. C. "DNA ligases ensure fidelity by interrogating minor groove contacts" Nucleic Acids Res. 32, 15, 4503-4511 (2004)]. This requirement that DNA ligases need fully base-paired duplexes near to the DNA junction has also been exploited to improve the performance of sequencing by hybridization [Broude, N. E., Sano, T., Smith, C. L., Cantor, C. R. "Enhanced DNA sequencing by hybridization" Proc. Natl. Acad. Sci. USA, Vol. 91, 3072-3076 (1994)] multiplexed SNP detection [Iannone, M. A et al. "Multiplexed Single Nucleotide Polymorphism Genotyping by Oligonucleotide Ligation and flow cytometry", Cytometry 39: 131-140 (2000)] and for multiplexed detection of low abundance point mutations via a polymerase chain reaction/ligation detection reaction followed by hybridization to "zipcode" array [Gerry, N. P. et al. "Universal DNA microarray method for multiplex detection of low abundance point mutations", J. Mol. Biol. (1999) 292, 251-262].

Herein, ligation is applied to a different purpose, namely the creation of a library of functionalized solid phase carriers, and especially of functionalized encoded microparticles ("beads").

In one embodiment of the method, some or all of the carrier types selected for the library may display the same anchor sequence. Thus, a set of carrier types displaying the same anchor sequence would constitute a general purpose reagent which could be converted by the method of the invention to acquire analyte specificity. That is, by using clamps having sequences complementary to the same anchor sequence but different capture sequence, the same set of carrier types is readily functionalized in different ways. Further, two sublibraries containing carriers having identical color code, but displaying anchor probes of different sequence, may be mixed and decoded via interrogation of anchor sequences (that is, the anchor sequences function as an additional means by which to encode the array, which is decoded by annealing of the unique complementary sequence).

Figure 2A:
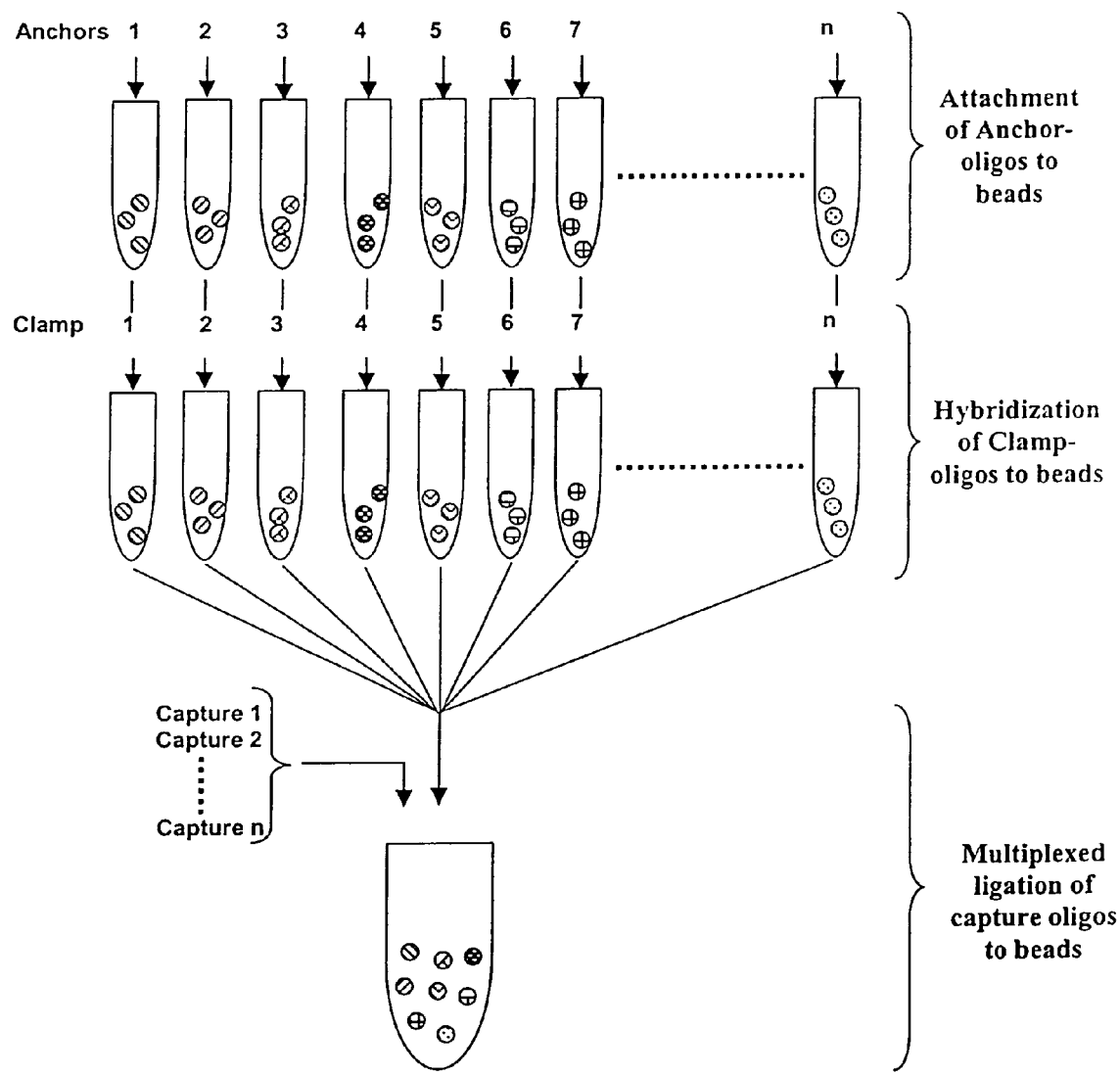
FIG. 2A depicts generating a library of capture oligo functionalized beads using the ligation methods herein.
Figure 2B:
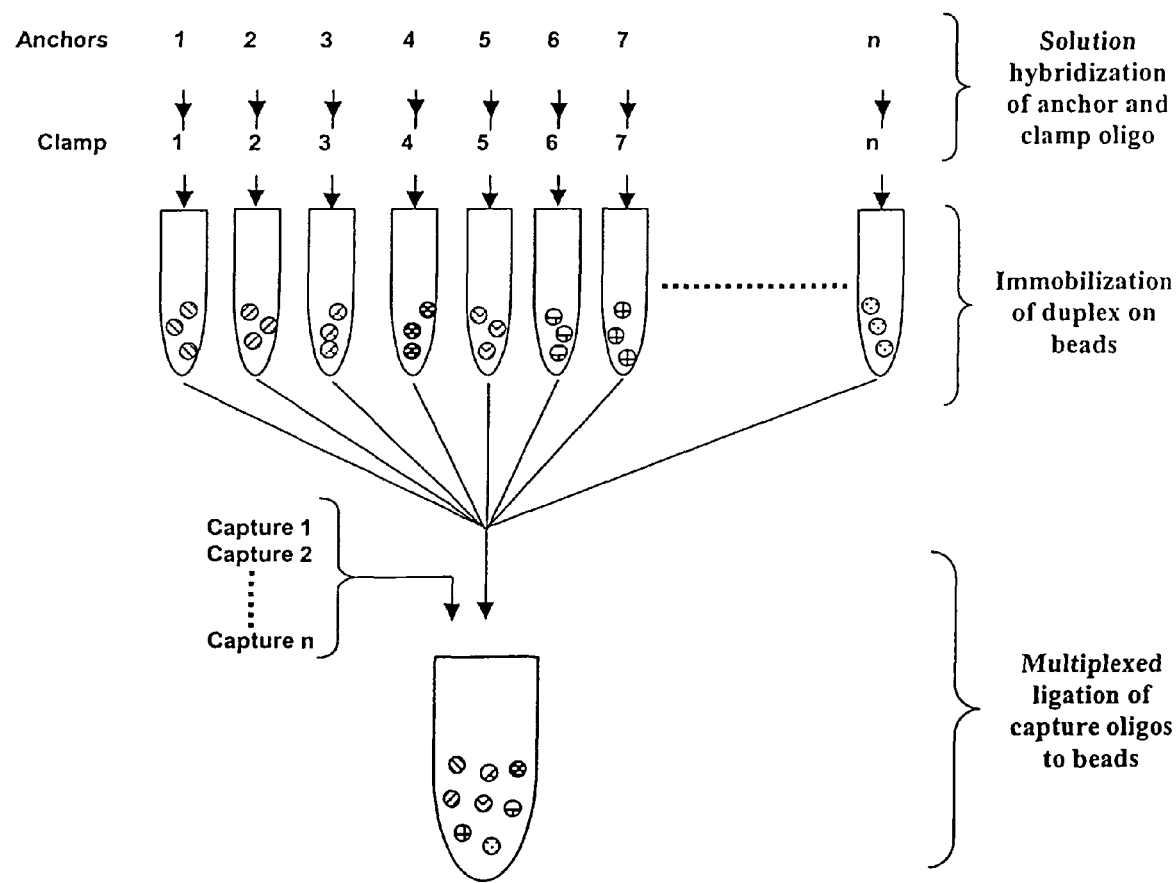
FIG. 2B depicts generating a library of capture oligo functionalized beads using the ligation methods herein
Figure 3:
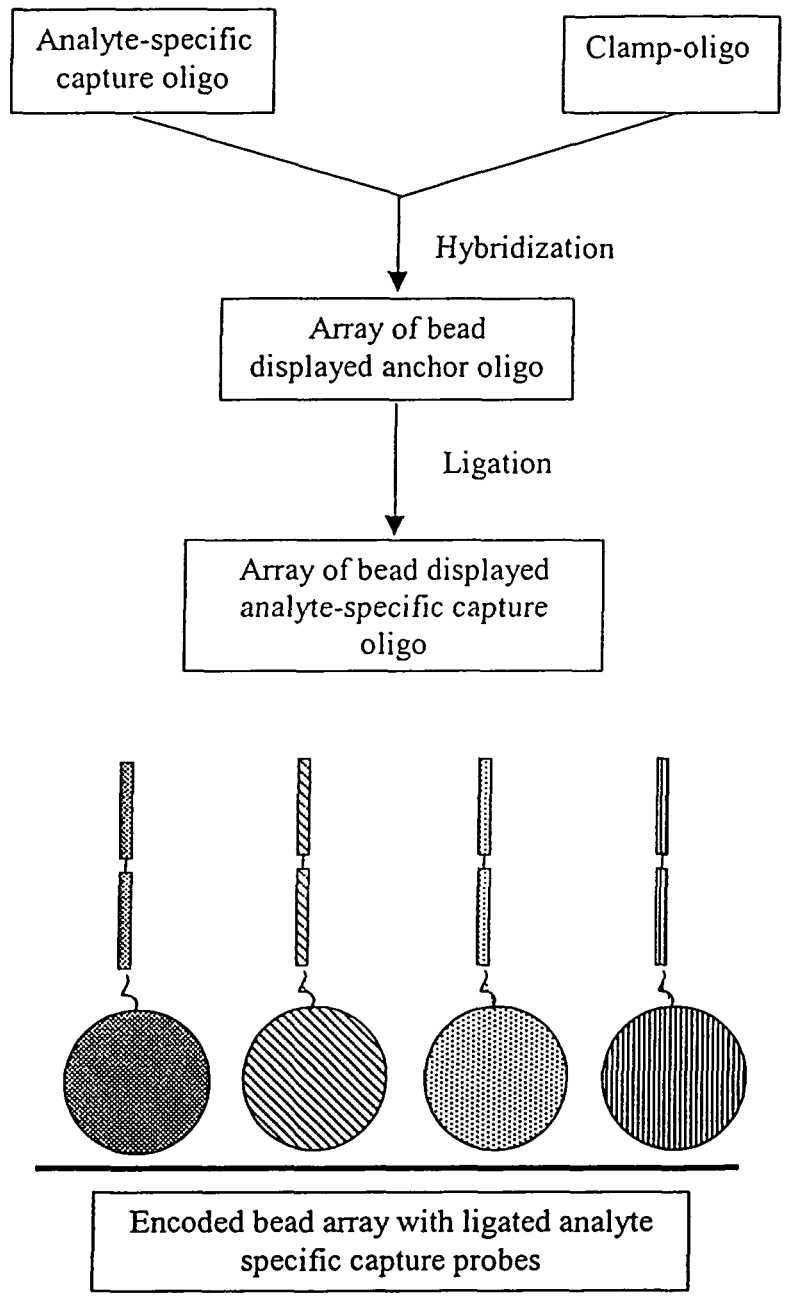
FIG. 3 depicts the process of converting a BeadChip™ displaying anchor-oligo functionalized bead array to an analyte specific bead array using methods herein.

In another embodiment, this method also permits the creation, in a single-tube reaction (FIG. 2), of an entire library of carrier-displayed probe sequences, each carrier type within the library being associated with an anchor probe having a type-specific sequence. Similarly, an assembled planar array composed of multiple color-coded types of beads, each type displaying an anchor probe having a type-specific sequence (see FIG. 3) could be converted to an analyte specfic array via the ligation protocol disclosed herein. From a manufacturing point of view, this method would permit the order of array assembly and carrier functionalization to be reversed thereby permitting functionalization to be performed, either in a wafer-scale format, or in a chip-scale format, in a manner limiting the amount of reagent consumed. See U.S. application Ser. No. 10/192,352, regarding wafer-scale and chip-scale assembly. From a regulatory point of view, the advantage of such an approach would be to be able to classify the assembled array as a general-purpose reagent. Specifically, the on-chip conversion of this general-purpose array into an application-specific array, calls for three reagents, two general-purpose reagents, namely the array displaying the set of anchor probes and a set of clamps, and a set of analyte-specific reagents, namely the capture probes. The assembled array will be composed of multiple types of beads with type-specific anchor sequences. Clamps will have one subsequence that is complementary to an anchor-sequence and one subsequence that is complementary a portion of the sequence of the capture probe. The third reagent namely the capture probe, will be an analyte-specific reagent (ASR). In one embodiment, the capture probe will have a portion that interacts with the target and another portion that interacts with the clamp.

Figure 8:
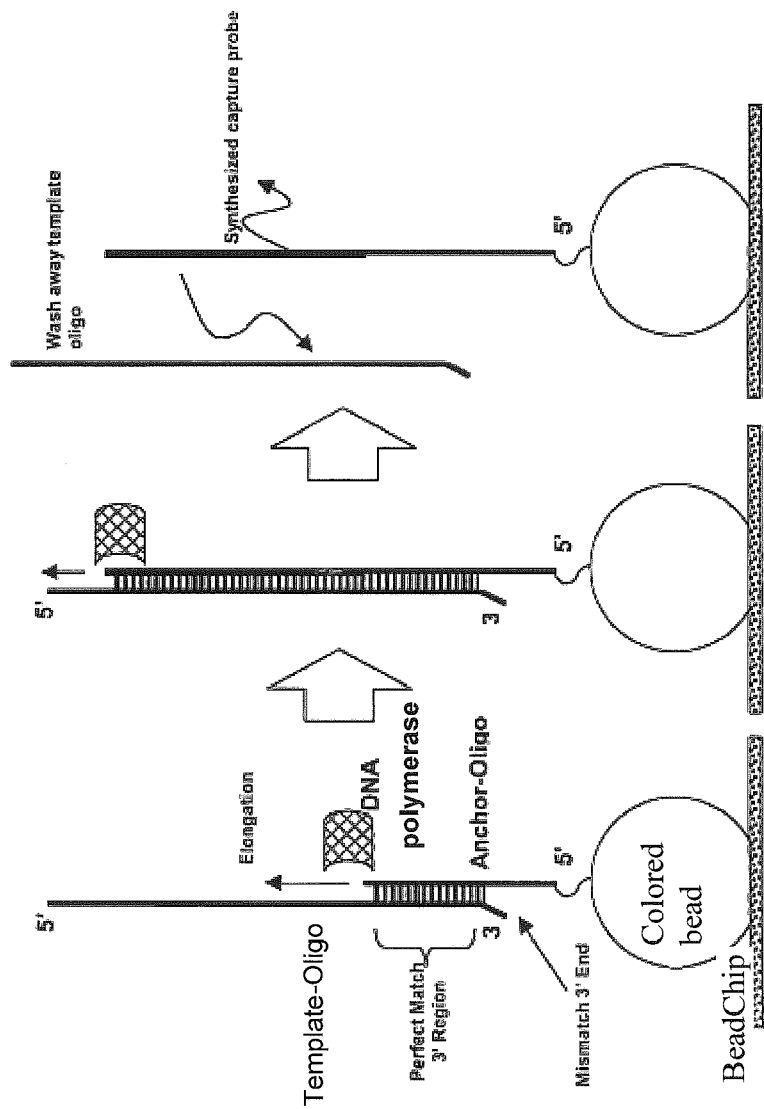

In another embodiment, the on-chip conversion of the general-purpose array into an application-specific array is performed not by ligation but by a polymerase-catalyzed elongation reaction using the analog of a clamp sequence as an elongation template. That is (see FIG. 8), as before, the 3'-end of the clamp sequence is designed to form a duplex with a specific anchor sequence displayed on an encoded microparticle under conditions permitting the elongation of the anchor sequence in a manner described in U.S. application Ser. No. 10/271,602 (incorporated by reference), but not necessarily with incorporation of fluorescently tagged dNTPs pr ddNTPs. The "overhang" of the template, typically 10-30 nt and more typically 15-25 nt in length, is selected to be identical to a specific target sequence of interest. Elongation adds to the 3' end of the anchor sequence an application-specific subsequence that is complementary to the 5'-overhang of the template sequence (see U.S. application Ser. No. 10/271, 602). Following completion of the elongation reaction, the template and reaction constituents are removed (for example by washing in water, at elevated temperature). In contrast to the ligation-catalyzed method, no capture probe sequence is needed, a fact that simplifies the design of "orthogonal" sequence sets (see also Example 8). Multiple elongation reactions can be performed in parallel, permitting the concurrent modification of an entire set of arrays. The availability of a general-purpose bead array permits a mode of co-development. Manufacturing generally will require facilities which will not be available to prospective users of the array who might wish to provide their own array composition for specific applications. The methods described herein provide for the separation of the step of array manufacturing—including the synthesis of a general-purpose library of encoded beads, the assembly of bead arrays and their packaging into desired configurations—from the step of rendering the array application specific. The methods of array modification disclosed herein thus facilitate a modality of co-development by which the array manufacturer provides a set of reagents including the general-purpose array, as well as application-specific reagents such as the template sequence, in the case of the elongation-mediated method of the invention, and application developers produce application-specific arrays "as-needed." The array manufacturer thereby can engage in strategic co-development projects and collaborations while retaining control over technical know-how, while enabling the application developer to likewise retain control of sensitive information and permitting "on-site" experimentation with different sequences in a prototyping mode requiring rapid turn-around. The methods of the invention thereby permit the array manufacturer to extend the range of application of pre-assembled arrays.

EXAMPLES

Example 1

Synthesis and Design of Oligonucleotide Sequences

All oligonucleotide synthesis was carried out by IDT (Coralville, Iowa). The sequence information and the end modifications are shown in Table 1.

TABLE 1

| Oligo # | Olgio Name | Sequence (5'-3') | |
|---|---|---|---|
| 1 | DR-70e-Biotin | Biotin-TEG-CAG AAG GAC ATC CTG GAA G | (SEQ ID NO: 1) |
| 2 | LK-70e-HA114 | TCG GTC TTC CAG GAT | (SEQ ID NO: 2) |
| 3 | P-HA114 | $PO_4^-$- ACC GAG AGA GCC TGC GGA T | (SEQ ID NO: 3) |
| 4 | T-HA114 | Cy3-ATC CGC AGG CTC TCT CGG T | (SEQ ID NO: 4) |
| 5 | LK-70e-HA107 | TCC TGC TTC CAG GAT | (SEQ ID NO: 5) |
| 6 | P-HA107 | $PO_4^-$-CAG GAG AGG CCT GAG TAT T | (SEQ ID NO: 6) |
| 7 | T-HA107 | Gy3-AAT ACT CAG GCC TCT CCT G | (SEQ ID NO: 7) |
| 8 | LK-70e-HA125 | CGC CTC TTC CAG GAT | (SEQ ID NO: 8) |
| 9 | P-HA125A | $PO_4^-$-AGG CGG TCC ATG CGG C | (SEQ ID NO: 9) |
| 10 | T-HA125A | Cy3-GCC GCA TGG ACC GCC T | (SEQ ID NO: 10) |
| 11 | DR-70e-Amine | Amine-TEG-CAG AAG GAC ATC CTG GAA G | (SEQ ID NO: 11) |
| 12 | P-HA114-Amine | Amine-TEG-ACC GAG AGA GCC TGC GGA T | (SEQ ID NO: 12) |

Example 2

In-Solution Ligation Followed by Capture of Ligated Product on Bead

Figure 4:
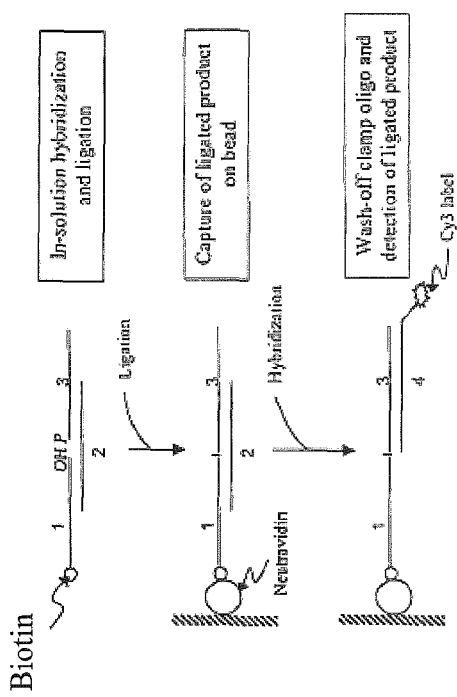
FIG. 4 depicts an in-solution ligation of probes 1 and 3 (with and without ligase), followed by attachment of the ligated product to a bead, removal of the clamp, and detection of the ligated product.
Figure 4:
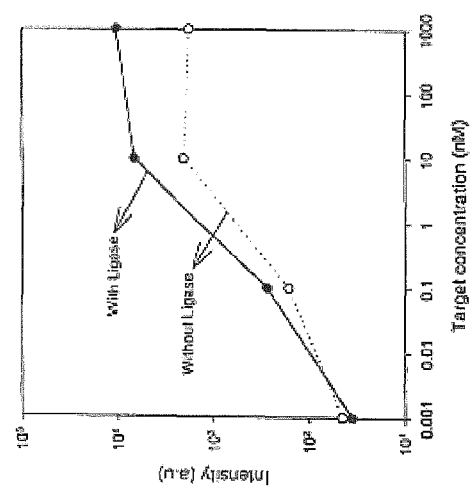

For this example oligos 1, 2 and 3 were used. Hybridization was performed by mixing 5 ul aliquots of 10 uM oligo 1, 2 and 3 in solution, heating the solution to 95° C., holding for five minutes and slowly cooling it back to room temperature. Ligation was carried out at RT for 2 hours by taking 5 ul of the hybridization mix and adding to it 2 ul of 10× T4 Ligase Reaction buffer (supplier info) and 1 ul of T4 ligase enzyme. The reaction volume was made to 20 ul by addition of 12 ul of deionized molecular biology grade water. The biotinylated reaction product was captured using color-encoded Neutravidin functionalized beads. 10 ul of 1% beads was added to 20 ul of the ligation reaction product and the reaction volume adjusted to 350 ul by adding 1×PBS. The suspension was incubated at room temperature for 30 minutes with shaking. Following capture reactions, the beads were washed 2× with PBST and re-suspended in 10 ul PBS. The beads were then assembled, on chip, and the hybridized duplex was disrupted and the clamp-oligo removed via a stringent wash at 53° C. (wash buffer:m20 mM TRIS, pH 7.5, 0.1× SSC, 0.01% SDS). Finally the detection of the ligated product was carried out via hybridization by using a series of dilutions of the labeled probe 4 in 1×TMAC. The hybridization was carried out using 20 ul of solution/chip, at 53° C. for 25 minutes. Post hybridization washing was performed using 0.7×TMAC and at 53° C. Finally the Chip was mounted on to the BAS AIS system and the fluorescent images recorded. The results are shown in FIG. 4.

Example 3

On-Bead Ligation

Figure 5:
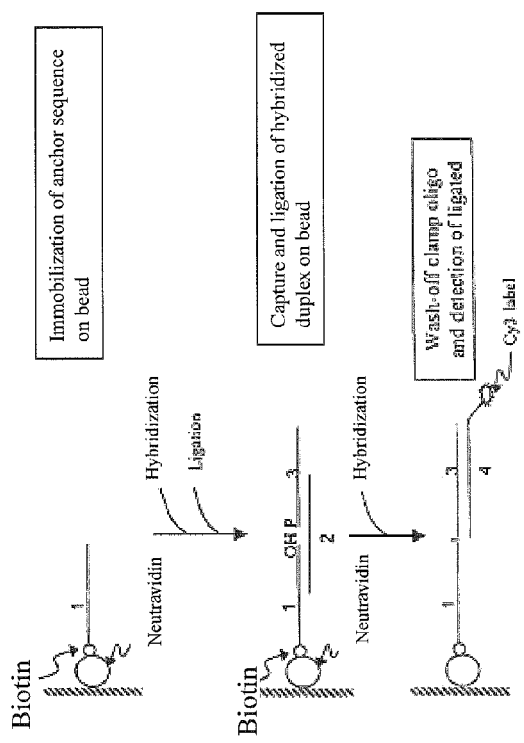
FIG. 5 depicts attachment of an anchor probe to a bead, followed by ligation of an analyte-specific probe 3, with and without ligase, removal of the clamp, and detection of the ligated product.
Figure 5:
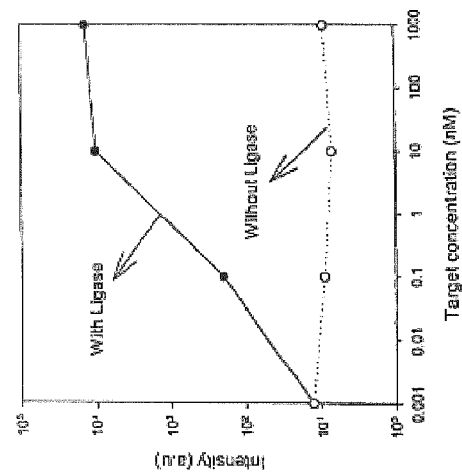

The experiment was identical to Example 1, except the anchor sequence (#1) was immobilized on a Neutravidin functionalized color encoded bead first. The ligation was hence carried out using the ternary hybridization complex (oligos 1+2+3) tethered to the bead. The results are shown in FIG. 5.

Example 4

Multiplexed on Bead Ligation

Figure 6:
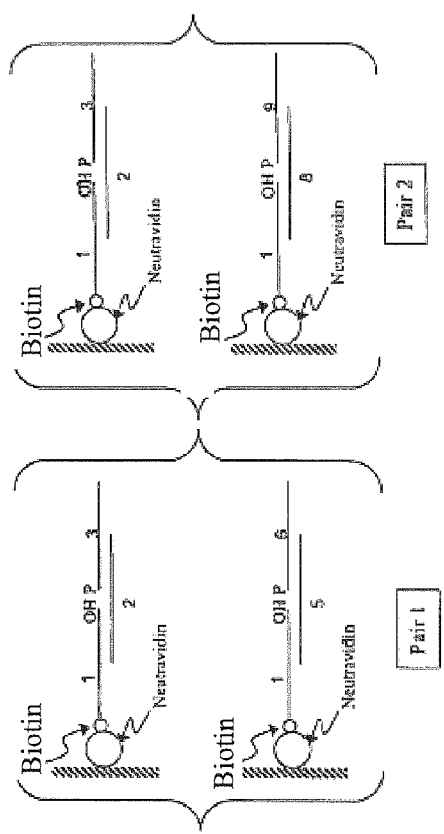
FIG. 6 depicts a summary of an experiment demonstrating multiplexed ligation. The analyte-specific probes 3, 6 and 9 are shown to be ligated in a specific manner via hybridizations to their labeled respective targets 4, 7 and 10.

Two pairs of particle captured ternary hybridization duplexes were produced using methods outlined in Example 1 and 2.
Pair 1: oligos (1+2+3) and oligos(1+5+6) and
Pair 2: (1+2+3) and (1+8+9) (each prepared separately).
On-bead ligation reaction was performed as disclosed above followed by stripping off clamp oligos 2 and 5 (pair 1) and oligos 2 and 8 (pair 2). Finally the presence and specificity of the ligated probes was checked via separate hybridizations with labeled targets 7 and 4 (pair 1) and labeled targets 10 and 4 (pair 2). The results are shown in FIG. 6.

Example 5

Comparison of Chemically Coupled and Ligated Analyte-Specific Capture Probes

Figure 7:
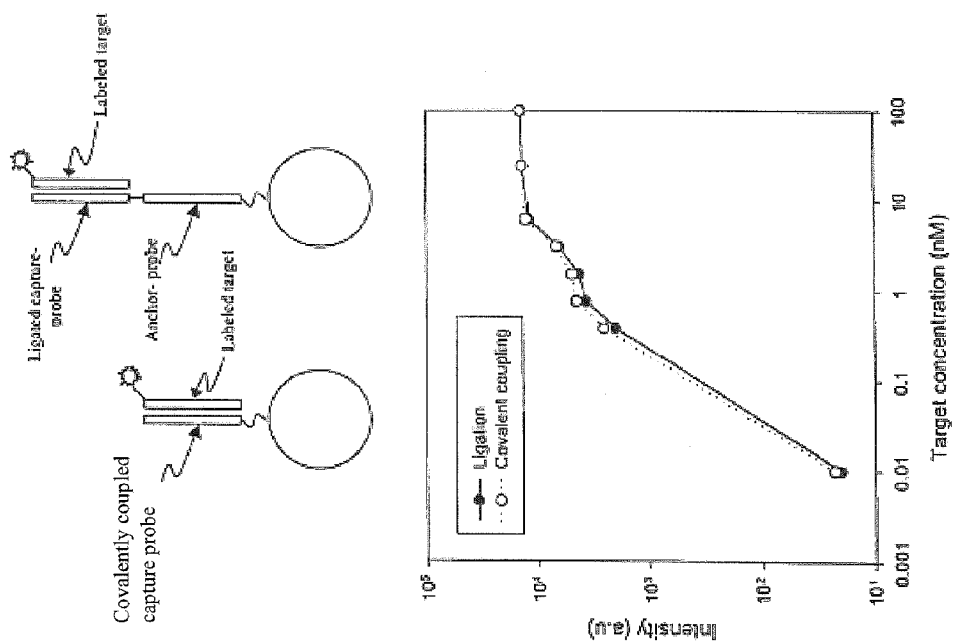
FIG. 7 depicts a summary of an experiment demonstrating that the hybridization performance of ligated and covalently coupled analyte specific probe are comparable.

5' aminated probes 11 and 12 were coupled to two different color encoded particles using an EDAC reaction under nominally identical conditions. The bead coupled with probe 12 was subjected to ligation using clamp and capture oligos 2 and 3, respectively. The bead coupled with probe 12 was directly used for target (No. 4) detection via hybridization. The results are shown in FIG. 7.

Example 6

Oligonucleotide Design for Multiplex On-Chip Ligation

A number of different computer programs are available for design of oligonucleotides to be used as PCR primers, molecular beacons or other applications. For each application a different set of constraints need to be imposed on the design process. No existing software to the best of our knowledge, provides designs or constraints suitable for use with the ligation or elongation products described herein. This example describes the design process for a set of anchor, clamp and capture probes for use in multiplexed on-chip ligation.

The function of the ss-anchor oligo is to interact with its perfect complement (clamp) and not to bind any other oligo in solution. A significant amount of scientific literature is available on the design algorithms of such non-interacting tag sequences (Gerry, N. P. et al. Universal DNA microarray method for multiplex detecion of low abundance point mutations. J. Mol. Biol. (1999) 292, 251-262; Liu, Q. et al. DNA computing on surfaces. Nature (2000) 403,175-178). For the current study we chose to use two sets of published tag sequences. The first set (30 sequences) was obtained from the genome website at Massachusetts Institute of Technology. The tags were 25-27 bases in length, $T_m$~55° C. at a salt conc. of 50 mM and contained no more than two consecutive identical bases. The tags were checked using BLAST and found non homologous to all known human genes. The second set (13 sequences) was collected from a published set of Gene-Flex™ Tag Array sequence collection (Affymetrix, Santa Clara, Calif.) that contains sequence information for 2000 oligonucleotides with minimal tendency for cross-hybridization. The sequences were 20 bases long.

The function of the ss-capture oligo is to interact with the cognate target and the clamp sequence and not bind any other oligo in solution. The choice of the capture sequence is determined by the assay of interest. For this example a set of probes for the HLA DQ locus was selected. As described above, since the sequence tags are unrelated to the particular set of probes (targeting a human gene) in question the approach is generic and can be used for any set.

Once a potential pool of anchor sequences and a set of capture sequences were chosen (see Table 3), the anchor sequences were checked for their 3' similarity. The sequences which had 3' similarity were identified and flagged (see Table 4). Next the capture sequences were checked for their similarity in the first 5 bases from the 5' end. If found, similar additional bases were inserted at the 5' end and the check repeated, until all the 21 probes had unique 5' ends. The process left the starting capture sequences minimally perturbed and a maximum of two additional 5' base insertions were needed see Table 5). Finally the set of all the tag sequences were checked for homology with the probe sequences and their reverse complements.

TABLE 3

List of anchor probe and capture probe sequences

List of anchor probe sequences

| | | | | |
|---|---|---|---|---|
| B1 | CGCAGGTATCGTATTAATTGATCTGC (SEQ ID NO: 13) | | A1 | GTTGATGTCATGTGTCGCAC (SEQ ID NO: 43) |
| B2 | CCTCATGTCAACGAAGAACAGAACC (SEQ ID NO: 14) | | A2 | TCGTGCCTTGTCATTCGGGA (SEQ ID NO: 44) |

TABLE 3-continued

List of anchor probe and capture probe sequences

| | | | | |
|---|---|---|---|---|
| B3 | ATTGAAGCCTGCCGTCGGAGACTAA (SEQ ID NO: 15) | A3 | CGTGCAAGTTACCGAGCTGA (SEQ ID NO: 45) |
| B4 | AGACTGCGTGTTGGCTCTGTCACAG (SEQ ID NO: 16) | A4 | TAGATCAGTTGGACTCGATG (SEQ ID NO: 46) |
| B5 | TTATGGTGATCAGTCAACCACCAGG (SEQ ID NO: 17) | A5 | GCAGGGAATTGCCGACCATA (SEQ ID NO: 47) |
| B6 | GAGACACCTTATGTTCTATACATGC (SEQ ID NO: 18) | A6 | ACGTTCGTCAAGAGTCGCAT (SEQ ID NO: 48) |
| B7 | TCCATGCGCTTGCTCTTCATCTAGC (SEQ ID NO: 19) | A7 | CGTTCCTAAAGCTGAGTCTG (SEQ ID NO: 49) |
| B8 | GCCTTACATACATCTGTCGGTTGTA (SEQ ID NO: 20) | A8 | GAGAGGCCGTCGCTATACAT (SEQ ID NO: 50) |
| B9 | CACAAGGAGGTCAGACCAGATTGAA (SEQ ID NO: 21) | A9 | AAGCCAGATCGACCATCGTA (SEQ ID NO: 51) |
| B10 | GCCACAGATAATATTCACATCGTGT (SEQ ID NO: 22) | A10 | GACGCCGTTATGAGAGTCCA (SEQ ID NO: 52) |
| B11 | ACACATACGATTCTGCGAACTTCAA (SEQ ID NO: 23) | A11 | ATATCGTGTCACAGGTCGTT (SEQ ID NO: 53) |
| B12 | TTACAGGATGTGCTCAACAGACGTT (SEQ ID NO: 24) | A12 | ATGATGTGCAAAGTGCCGTC (SEQ ID NO: 54) |
| B13 | GCTCACAATAATTGCATGAGTTGCC (SEQ ID NO: 25) | A13 | TCCGTCTGTTGAGTTAGGCC (SEQ ID NO: 55) |
| B14 | CTGCACTGCTCATTAATATACTTCTGG (SEQ ID NO: 26) | A14 | CTCGACCGTTAGCAGCATGA (SEQ ID NO: 56) |
| B15 | TTCACGCACTGACTGACAGACTGCTT (SEQ ID NO: 27) | A15 | CCGAGATGTACCGCTATCGT (SEQ ID NO: 57) |
| B16 | CAACATCATCACGCAGAGCATCATT (SEQ ID NO: 28) | A16 | AGAGCGCATGAATCCGTAGT (SEQ ID NO: 58) |
| B17 | GCATCAGCTAACTCCTTCGTGTATT (SEQ ID NO: 29) | | |
| B18 | GGCGTTATCACGGTAATGATTAACAGC (SEQ ID NO: 30) | | |
| B19 | ACATCAATCTCT31CTGACCGTTCCGC (SEQ ID NO: 31) | | |
| B20 | GCCTTATGCTCGAACTGACCATAAC (SEQ ID NO: 32) | | |
| B21 | CGGATATCACCACGATCAATCATAGGTAA (SEQ ID NO: 33) | | |
| B22 | CCTTAATCTGCTGCAATGCCACAGC (SEQ ID NO: 34) | | |
| B23 | TAGCTCTCCGCCTACAATGACGTCA (SEQ ID NO: 35) | | |
| B24 | AGGAACGCCTTACGTTGATTATTGA (SEQ ID NO: 36) | | |
| B25 | GAGTCAGTACCGATGTAGCCGATAA (SEQ ID NO: 37) | | |
| B26 | ACTCGAATGAACCAGGCGATAATGG (SEQ ID NO: 38) | | |
| B27 | ATTATATCTGCCGCGAAGGTACGCC (SEQ ID NO: 39) | | |
| B28 | GGACAGACAGTGGCTACGGCTCAGTT (SEQ ID NO: 40) | | |

TABLE 3-continued

List of anchor probe and capture probe sequences

B29 CGGTATTCGCTTAATTCAGCACAAC
(SEQ ID NO: 41)

B30 GCTCTTACCTGTTGTGCAGATATAA
(SEQ ID NO: 42)

List of HLA DQ capture probe sequences

DQ101 CGGGGTGTGACCAGACACA
(SEQ ID NO: 59)

DQ102 GGGTGTACCGGGCAGTGAC
(SEQ ID NO: 60)

DQ103 GCGGCCTAGCGCCGAGTAC
(SEQ ID NO: 61)

DQ104 GCGGCCTGTTGCCGAGT
(SEQ ID NO: 62)

DQ105 CGTTATGTGACCAGATACA
(SEQ ID NO: 63)

DQ106 CGTCTTGTAACCAGACACA
(SEQ ID NO: 64)

DQ107 CGTCTTGTGACCAGATACA
(SEQ ID NO: 65)

DQ108 GCGGCCTGATGCCGAGTAC
(SEQ ID NO: 66)

DQ109 GACCCGAGCGGAGTTGGAC
(SEQ ID NO: 67)

DQ110 GAGGGGACCCGGGCGGAGT
(SEQ ID NO: 68)

DQ111 CGTCTTGTAACCAGATACA
(SEQ ID NO: 69)

DQ112 CGTCTTGTGAGCAGAAGCA
(SEQ ID NO: 70)

DQ113 CGACGTGGAGGTGTACCGG
(SEQ ID NO: 71)

DQ114 GCCGCCTGACGCCGAGT
(SEQ ID NO: 72)

DQ115 GGCCGCCTGCCGCCGAGT
(SEQ ID NO: 73)

DQ116 GACCGAGCGCGTGCGGGGT
(SEQ ID NO: 74)

DQ117 GCTGGGGCGGCTTGACGCC
(SEQ ID NO: 75)

DQ118 GGGTGTATCGGGCGGTGAC
(SEQ ID NO: 76)

DQ119 GGCGGCCTGACGCCGAGT
(SEQ ID NO: 77)

DQ120 CGCTTCGACAGCGACGTGG
(SEQ ID NO: 78)

DQ121 AACCGAGAAGAGTACGTGC
(SEQ ID NO: 79)

TABLE 4

Pairs of anchor probes showing 3' similarity

A1 GTTGATGTCATGTGTCGCAC
(SEQ ID NO: 80)

A6 ACGTTCGTCAAGAGTCGCAT
(SEQ ID NO: 81)

B25 GAGTCAGTACCGATGTAGCCATAA
(SEQ ID NO: 82)

B30 GCTCTTACCTGTTGTGCAGATATAA
(SEQ ID NO: 83)

B18 GGCGTTATCACGGTAATGATTAACAGC
(SEQ ID NO: 84)

E22 CCTTAATCTGCTGCAATGCCACAGC
(SEQ ID NO: 85)

A14 CTCGACCGTTAGCAGCATGA
(SEQ ID NO: 86)

B6 GAGACACCTTATGTTCTATACATGC
(SEQ ID NO: 87)

B1 CGCAGGTATCGTATTAATTGATCTGC
(SEQ ID NO: 88)

B14 CTGCACTGCTCATTAATATACTTCTGG
(SEQ ID NO: 89)

A11 ATATCGTGTCACAGGTCGTT
(SEQ ID NO: 90)

B12 TTACAGGATGTGCTCAACAGACGTT
(SEQ ID NO: 91)

TABLE 5

Revised capture probe sequences with unique 5' ends

DQ101 CGGGGTGTGACCAGACACA
(SEQ ID NO: 92)

DQ102 TTGGGTGTACCGGGCAGTGAC
(SEQ ID NO: 93)

DQ103 TAGCGGCCTAGCGCCGAGTAC
(SEQ ID NO: 94)

DQ104 TTGCGGCCTGTTGCCGAGT
(SEQ ID NO: 95)

DQ105 CGTTATGTGACCAGATACA
(SEQ ID NO: 96)

TABLE 5-continued

Revised capture probe sequences with unique 5' ends

| | |
|---|---|
| DQ106 | TACGTCTTGTAACCAGACACA (SEQ ID NO: 97) |
| DQ107 | TTCGTCTTGTGACCAGATACA (SEQ ID NO: 98) |
| DQ108 | TCGCGGCCTGATGCCGAGTAC (SEQ ID NO: 99) |
| DQ109 | GACCCGAGCGGAGTTGGAC (SEQ ID NO: 100) |
| DQ110 | AGAGGGGACCCGGGCGGAGT (SEQ ID NO: 101) |
| DQ111 | TCCGTCTTGTAACCAGATACA (SEQ ID NO: 102) |
| DQ112 | GGCGTCTTGTGAGCAGAAGCA (SEQ ID NO: 103) |
| DQ113 | CGACGTGGAGGTGTACCGG (SEQ ID NO: 104) |
| DQ114 | CAGCCGCCTGACGCCGAGT (SEQ ID NO: 105) |
| DQ115 | GGCCGCCTGCCGCCGAGT (SEQ ID NO: 106) |
| DQ116 | TAGACCGAGCGCGTGCGGGGT (SEQ ID NO: 107) |
| DQ117 | GCTGGGGCGGCTTGACGCC (SEQ ID NO: 108) |
| DQ118 | TAGGGTGTATCGGGCGGTGAC (SEQ ID NO: 109) |
| DQ119 | ATGGCGGCCTGACGCCGAGT (SEQ ID NO: 110) |
| DQ120 | CGCTTCGACAGCGACGTGG (SEQ ID NO: 111) |
| DQ121 | AACCGAGAAGAGTACGTGC (SEQ ID NO: 112) |

Example 7

Multiplex On-Chip Ligation

Table 6 below summarizes the 5-probe system chosen for the multiplexed experiment. The table lists the individual sets consisting of the capture, clamp and the anchor probe and also shows their alignment.

TABLE 6

Sequences for the multiplexed ligation experiment

DQ107CAPT
Phosphate-TTC GTC TTG TGA CCA GAT ACA                        (SEQ ID NO: 113)

DQ107ANCH
Amine-GTT GAT GTC ATG TGT CGC AC                             (SEQ ID NO: 114)
DQ107CLMP
ACG AAG TGC GAC ACA                                          (SEQ ID NO: 115)

5'-gtt gat gtc atg tgt cgc ac ttc gtc ttg tga cca gat aca-3'   (SEQ ID NO: 116)

ac aca gcg tg aag ca                           (SEQ ID NO: 117)

DQ108CAPT
Phosphate-TCG CGG CCT GAT GCC GAG TAC                        (SEQ ID NO: 118)

DQ108ANCH
Amine-CGT TCC TAA AGC TGA GTC TG                             (SEQ ID NO: 119)

DQ108CLMP
CGC GAC AGA CTC AGC                                          (SEQ ID NO: 120)

5'-cgt tcc taa agc tga gtc tg tcg cgg cct gat gcc gag tac-3'   (SEQ ID NO: 121)

cg act cag ac agc gc                           (SEQ ID NO: 122)

DQ110CAPT
Phosphate-AGA GGG GAC CCG GGC GGA GT                         (SEQ ID NO: 123)

DQ110ANCH
Amine-AAG CCA GAT CGA CCA TCG TA                             (SEQ ID NO: 124)

DQ110CLMP
CCT CTT ACG ATG GTC                                          (SEQ ID NO: 125)

5'-aag cca gat cga cca tcg ta aga ggg gac ccg ggc gga gt-3'    (SEQ ID NO: 126)

ct ggt agc at tct cc                           (SEQ ID NO: 127)

DQ112CAPT
Phosphate-GGC GTC TTG TGA GCA GAA GCA                        (SEQ ID NO: 128)

TABLE 6-continued

Sequences for the multiplexed ligation experiment

```
DQ112ANCH
Amine-ATG ATG TGC AAA GTG CCG TC                         (SEQ ID NO: 129)

DQ112CLMP
ACG CCG ACG GCA CTT                                      (SEQ ID NO: 130)

5'-atg atg tgc aaa gtg ccg tc ggc gtc ttg tga gca gaa gca-3'  (SEQ ID NO: 131)
             tt cac ggc ag ccg ca                        (SEQ ID NO: 132)

DQ120CAPT
Phosphate-CGC TTC GAC AGC GAC GTG G                      (SEQ ID NO: 133)

DQ120ANCH
Amine-AGA GCG CAT GAA TCC GTA GT                         (SEQ ID NO: 134)

DQ120CLMP
AAG GCG ACT ACG GAT                                      (SEQ ID NO: 135)

5'-aga gcg cat gaa tcc gta gt cgc ttc gac agc gac gtg g-3'  (SEQ ID NO: 136)
             tt agg cat ca gcg aa                        (SEQ ID NO: 137)
```

The experiment was carried out as follows:

Step 1

Coupling of Aminated Anchor Probes to the Beads

The aminated anchor probes (DQ107ANCH, DQ108ANCH, DQ110ANCH, DQ112ANCH and DQ120ANCH) and one negative control probe (N18) were covalently attached to six different color encoded microparticles using EDAC chemistry. They were then used to manufacture several BAS BeadChips.

Step 2

Annealing of Capture Probe and Clamps

The following mixtures were made in five different eppendorf tubes and incubated at 94° C. for 10 minutes followed by cooling to room temperature.

| Tube 1 | Tube 2 | Tube 3 | Tube 4 | Tube 5 |
|---|---|---|---|---|
| 1 ul 100 uM DQ107CAPT | 1 ul 100 uM DQ108CAPT | 1 ul 100 uM DQ110CAPT | 1 ul 100 uM DQ112CAPT | 1 ul 100 uM DQ120CAPT |
| 1 ul 100 uM DQ107CLMP | 1 ul 100 uM DQ108CLMP | 1 ul 100 uM DQ110CLMP | 1 ul 100 uM DQ112CLMP | 1 ul 100 uM DQ120CLMP |
| 18 ul of DI water | 18 ul of DI water | 18 ul of DI water | 18 ul of DI water | 18 ul of DI water |

Step 3

Preparation of the Ligation Master Mix

The ligation reaction mix was prepared by mixing together i) 10× Ligation Reaction buffer: 2 ul (New England BioLabs, Ipswich, Mass.)

ii) T4 Ligase enzyme: 1 ul (New England BioLabs, Ipswich, Mass.)

iii) 3 ul of each of the annealed product from step 2 (total 15 ul)

iv) 2 ul of DI water

Step 4

On-Chip Ligation

The ligation mix (20 ul) prepared in step 3 was added to a BeadChip prepared in step 1 and incubated at RT for 1.5 hr in a humid chamber. Following this the chip was washed thoroughly at room temperature with DI water to strip off the clamp and any un-ligated capture probe. The chip was dried and stored at 4° C. until further use.

Step 5

On-Chip Hybridization

Five oligos (reverse complements of the capture probes listed in Table 6) with a 5' biotin tag were used as the hybridization targets. 1 uM solutions of each were prepared using 1× TMAC solution. A pooled target mixture was also prepared using 1×TMAC and all the five targets (Final target conc. 1 uM). 20 ul of each target solution was aliquoted onto a separate chip and incubated at 53° C. for 15 minutes. The sample was aspirated off and the chips were then washed with 20 ul 1×SSC buffer with 0.1% SDS at 53° C. for 10 min. Following this the chips were stained with a 1:200 Streptavidin-CY3 solution and washed with 20 ul 1×SSC buffer with 0.1% SDS at RT for 5 min. The slide was then fixed with a fixative solution and finally rinsed with a stop solution and dried. The fluorescent signals were read using a BAS AIS system. The results are shown in Table 7 below. Except DQ108 capture probe (which showed no signal), all other probes performed in a satisfactory fashion.

TABLE 7 results of multiplexed on-chip ligation

| Syn. target | Probes | | | | | |
|---|---|---|---|---|---|---|
| (1 uM) | HD107 | HD108 | HD110 | HD112 | HD120 | N_18* |
| DQ107 TAR | 491 | 20 | 12 | 12 | 34 | 10 |
| DQ108 TAR | 15 | 34 | 8 | 11 | 34 | 6 |
| DQ110 TAR | 30 | 34 | 1816 | 31 | 52 | 19 |
| DQ112 TAR | 21 | 25 | 12 | 821 | 42 | 12 |
| DQ120 TAR | 19 | 22 | 15 | 18 | 703 | 13 |
| 5 target mix | 257 | 97 | 1634 | 593 | 448 | 36 |

*negative control probe

Example 8

Design of Multiplex On-Chip Elongation

This preferred embodiment requires a unique set of anchor sequences (each such sequence uniquely associated to an optically decodable code, such as a fluorescently encoded microparticle) and a matched template sequence, that is, a template sequence with a 3'-terminal subsequence that is complementary to the anchor sequence and a 5'-terminal subsequence that is identical to a selected subsequence within a target sequence, for example, a target subsequence comprising a designated variable site of interest. The tag-sequences discussed below in Example 6, with no mutual cross-reactivity and minimal homology to the human genome can be utilized for the anchor sequences of interest. Once the anchor sequences and the target subsequences of interest have been identified, the template sequence is constructed as described above. The process of array modification involves (see FIG. 8) contacting a pool of the template oligos with an array of microparticles pre-functionalized with the anchor oligos in presence of dNTPs or ddNTPs and a DNA-polymerase enzyme in a suitable buffer. The polymerase extends the 3' end of the anchor sequences in matched anchor-template duplexes in accordance with the 5' overhang of the template sequence. Finally, the template sequence is de-hybridized leaving behind the newly synthesized ss-oligo, which can now function as the capture probe of interest. It is worthwhile to mention that this particular approach of array modification requires only one unmodified template sequence to be pre-synthesized.

It should be understood that the terms, expressions and examples herein are exemplary only and not limiting, and that the scope of the invention is defined only in the claims which follow, and includes all equivalents of the subject matter of those claims.

What is claimed is:

1. A method of creating a carrier-displayed library of oligonucleotide probes from a carrier-displayed general purpose library of oligonucleotide probes in a single multiplex reaction by ligation of anchor probes attached to encoded carriers and analyte-specific capture probes, comprising:

a. providing a general purpose library of anchor oligonucleotide probes, wherein anchor probes having different sequences are attached to differently encoded carriers;

b. providing an analyte specific library of capture oligonucleotide probes which include subsequences complementary to designated analyte sequences;

c. providing a library of clamp probes, each member of the library having a unique sequence and a first subsequence complementary to a terminal subsequence of an anchor probe and a second subsequence complementary to a terminal subsequence of a capture probe such that for each of the clamp probes, their entire first subsequence participates in duplex formation with the complementary anchor oligonucleotide probes and their entire second subsequence participates in duplex formation with the capture oligonucleotide probes without any internal mismatches or terminal overhangs;

d. providing conditions permitting formation of tertiary complexes of capture probes, anchor probes and clamp probes;

e. incubating said tertiary complexes under conditions such that the capture and the anchor probe are ligated to each other to generate a single oligonucleotide, wherein no monomers are added during or after ligation, and f. washing to release the clamp probes from the tertiary complexes.

2. The method of claim 1 wherein the carriers are microbeads and the encoding is with an optically detectable signal.

3. The method of claim 2 wherein the optically detectable signal is color.

4. A method of creating a carrier-displayed library of oligonucleotide capture probes in a single multiplex reaction by ligation of a first set of probes, including probes of differing sequences attached to encoded carriers, to a second set of probes having subsequences complementary to an analyte, by:

forming a complex using a third set of probes, each set having a unique sequence, capable of annealing to a first subsequence at or near the terminus of members of the first set and a second subsequence at or near the terminus of members of the second set wherein said third set of probes forms a duplex with both said first and second set; and ligating said first set to said second set of probes, wherein no monomers are added during or after ligation.

* * * * *